US011583593B2

(12) United States Patent
Thomas-Karyat

(10) Patent No.: US 11,583,593 B2
(45) Date of Patent: Feb. 21, 2023

(54) ANTIBODY-ALK5 INHIBITOR CONJUGATES AND THEIR USES

(71) Applicant: Synthis Therapeutics, Inc., New York, NY (US)

(72) Inventor: Dori A. Thomas-Karyat, Jersey City, NJ (US)

(73) Assignee: Synthis Therapeutics, Inc., New York, NY (US)

(*) Notice: Subject to any disclaimer, the term of this patent is extended or adjusted under 35 U.S.C. 154(b) by 438 days.

(21) Appl. No.: 16/654,194

(22) Filed: Oct. 16, 2019

(65) Prior Publication Data

US 2020/0147234 A1 May 14, 2020

Related U.S. Application Data

(63) Continuation of application No. 16/286,122, filed on Feb. 26, 2019, now abandoned, which is a continuation of application No. 16/029,351, filed on Jul. 6, 2018, now abandoned, which is a continuation of application No. 15/404,233, filed on Jan. 12, 2017, now abandoned.

(60) Provisional application No. 62/278,928, filed on Jan. 14, 2016.

(51) Int. Cl.
*A61K 47/68* (2017.01)
*C07K 16/30* (2006.01)
*C07K 16/28* (2006.01)

(52) U.S. Cl.
CPC ...... *A61K 47/6851* (2017.08); *C07K 16/2881* (2013.01); *C07K 16/30* (2013.01); *C07K 2317/21* (2013.01); *C07K 2317/24* (2013.01); *C07K 2317/54* (2013.01); *C07K 2317/55* (2013.01); *C07K 2317/56* (2013.01)

(58) Field of Classification Search
CPC combination set(s) only.
See application file for complete search history.

(56) References Cited

U.S. PATENT DOCUMENTS

| | | | |
|---|---|---|---|
| 6,491,916 B1 | 12/2002 | Bluestone et al. | |
| 7,189,733 B2 | 3/2007 | Scarborough et al. | |
| 7,557,130 B2 | 7/2009 | Aujla et al. | |
| 7,678,810 B2 | 3/2010 | Sato et al. | |
| 8,080,568 B1 | 12/2011 | Kim et al. | |
| 8,268,857 B2 | 9/2012 | Scarborough et al. | |
| 8,871,744 B2* | 10/2014 | Barbeau | A61P 35/00 514/23 |
| 8,900,589 B2* | 12/2014 | Beria | A61P 35/02 530/391.1 |
| 9,073,918 B2 | 7/2015 | Kwok et al. | |
| 2004/0063745 A1 | 4/2004 | Gellibert et al. | |
| 2005/0260215 A1 | 11/2005 | Abrahmsen et al. | |
| 2012/0022016 A1 | 1/2012 | Barbeau | |
| 2014/0086942 A1* | 3/2014 | Carter | A61P 35/00 424/179.1 |
| 2015/0141624 A1 | 5/2015 | Barnett et al. | |
| 2015/0315293 A1 | 11/2015 | Damelin et al. | |
| 2017/0158772 A1 | 6/2017 | Thompson et al. | |
| 2017/0216401 A1 | 8/2017 | Jachimczak et al. | |
| 2017/0281767 A1 | 10/2017 | Chang et al. | |
| 2018/0030128 A1 | 2/2018 | Weiner et al. | |
| 2018/0078655 A1 | 3/2018 | Dziadek et al. | |
| 2018/0125999 A1 | 5/2018 | Reilly et al. | |
| 2019/0240346 A1 | 8/2019 | Sugo et al. | |
| 2021/0299268 A1 | 9/2021 | Thomas-Karyat | |

FOREIGN PATENT DOCUMENTS

| | | |
|---|---|---|
| EP | 2 176 295 | 11/2014 |
| WO | 2004/016606 A1 | 2/2004 |
| WO | 2004/021989 A2 | 3/2004 |
| WO | 2005/081711 A2 | 9/2005 |
| WO | 2006/117306 A1 | 11/2006 |
| WO | 2007/070866 A2 | 6/2007 |
| WO | 2015/118175 | 8/2015 |
| WO | 2015/118175 A2 | 8/2015 |
| WO | 2016/112870 A1 | 7/2016 |
| WO | 2016/115218 A1 | 7/2016 |
| WO | 2016/166341 A1 | 10/2016 |
| WO | 2017/221883 A1 | 12/2017 |
| WO | 2018/067331 A1 | 4/2018 |
| WO | 2018/140831 | 8/2018 |
| WO | 2018/208720 A1 | 11/2018 |
| WO | 2018/227018 | 12/2018 |
| WO | 2019/0840601 | 5/2019 |
| WO | 2019/195278 A1 | 10/2019 |
| WO | 2020/013803 | 1/2020 |
| WO | 2020/256751 | 12/2020 |

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Strop et al., Chemistry and Biology 20: 161-167 (Year: 2013).*
Piche-Nicholas et al., MABS 10(1): 81-94 (Year: 2018).*
Yoon et al., EMBO Molecular Medicine 5: 1720-1739 (Year: 2013).*
Yingling et al., Nature Reviews Drug Discovery 3: 1011-1022 (Year: 2004).*
Ciayadi et al., Biorganic & Medicinal Chemistry 21: 6496-6500 (Year: 2013).*
Gellibert et al., Journal Med Chem 47: 4494-4506 (Year: 2004).*
Akhurst and Hata, 2012, "Targeting the TGFβ signalling pathway in disease," Nat Rev Drug Discov 11(10):790-811.
Bonafoux et al., 2009, "Strategies for TGF-β modulation: a review of recent patents," Expert Opin. Ther. Patents 19(12):1759-1769.
Byfield et al., 2004, "SB-505124 Is a Selective Inhibitor of Transforming Growth Factor-β Type I Receptors ALK4, ALK5, and ALK7," Mol. Pharmacol. 65:744-752.
Calone et al., 2012, "Inhibition of TGFβ Signaling and its Implications in Anticancer Treatments," Ex. Oncol. 34(1):9-16.
Connolly et al., 2012, "Complexities of TGF-β Targeted Cancer Therapy," Int. J. Biol. Sci. 8(7):964-978.

(Continued)

*Primary Examiner* — Phuong Huynh
(74) *Attorney, Agent, or Firm* — Biospark Intellectual Property Law

(57) ABSTRACT

The present disclosure relates to antibody-drug conjugates comprising ALK5 inhibitors and their uses.

3 Claims, 16 Drawing Sheets

(56) References Cited

OTHER PUBLICATIONS

De Panfilis, 1998, "CD8+ cytolytic T lymphocytes and the skin," Exp. Dermatol. 7:121-131.
Donkor et al., 2011, "T Cell Surveillance of Oncogene-Induced Prostate Cancer Is Impeded by T Cell-Derived TGF-β1 Cytokine," Immunity 35:123-134.
Ducry et al., 2010, "Antibody-Drug Conjugates: Linking Cytotoxic Payloads to Monoclonal Antibodies," Bioconjugate Chem. 21:5-13.
Ehata et al., 2007, "Ki26894, a novel transforming growth factor-β type I receptor kinase inhibitor, inhibits in vitro invasion and in vivo bone metastasis of a human breast cancer cell line," Cancer Sci. 98(1): 127-133.
Gate et al., 2014, "T-cell TGF-β signaling abrogation restricts medulloblastoma progression," PNAS 111(33):E3458-E3466.
Gorelik & Flavell, 2001, "Immune-mediated eradication of tumors through the blockade of transforming growth factor-β signaling in T cells," Nature Medicine 7(10):1118-1122.
Herbertz et al., 2015, "Clinical development of galunisertib (LY2157299 monohydrate), a small molecule inhibitor of transforming growth factor-beta signaling pathway," Drug Design, Development and Therapy 9 4479-4499.
Inman et al., 2002, "SB-431542 Is a Potent and Specific Inhibitor of Transforming Growth Factor-β Superfamily Type I Activin Receptor-Like Kinase (ALK) Receptors ALK4, ALK5, and ALK7," Mol. Pharmacol. 62:65-74.
Kano et al., 2007, "Improvement of cancer-targeting therapy, using nanocarriers for intractable solid tumors by inhibition of TGF-β signaling," PNAS 104(9):3460-3465.
Leivonen et al., 2007, "Transforming growth factor-β signaling in cancer invasion and metastasis," Int. J. Cancer 121:2119-2124.
Matsuyama et al., 2003, "SB-431542 and Gleevec Inhibit Transforming Growth Factor-β-Induced Proliferation of Human Osteosarcoma Cells," Cancer Research 63:7791-7798.
Neuzillet et al., 2015, "Targeting the TGFβ pathway for cancer therapy," Pharmacology and Therapeutics 147:22-31.
Oh and Li, 2013, "TGF-β: Guardian of T Cell Function," J Immunol 191:3973-3979.
Pickup et al., 2013, "The roles of TGFβ in the tumour microenvironment," Nat. Rev. Cancer 13:788-799.
Tsuchida et al., 2008, "Signal Transduction Pathway through Activin Receptors as a Therapeutic Target of Musculoskeletal Diseases and Cancer," Endocrine Journal 55(1):11-21.
Wang et al., 2015, "An Immunosuppressive Antibody-Drug Conjugate," J. Am. Chem. Soc. 137:3229-3232.
Wang et al., 2015, Supporting Information, pp. S1-S21 for "An Immunosuppressive Antibody-Drug Conjugate," J. Am. Chem. Soc. 137:3229-3232.
Xu, 2012, "Challenges in Characterization of Heterogeneity in an Antibody Druge Conjugate: a Case Study," 2012 AAPS National Biotechnology Conference.
Yingling et al., 2004, "Development of TGF-β Signalling Inhibitors for Cancer Therapy," Nat. Rev. Drug Discovery 3:1011-1022.
Yoon et al., 2013, "Activin receptor-like kinase5 inhibition suppresses mouse melanoma by ubiquitin degradation of Smad4, thereby derepressing eomesodermin in cytotoxic T lymphocytes," EMBO Mol. Med. 5:1720-1739.
International Search Report dated Sep. 17, 2018 in connection with PCT/US2018/041291.
International Search Report dated Sep. 4, 2019 in connection with PCT/US19/37978.
International Search Report dated Sep. 10, 2019 in connection with PCT/US19/40964.
Written Opinion dated Sep. 17, 2018 in connection with PCT/US2018/041291.
Written Opinion dated Sep. 4, 2019 in connection with PCT/US19/37978.
Written Opinion dated Sep. 10, 2019 in connection with PCT/US19/40964.
Holmgaard et al., 2018, "Targeting the TGFβ pathway with galunisertib, a TGFβRI small molecule inhibitor, promotes anti-tumor immunity leading to durable, complete responses,as monotherapy and in combination with checkpoint blockade," Journal for ImmunoTherapy of Cancer 6:47.

* cited by examiner

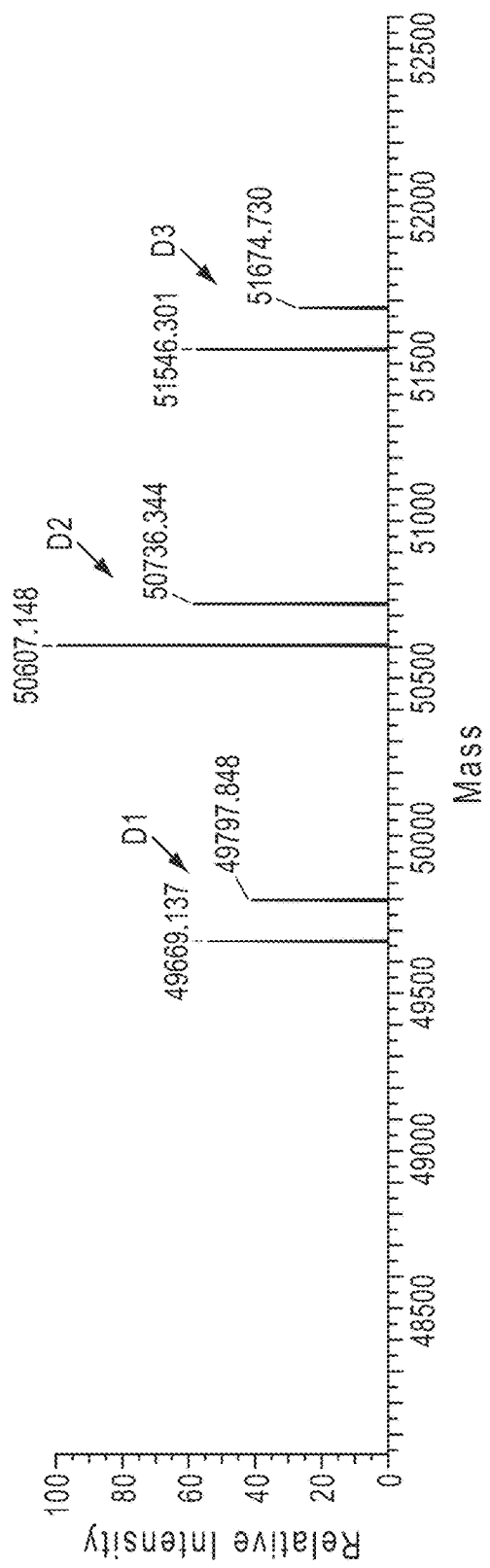
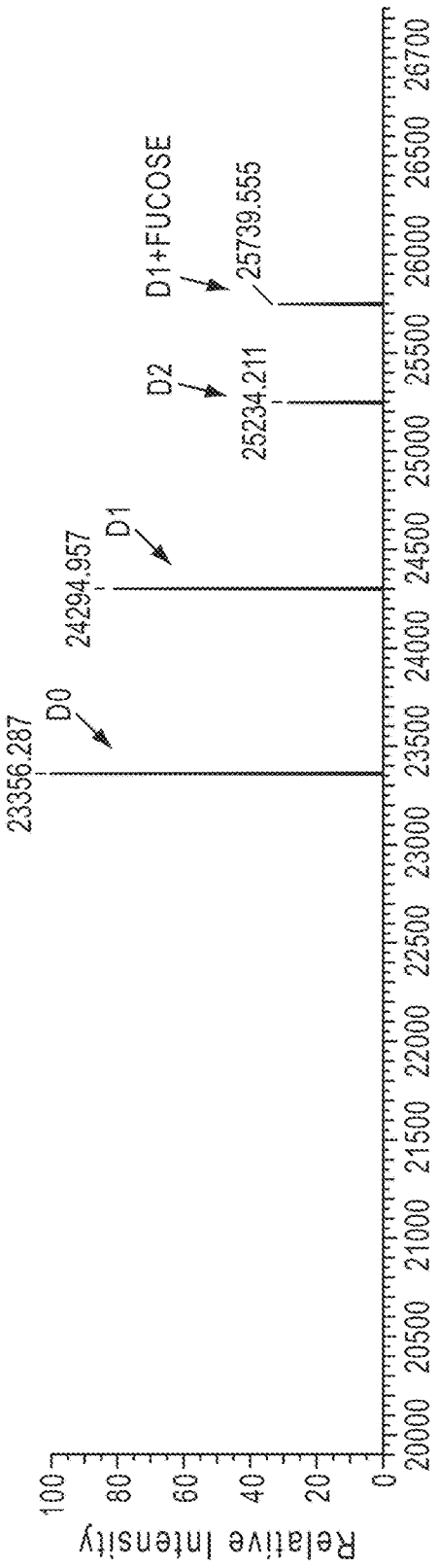
FIG. 7A
FIG. 7B

ANTIBODY-ALK5 INHIBITOR CONJUGATES AND THEIR USES

1. CROSS-REFERENCE TO RELATED APPLICATIONS

This application is a continuation of U.S. application Ser. No. 16/286,122, filed Feb. 26, 2019, now abandoned, which is a continuation of U.S. application Ser. No. 16/029,351, filed Jul. 6, 2018, now abandoned, which is a continuation of U.S. application Ser. No. 15/404,233, filed Jan. 12, 2017, now abandoned, which claims the priority benefit of U.S. provisional application No. 62/278,928, filed Jan. 14, 2016, the contents of which are incorporated herein in their entireties by reference thereto.

2. BACKGROUND

Members of the transforming growth factor-beta (TGF-β) family of cytokines are multifunctional proteins that regulate a diverse number of biological processes, both during normal tissue development as well as in disease states. TGF-β family members are involved in inflammation, wound healing, extracellular matrix accumulation, bone formation, tissue development, cellular differentiation, cardiac valve remodeling, tissue fibrosis and tumor progression, among others. (Barnard et al., 1990, Biochim Biophys Acta. 1032: 79-87; Sporn et al., 1992, J Cell Biol 119:1017-1021; Yingling et al., 2004, Nature Reviews, 3:1011-1022; Janssens et al., 2005, Endocr Rev., 26(6):743-74). Three mammalian isoforms have been identified to date: TGF-β1, TGF-β2, and TGF-β3. (Massague, 1990, Annu Rev Cell Biol 6:597-641). Other members of the transforming growth factor superfamily include activins, inhibins, bone morphogenetic proteins, growth and differentiation factors, and Müllerian inhibiting substance.

TGF-β I transduces signals through two highly conserved single transmembrane serine/threonine kinase receptors, the type I (ALK5) and type II TGF-β receptors. Upon ligand-induced binding and oligomerization, the type II receptor phosphorylates serine/threonine residues in the GS region of ALK5, which leads to ALK5 activation and generation of a novel SMAD docking site. The SMADS are intracellular proteins that specialize in transducing TGF-β's signal from the extracellular milieu into the cell's nucleus. Once activated, ALK5 phosphorylates Smad2 and Smad3 at their C-terminal SSXS-motif, thereby causing their dissociation from the receptor and complex formation with Smad4. Smad complexes then translocate into the nucleus, assemble with cell specific DNA-binding co-factors, to modify expression of genes that regulate cell growth, differentiation and development.

Activins transduce signals in a manner similar to TGF-β. Activins bind to serine/thereonine kinase, activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

TGF-β signaling is essential for maintaining immune homeostasis by regulating both innate and adaptive immune cells, including T and B lymphocytes, NK cells, and antigen presenting cells, such as dendritic cells. TGF-β is generally considered an immuno-suppressive cytokine, playing essential roles in T cell development in the thymus as well as in maintaining peripheral tolerance. TGF-β inhibits both CD4$^+$ and CD8$^+$ T cell proliferation, cytokine production, cytotoxicity and differentiation into T helper subsets (Li et al., 2008, Cell 134:392-404). TGF-β also has a prominent role in the development of natural regulatory T cells (nTregs) that arise from the thymus and in inducible Tregs (iTregs) that develop in the periphery in response to inflammation and various diseases, such as cancer (Tran et al., 2012, J Mol Cell Bio 4:29-37, 2012). nTregs are a small proportion of the CD4+ T cell subset that are typically CD25+ FoxP3+ and actively suppress T cell activation to help maintain peripheral T cell tolerance. TGF-β is critical for nT$_{reg}$ survival and expansion in the periphery (Marie et al., 2005, J Exp Med 201:1061-67). Under the appropriate inflammatory conditions, TGF-β converts naive CD4$^+$ T cells into FoxP3+ $^{iT}$$_{regs}$ to suppress local, tissue resident T cells. Increased levels of iT$_{regs}$ are often found within the tumor itself to prevent T cell-mediated tumor clearance (Whiteside, 2014, Expert Opin Biol Ther 14:1411-25).

In general, high levels of TGF-β expression has been linked to worse clinical prognosis. Oftentimes, tumors co-opt the TGF-β pathway and utilize it to avoid T cell-mediated tumor clearance (Yang et al., Trends Immunol 31:220-7, 2010; Tu et al., Cytokine Growth Factor Rev 25:423-35, 2014). This occurs in two ways. One, TGF-β directly inhibits CD4+ and CD8+ T cell expansion, cytokine production and tumor cell killing. Second, TGF-β is critical for the survival and/or conversion of nT$_{regs}$ and iT$_{regs}$ respectively, which also suppress immune-mediated tumor clearance. In multiple preclinical mouse models, neutralization of TGF-β has demonstrated reduced tumor burdens due to increased T cell mediated tumor clearance. Importantly, inhibition of TGF-β signaling in T cells via expression of dominant negative TGF-βR11 or with soluble TGF-β receptors is sufficient to restore effective immune-mediated tumor clearance in vivo. Gorelik et al., 2001, Nat Med 7:1118-22; Thomas et al., 2005, Cancer Cell 8:369-80.

Aside from its effects on the immune system, TGF-β signaling has a prominent but complex role in tumor development. Preclinical studies indicate that TGF-β has paradoxical effects on the tumor itself and confounding effects on the surrounding stromal cells. In early stages of cancer progression, TGF-β inhibits tumor growth and expansion via regulation of cell cycle mediators. However, at later stages, TGF-β loses its growth inhibitory properties and promotes tumor metastases via induction of epithelial to mesenchymal transition (EMT) and via its effects on stromal fibroblasts, angiogenesis and extra cellular matrix (ECM) (Connolly et al., 2012, Int J Bio 8:964-78). If delivered at the wrong stage, broad spectrum inhibition of TGF-β signaling runs the risk of promoting tumor metastases, and/or inhibiting non-tumor, stromal cell populations that indirectly exacerbate tumor progression (Cui et al., 1996, Cell 86:531-; Siegel et al., 2003, PNAS 100:8430-35; Connolly et al., 2011, Cancer Res 71:2339-49; Achyut et al., 2013, PLOS Genetics 9:1-15). TGF-β inhibitors could drive tumors to become more aggressive and metastasize, instead of the intended effect of growth inhibition.

Despite the paradoxical effects on the tumor itself and broad expression of TGF-β receptors, inhibition of the TGF-β pathway as a cancer therapy has long been of interest. Inhibitors have included neutralizing TGF-β antibodies, TGF-β2 antisense RNA and small molecule ATP-competitive, ALK5 kinase inhibitors. Some of the classical ALK5 inhibitors that have been developed are pyrazole-based, imidazole-based and triazole-based (Bonafoux et al., 2009, Expert Opin Ther Patents 19:1759-69; Ling et al., 2011, Current Pharma Biotech 12:2190-2202). Many ALK5 inhibitors have been tested in both in vitro cell based assays as well as in in vivo mouse xenograft and syngeneic tumor models and have demonstrated significant efficacy (Neuzillet et al., 2015, Pharm & Therapeutics 147:22-31). However, due to concerns of host toxicity since TGF-β receptors are ubiquitously expressed and fears of inadvertently promoting tumor growth, most of the TGF-β inhibitors, especially the ALK5 inhibitors, have remained in preclinical discovery stages. For instance, in preclinical toxicology studies in rats, two different series of ALK5 inhibitors demonstrated heart valve lesions characterized by hemorrhage, inflammation, degeneration, and proliferation of valvular interstitial cells (Anderton et al., 2011, Tox Path 39:916-24).

Accordingly, there is a need to target ALK5 inhibitors to cell types in which the inhibition of TGF-β signaling is therapeutically useful, while minimizing host tissue toxicity such as those observed in cardiac tissue.

3. SUMMARY

To avoid on-target, host toxicity as well as prevent inadvertent exacerbation of tumor progression due to ALK5 inhibitor therapy, the inventor developed a novel approach to direct the compounds to only those cells in which it would confer a therapeutic benefit.

For treatment of cancer, the approach encompasses directing the ALK5 inhibitor to the T cell compartment via an antibody to promote T cell mediated tumor clearance and establish long term remission without causing systemic toxicity. Without being bound by theory, it is believed that not only would inhibition of TGF-β signaling in T cells directly enhance T cell-mediated clearance, but it would also inhibit conversion of T cells into inducible $T_{regs}$ and decrease natural $T_{reg}$ viability in the tumor. Thus, inhibition of TGF-β signaling in T cells not only restores CD4$^+$ and CD$_8^+$ T cell activity, but also removes the $T_{reg}$ "brake" on T cells to effectively re-engage the immune system. More importantly, inhibition of TGF-β signaling solely in T cells will be safer than broad spectrum TGF-β inhibition, both from the tumor perspective as well as host tissue toxicity.

Accordingly, the present disclosure provides antibody-drug conjugates (ADCs) in which the drug is an ALK5 inhibitor. The antibody component of the ADCs can be an antibody or antigen binding fragment that binds to a T cell surface molecule. Section 5.2 describes exemplary antibody components that can be used in the ADCs of the disclosure. In some embodiments, the ALK5 inhibitor is an imidazole-benzodioxol compound, an imidazole-quinoxaline compound, a pyrazole-pyrrolo compound, or a thiazole type compound. Exemplary ALK5 inhibitors are described in Section 5.3 and Tables 1-3.

The ALK5 inhibitor can be directly conjugated to the antibody component or linked to the antibody component by a linker. The linker can be a non-cleavable linker or, preferably, a cleavable linker. Exemplary non-cleavable and cleavable linkers are described in Section 5.4. The average number of ALK5 inhibitor molecules attached per antibody or antigen binding fragment can vary, and generally ranges from 2 to 8 ALK5 inhibitor molecules per antibody or antigen binding fragment. Drug loading is described in detail in Section 5.5.

The present disclosure further provides pharmaceutical compositions comprising an ADC of the disclosure. Exemplary pharmaceutical excipients that can be used to formulate a pharmaceutical composition comprising an ADC of the disclosure are described in Section 5.6.

The present disclosure further provides methods of treating a cancer by administering an ADC of the disclosure or a pharmaceutical composition of the disclosure to a subject in need thereof. The ADCs and pharmaceutical compositions of the disclosure can be administered as monotherapy or as part of a combination therapy. Exemplary cancers that can be treated with the ADCs and pharmaceutical compositions of the disclosure and exemplary combination therapies are described in Section 5.7.

4. BRIEF DESCRIPTION OF THE FIGURES

FIG. 1 illustrates the effect of TGF-β on CD4+ and CD8$^+$ T cells. During tumor progression, TGF-β, which can be derived from both the tumor and the T cells themselves, inhibits CD4$^+$ T cell functions, such as cytokine production, proliferation and Th differentiation. In parallel, TGF-β also inhibits expression of granzymes and perforin in cytotoxic CD8$^+$ T cells, thereby inhibiting tumor killing. Inhibiting both CD4+ and CD8+ T cells populations profoundly suppresses T cell-mediated tumor clearance.

FIG. 2 illustrates the effect of TGF-β on $T_{reg}$ cells during tumor progression. During tumor progression, $nT_{reg}$ and $iT_{reg}$ cells are typically found within the tumor to control T cell mediated functions in situ. TGF-β promotes $nT_{reg}$ cell viability and conversion of $iT_{reg}$ cells to suppress T cell-mediated tumor clearance. An increase of $T_{reg}$ cells at the tumor site ensures that T cells that do infiltrate the tumor are also prevented from clearing the tumor.

Figure 1:
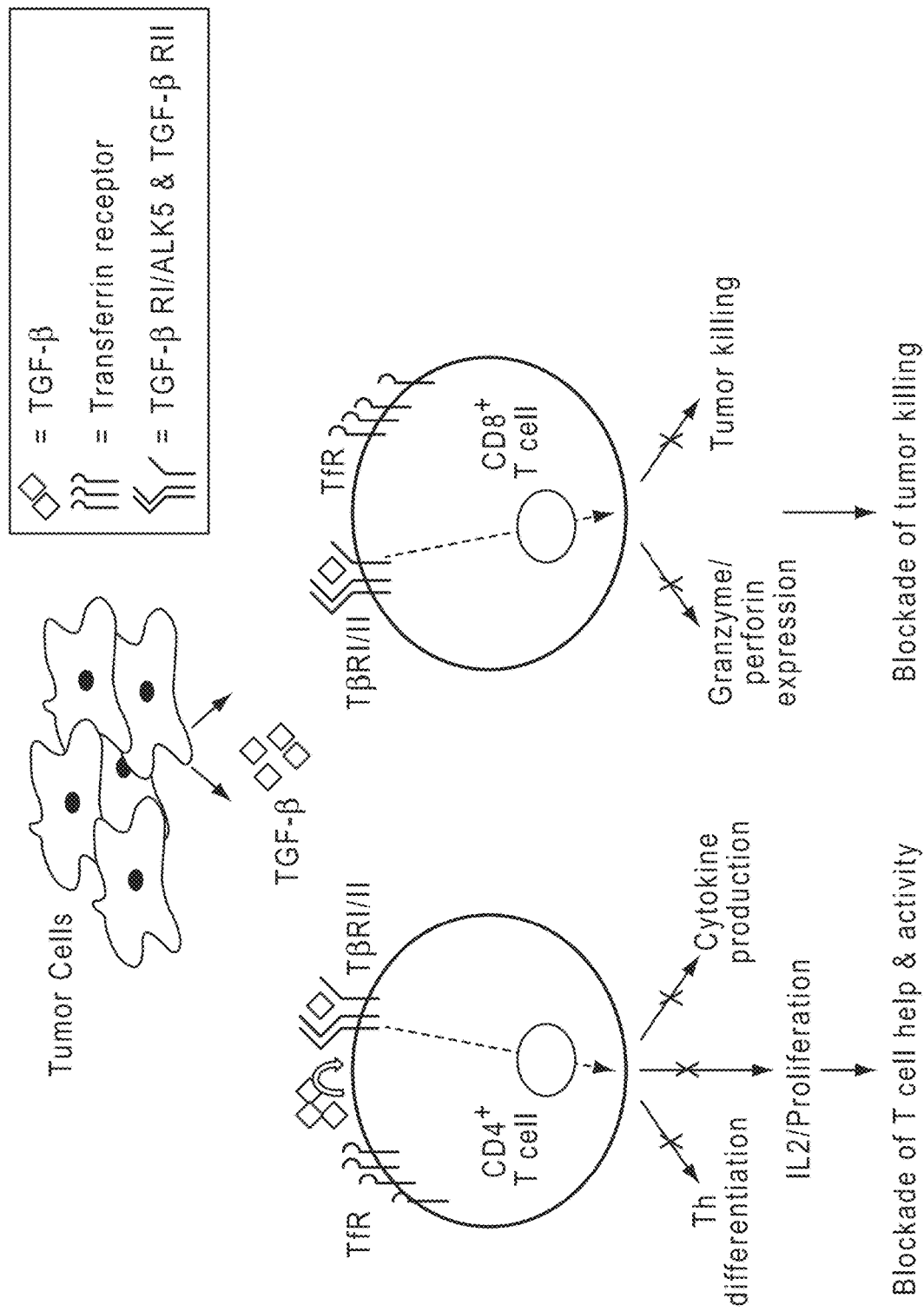
Figure 2:
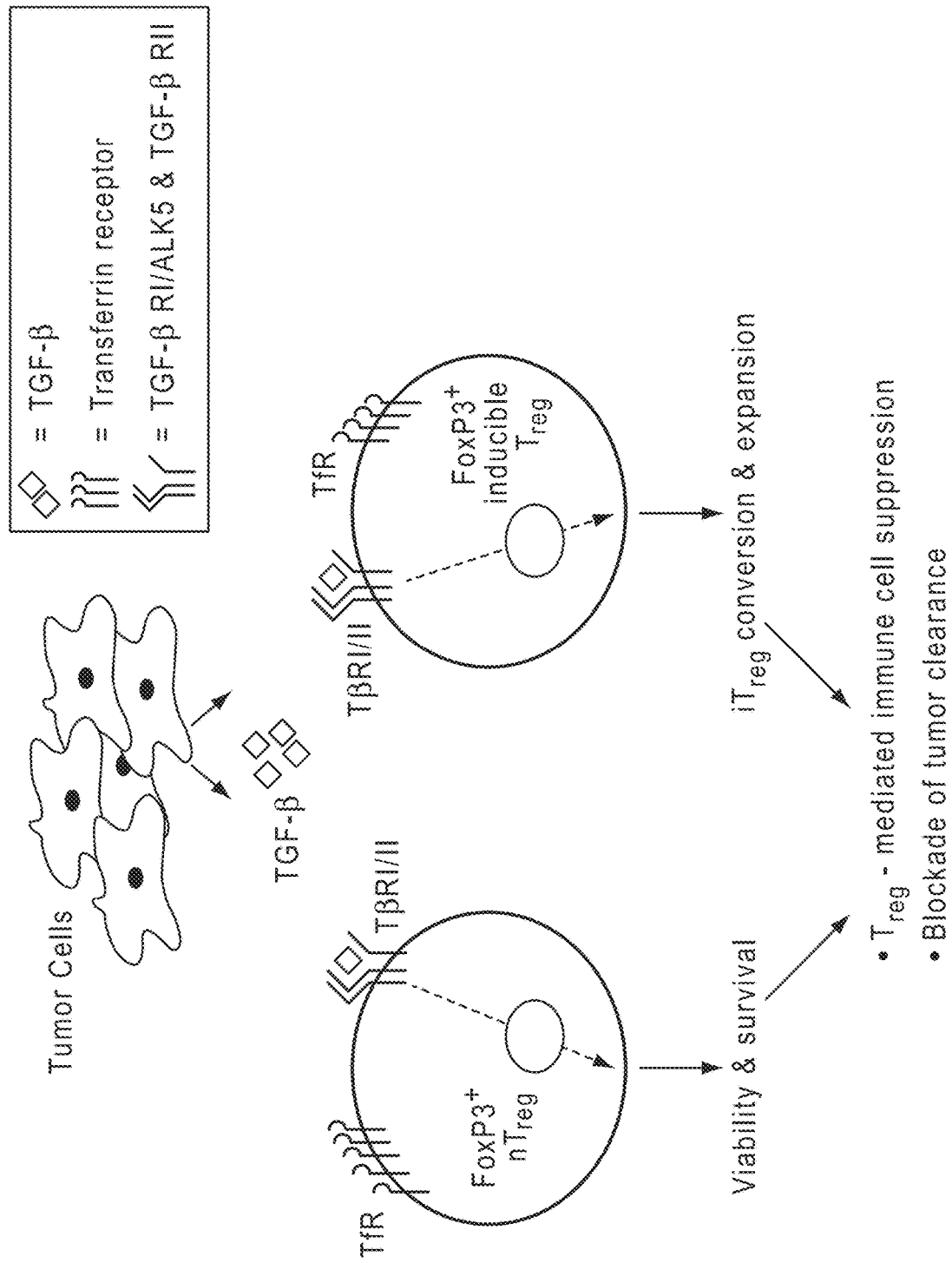
Figure 3:
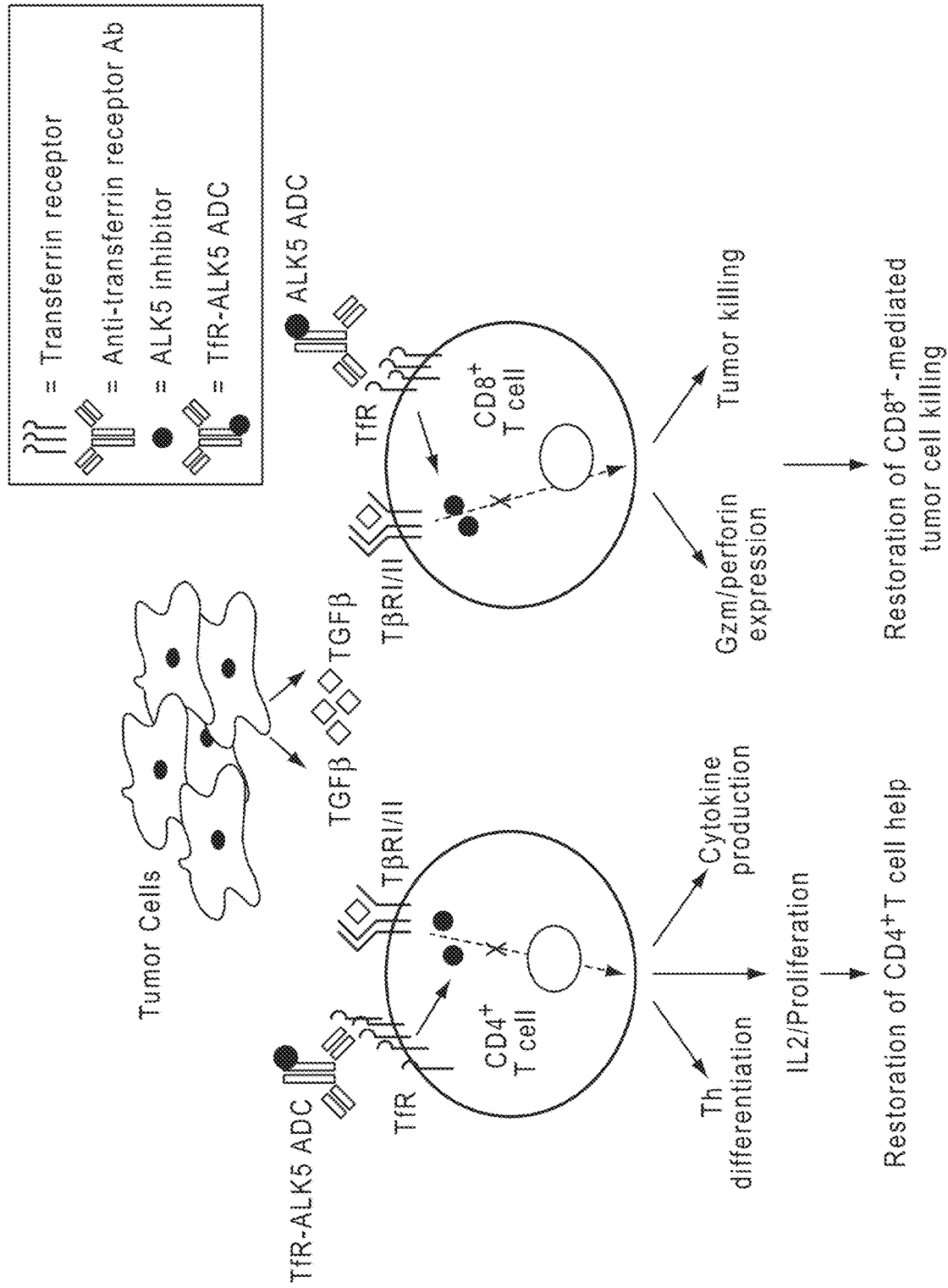
FIG. 3 illustrates the mechanism of action of the ADCs of the disclosure on CD4$^+$ and CD8$^+$ T cells. T cell targeted inhibition of TGF-β signaling restores CD4$^+$ T cell activity and CD8$^+$ T cell mediated tumor killing.
Figure 4:
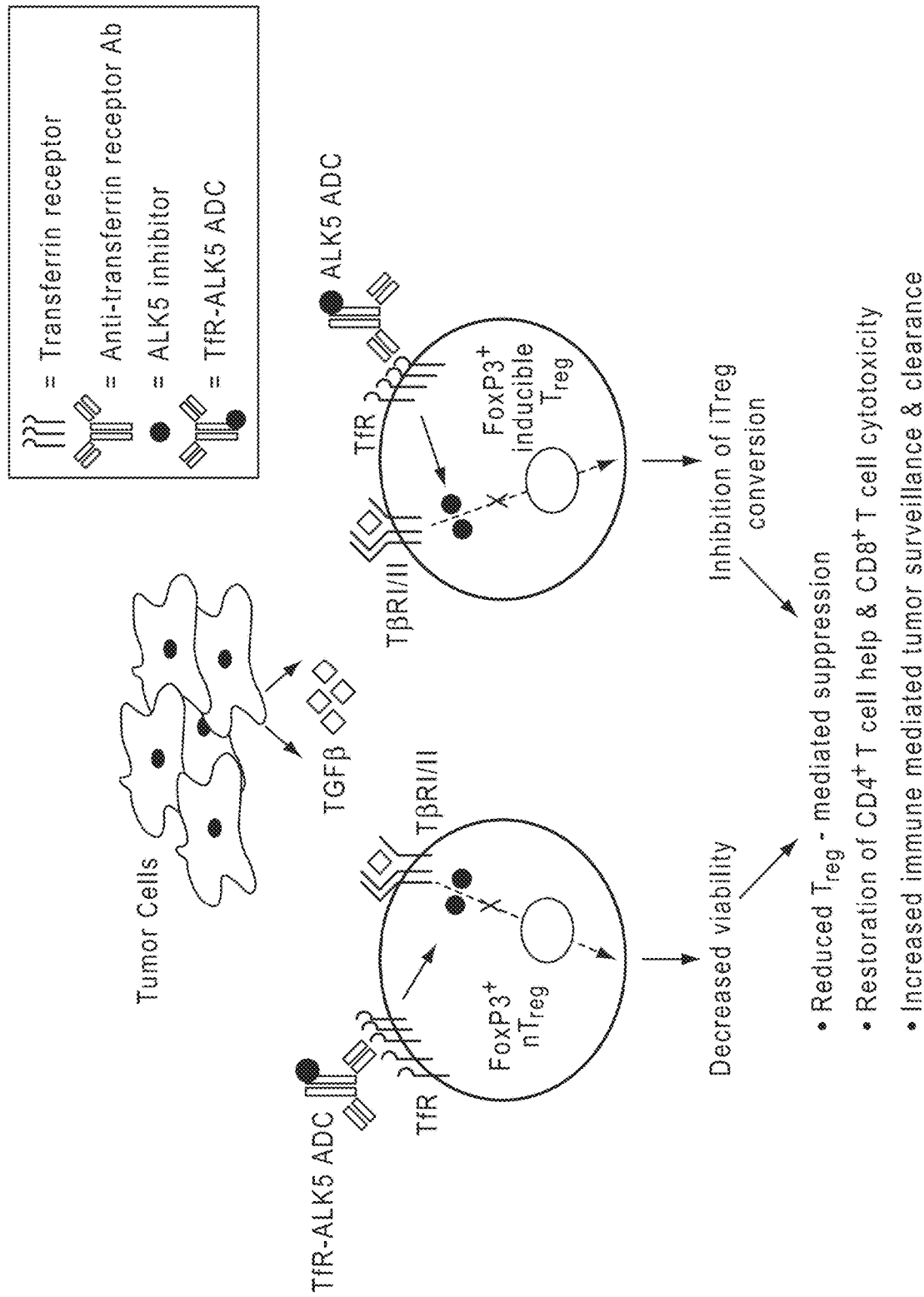
FIG. 4 illustrates the mechanism of action of the ADCs of the disclosure on $T_{reg}$ cells. T cell targeted inhibition of TGF-β signaling also blocks $T_{reg}$-mediated suppression of immune-mediated tumor clearance in situ.
Figure 5A:
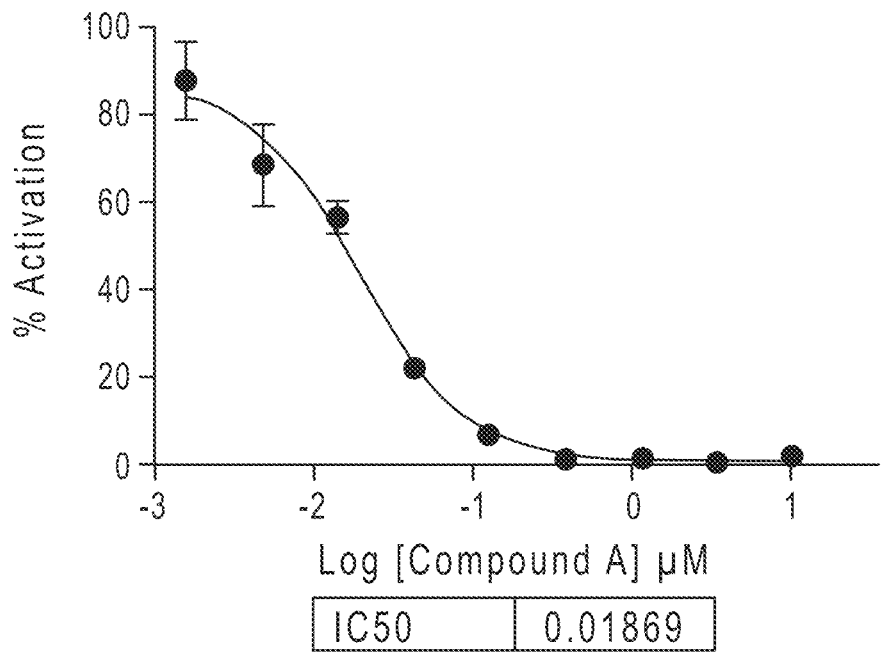
Figure 5B:
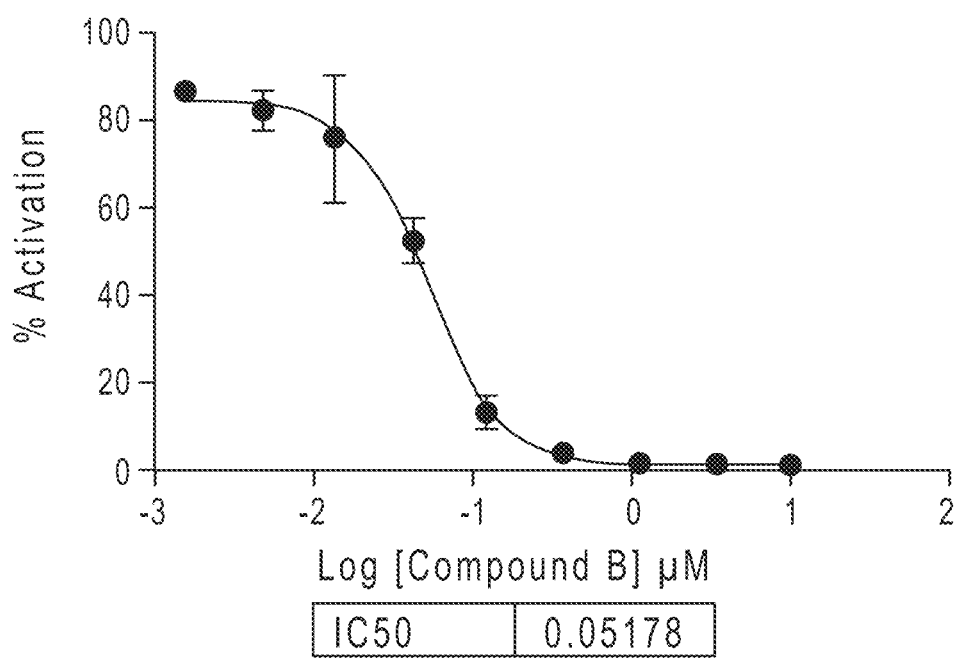
Figure 5C:
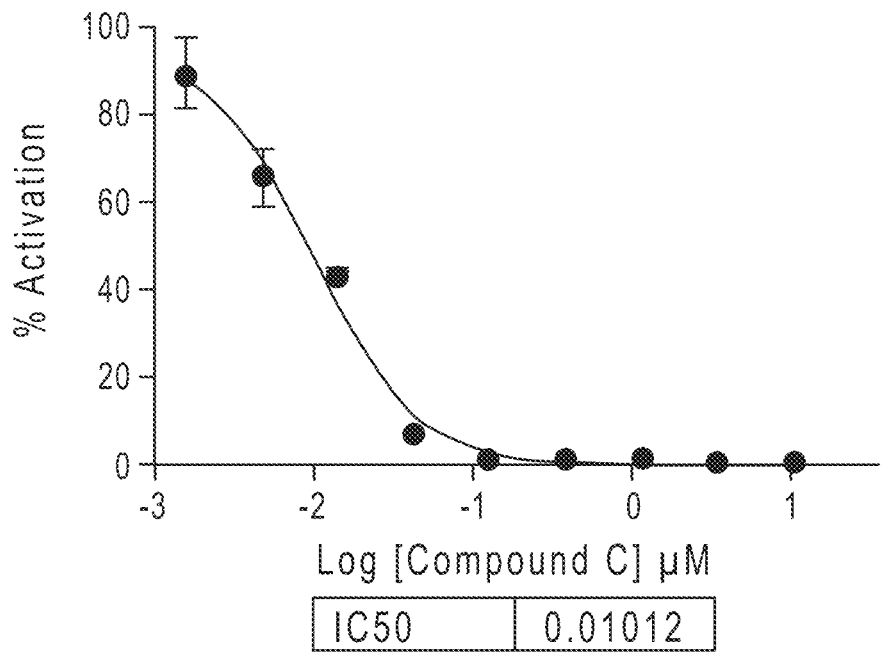
Figure 5D:
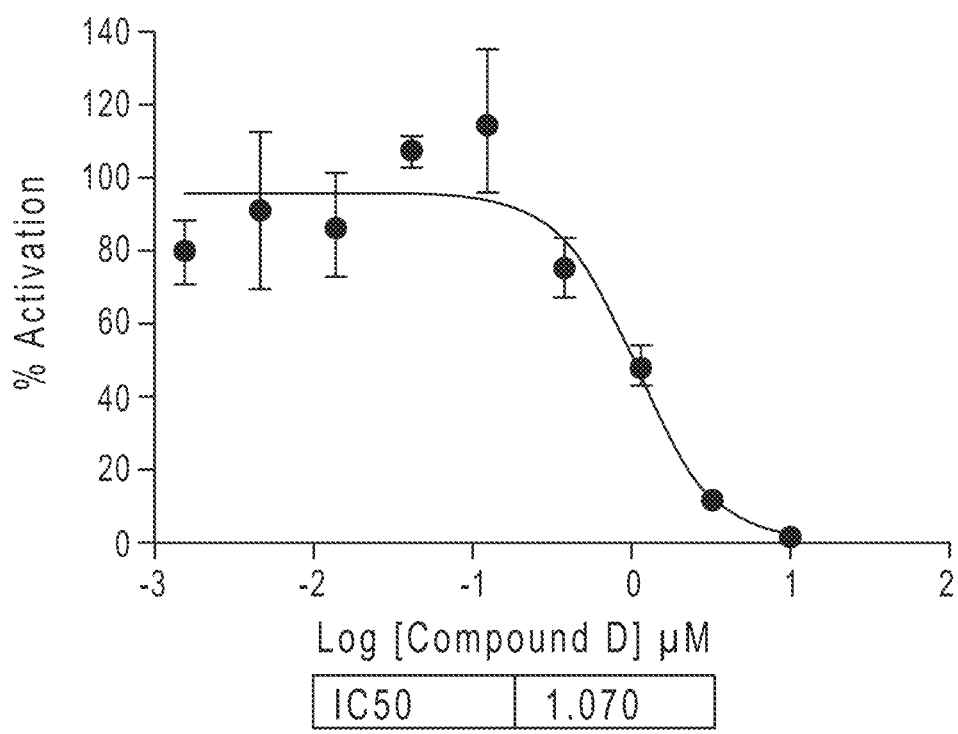

FIG. 5A-5D show inhibition of TGF-β-induced luciferase activity in HEK293T cells by Compounds A-D. FIG. 5A: Compound A; FIG. 5B: Compound B; FIG. 5C: Compound C; FIG. 5D: Compound D.

Figure 6A:
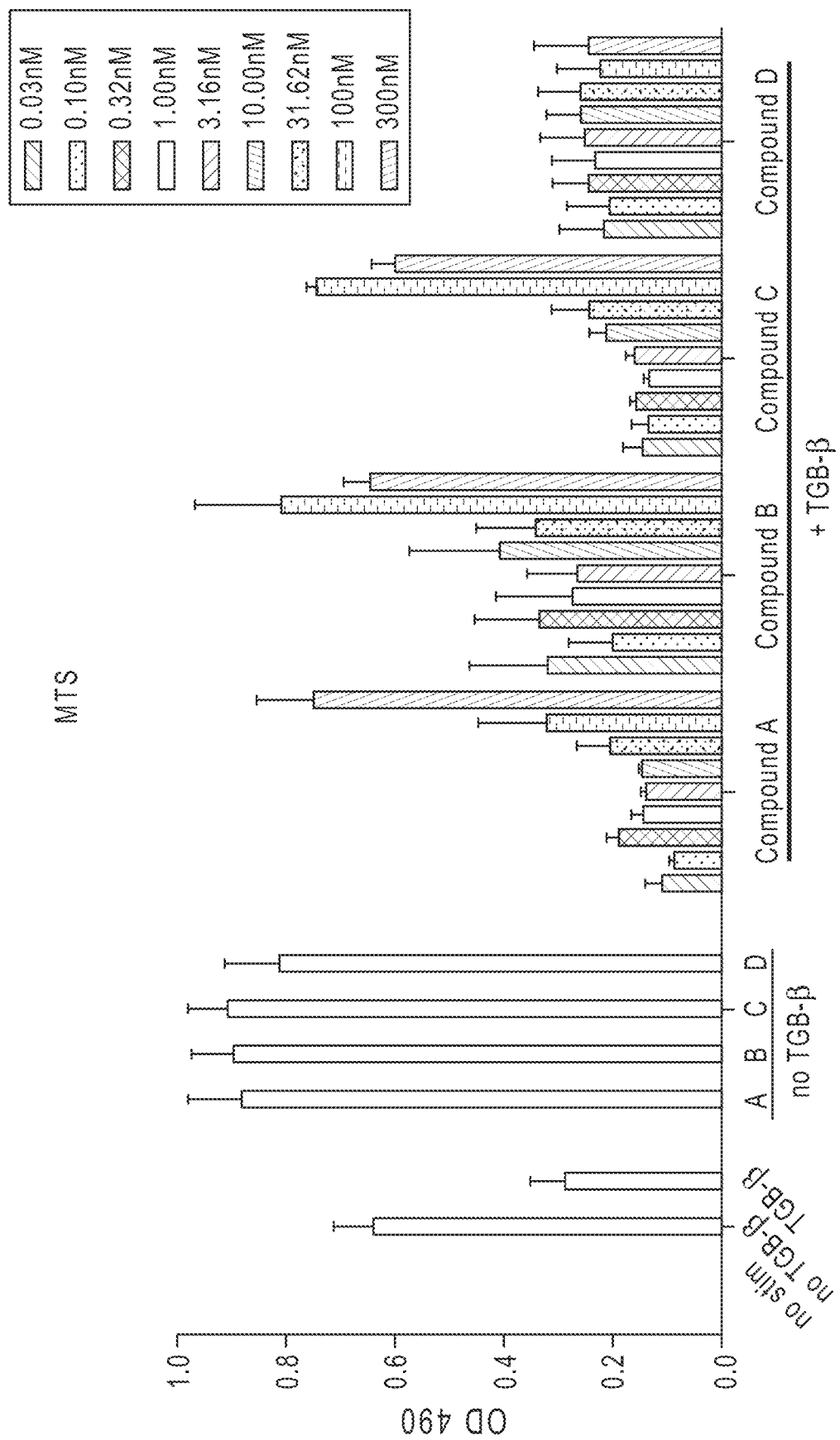
Figure 6B:
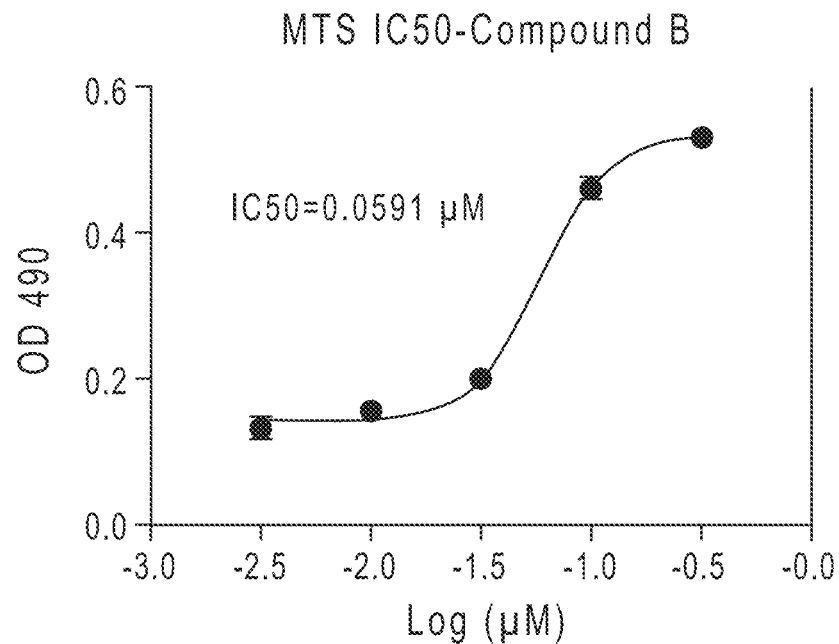
Figure 6C:
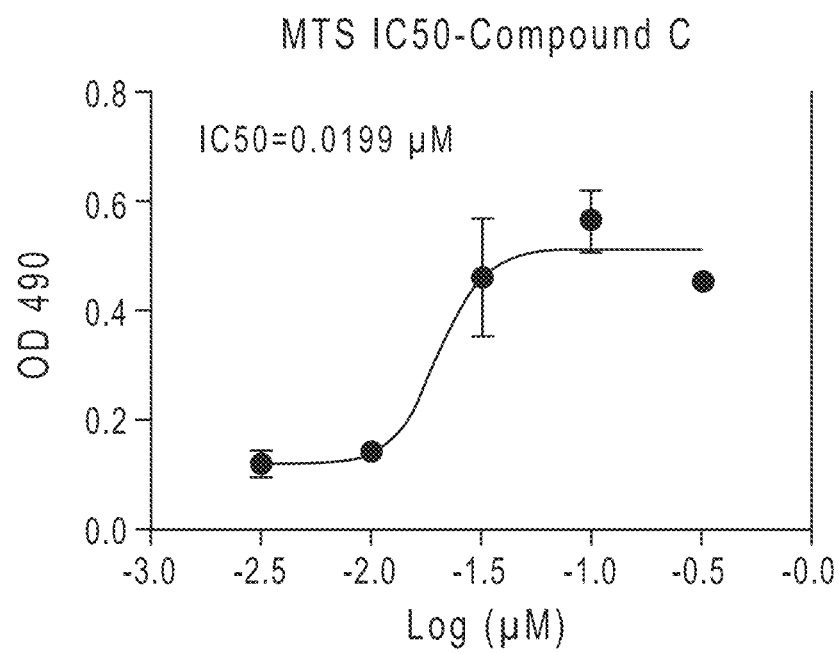

FIG. 6A-6C show MTS proliferation assay data for Compounds A-D. Compounds A-C restore proliferation in TGF-b treated CDC4+ T cells. FIG. 6A: data for Compounds A-D. In FIG. 6A, the bars labeled "A," "B," "C", and "D" above "no TGF-β" show the results of experiments performed using the compounds at 100 nM and without TGF-β. FIG. 6B: data for Compound B; FIG. 6C: data for Compound C.

FIG. 7A-7B shows LC-MS data for an exemplary ADC of the disclosure (ADC2). FIG. 7A: LC-MS data for the ADC heavy chain; FIG. 7B: LC-MS data for the ADC light chain.

Figure 8:
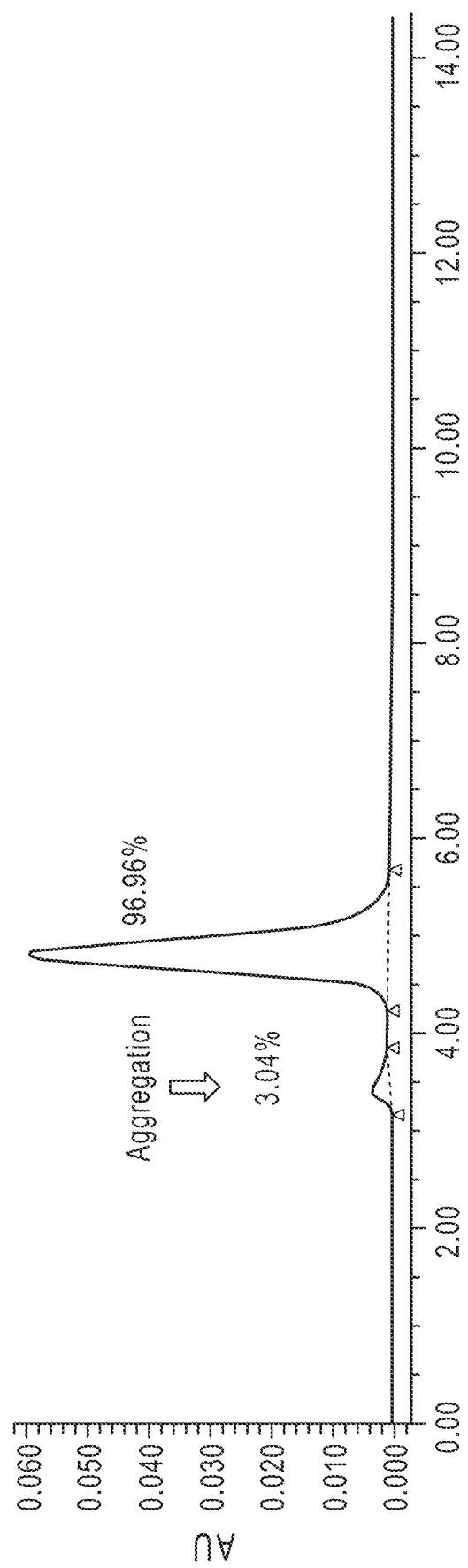

FIG. 8 is a chromatogram of ADC2 prepared with a S-4FB/Ab ratio of 6 purified by SEC. SEC analysis of the purified ADC2 shows that aggregation is below 5%.

Figure 9A:
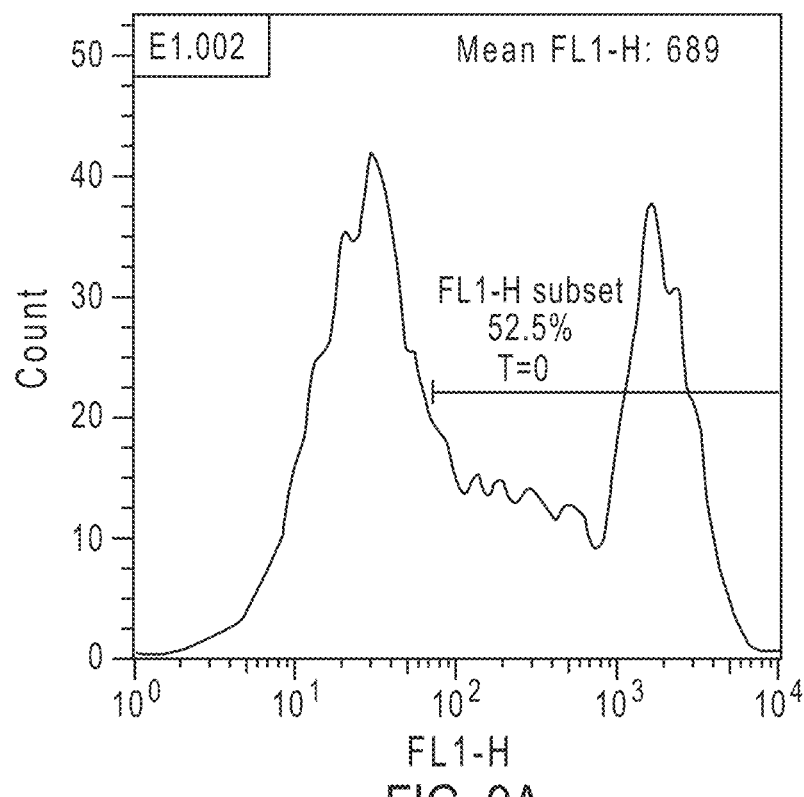
Figure 9B:
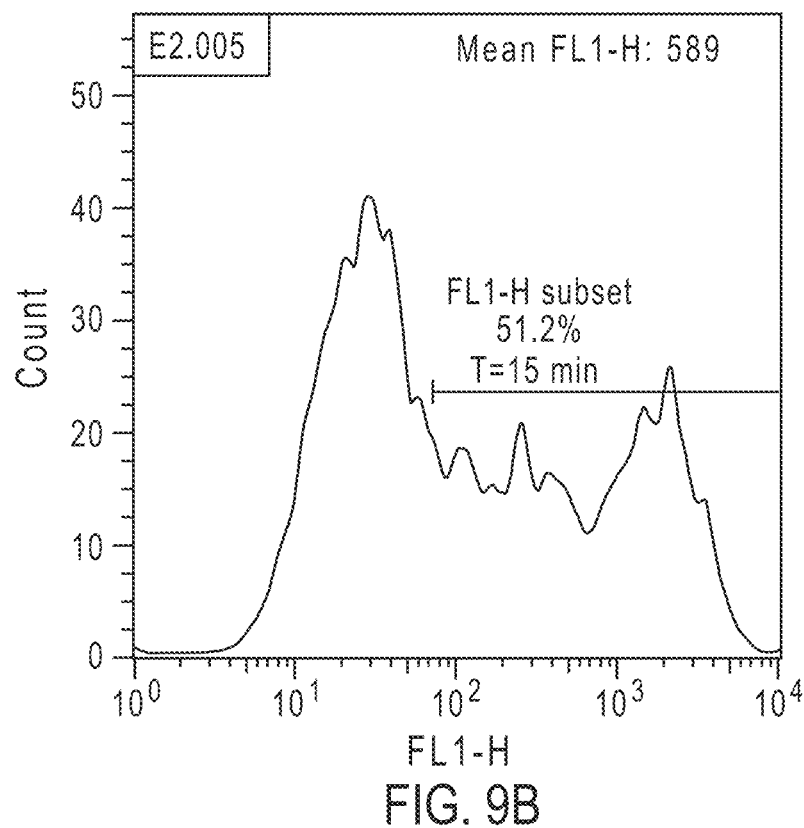
Figure 9C:
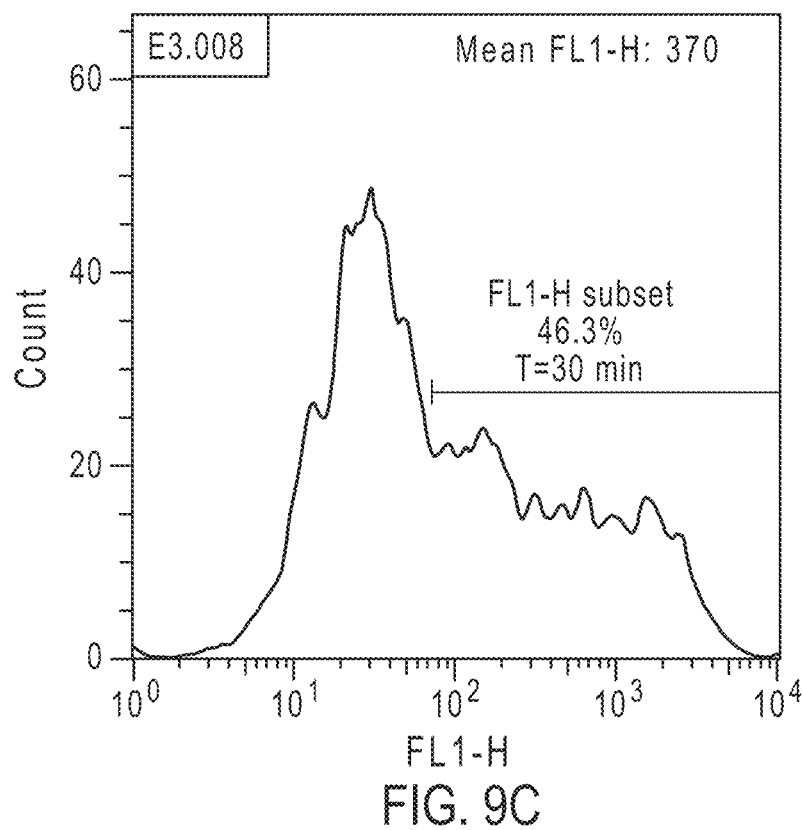
Figure 9D:
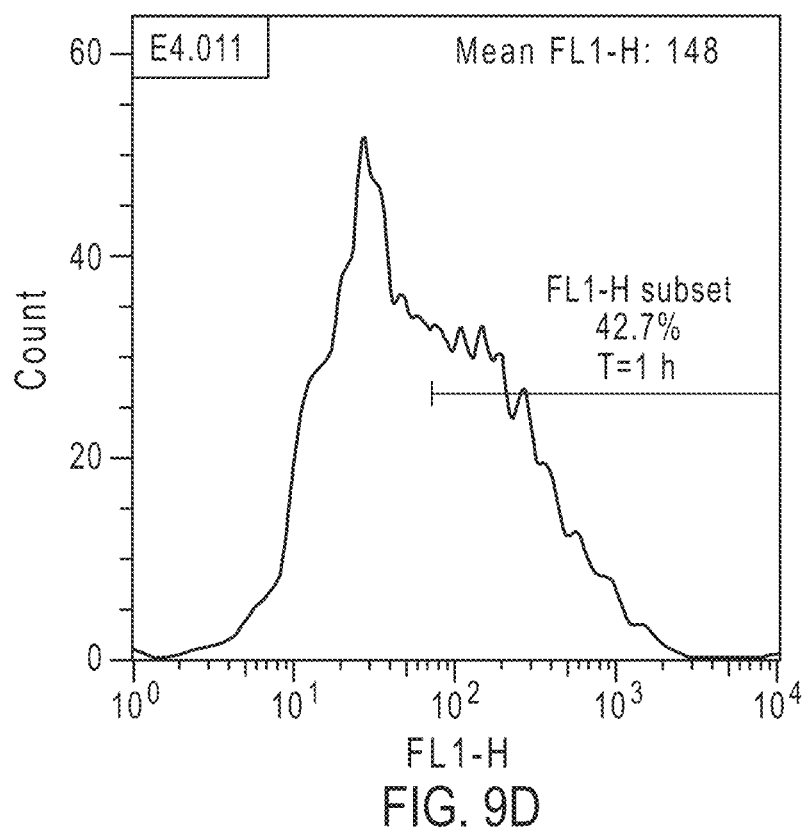
Figure 9E:
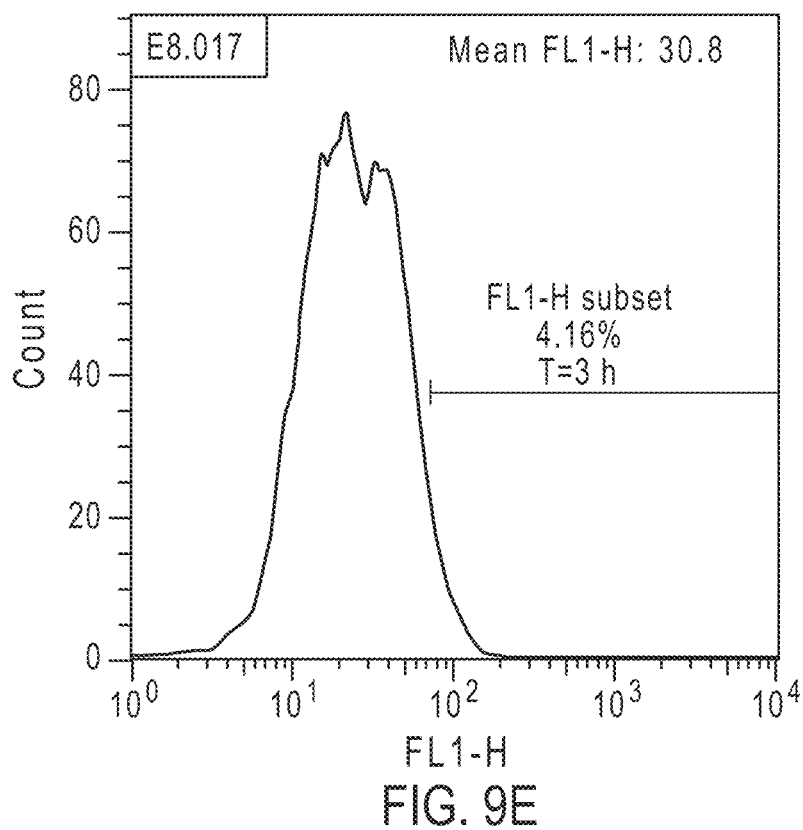
Figure 9F:
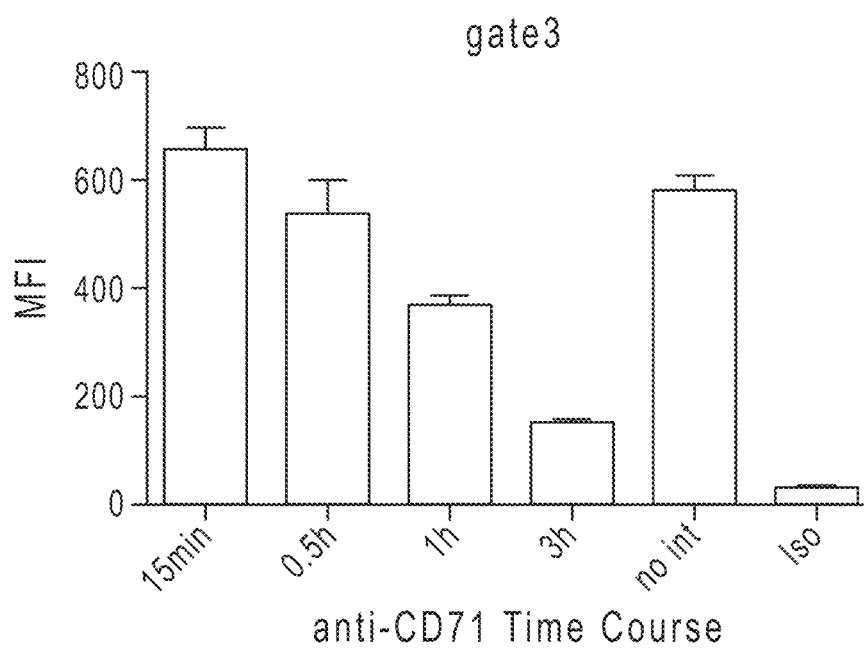

FIG. 9A-9F shows that an exemplary antibody of the disclosure (anti-transferrin receptor antibody R17217) induces internalization of the antibody's target, the transferrin receptor (TfR), on primary mouse CD4$^+$ T cells. FIG. 9A: control with no anti-transferrin receptor antibody; FIG. 9B: 15 minute incubation with anti-transferrin receptor antibody; FIG. 9C: 30 minute incubation with anti-transferrin receptor antibody; FIG. 9D: 60 minute incubation with anti-transferrin receptor antibody; FIG. 9E: 180 minute incubation with anti-transferrin receptor antibody; FIG. 9F: mean fluorescence intensity (MFI) over a three hour time course.

Figure 10:
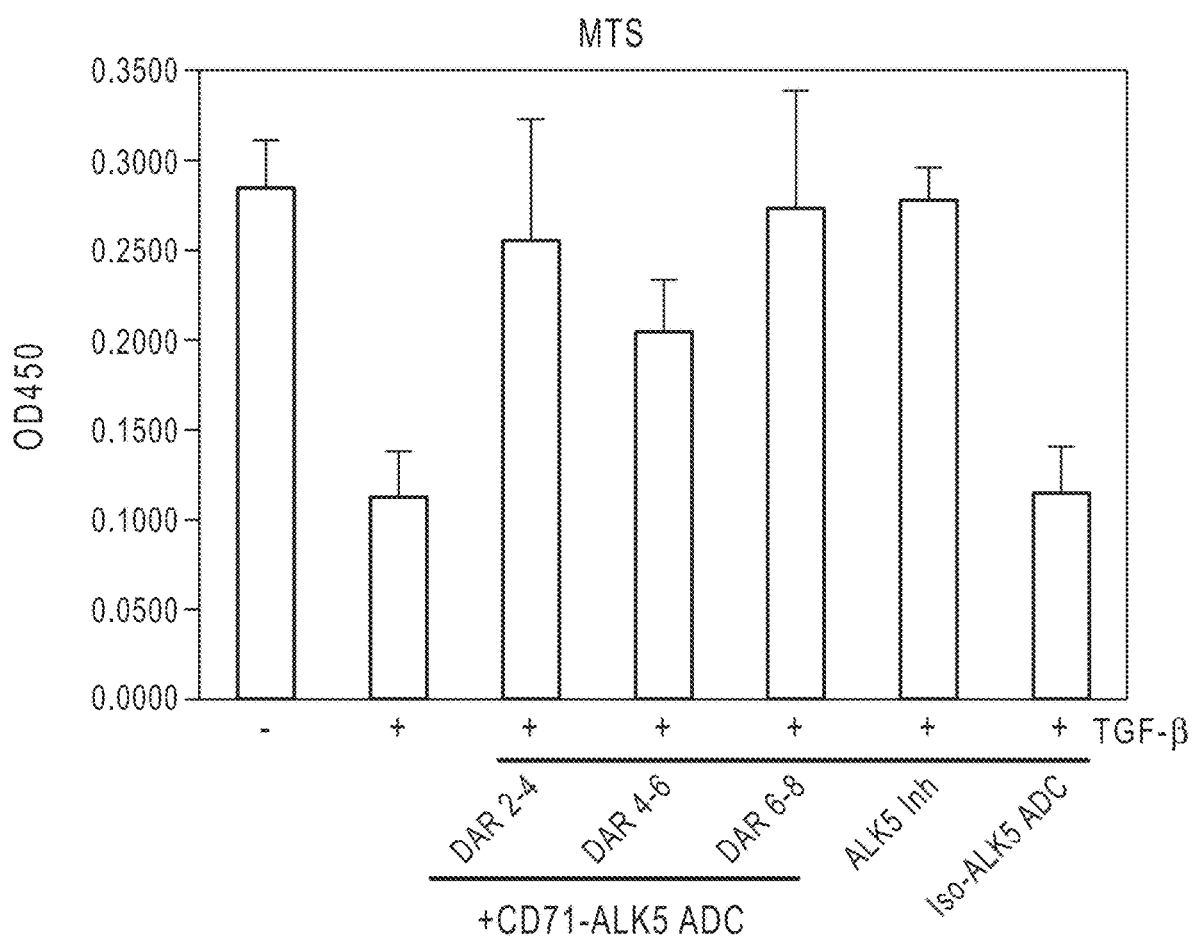

FIG. 10 shows reversal of TGF-β-mediated inhibition of proliferation in mouse CTLL2 cells by an exemplary ADC of the disclosure (ADC1).

Figure 11:
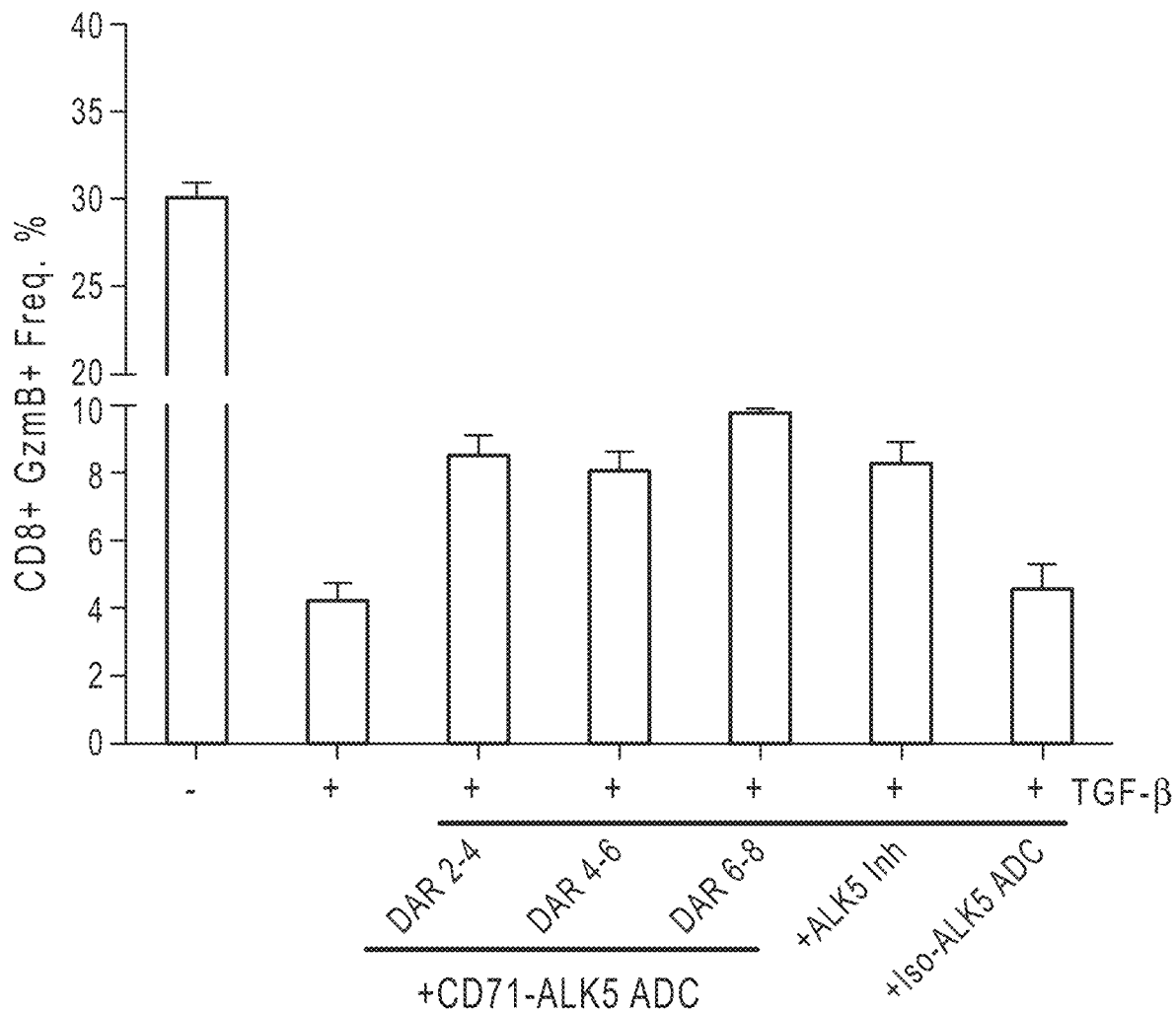

FIG. 11 shows de-repression of Granzyme B expression in TGF-β-activated primary CD8+ T cells by an exemplary ADC (ADC1) of the disclosure. ADC1 partially restores Granzyme B expression comparable to the free ALK5 inhibitor.

Figure 12:
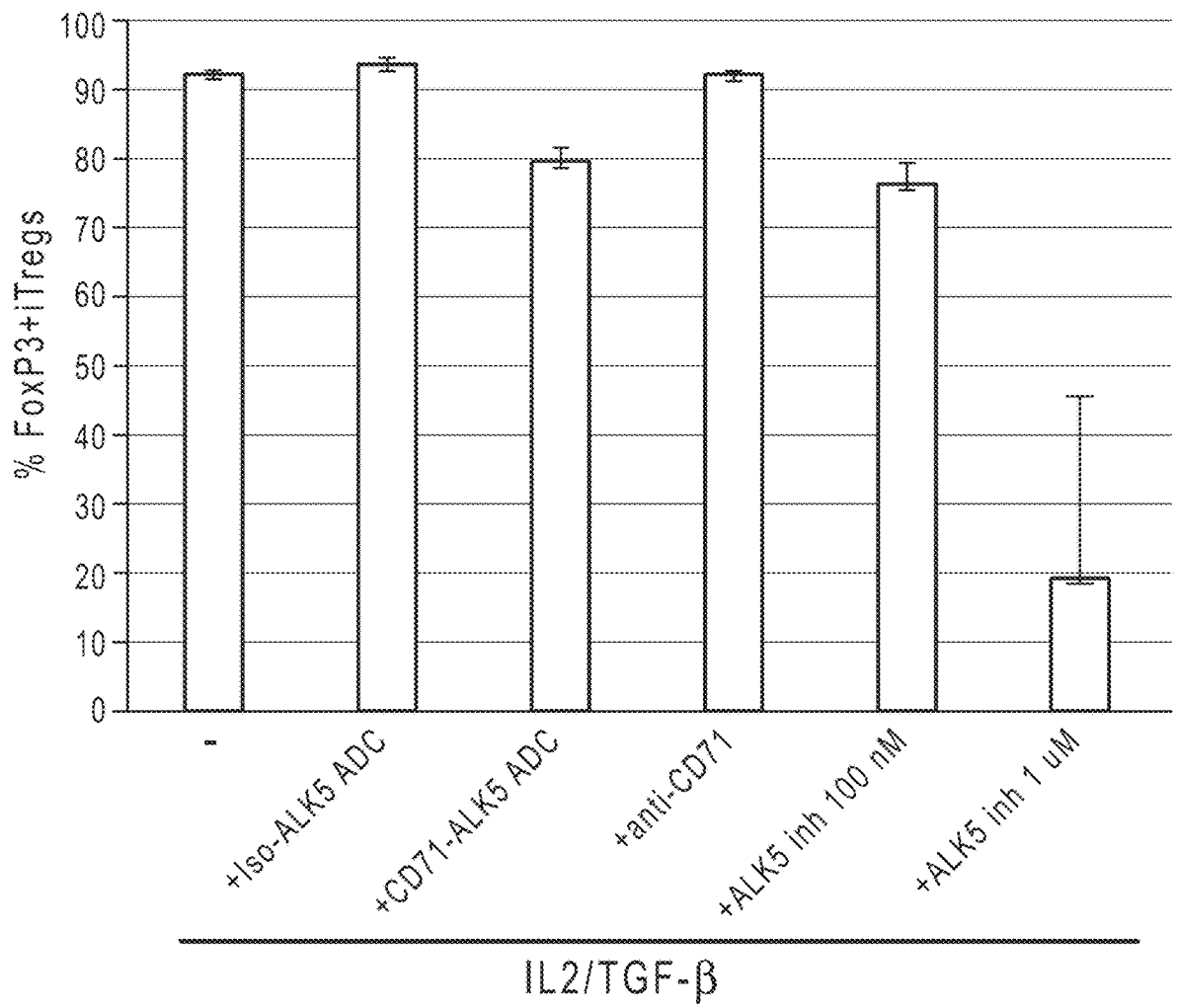

FIG. 12 shows that an exemplary ADC of the disclosure (ADC1) decreases iTreg generation, similar to 100 mM of free ALK5 inhibitor.

5. DETAILED DESCRIPTION

The disclosure provides antibody-drug conjugates (ADCs) useful for treating cancer comprising an antibody component covalently bonded to an ALK5 inhibitor, either directly or through a linker. An overview of the ADCs of the disclosure is presented in Section 5.1. The antibody component of the ADCs can be an intact antibody or a fragment thereof. Antibodies that can be used in the ADCs of the disclosure are described in detail in Section 5.2. ALK5 inhibitors that can be used in the ADCs of the disclosure are described in Section 5.3. The ADCs of the disclosure typically contain a linker between the antibody and ALK5 inhibitor. Exemplary linkers that can be used in ADCs of the disclosure are described in Section 5.4. The ADCs of the disclosure can contain varying numbers of ALK5 inhibitor moieties per antibody. Drug loading is discussed in detail in Section 5.5. The disclosure further provides pharmaceutical formulations comprising an ADC of the disclosure. Pharmaceutical formulations comprising ADCs are described in Section 5.6. The disclosure further provides methods of treating various cancers using the ADCs of the disclosure. Methods of using the ADCs of the disclosure as monotherapy or as part of a combination therapy for the treatment of cancer are described in Section 5.7.

5.1. Antibody Drug Conjugates

The ADCs of the disclosure are generally composed of an ALK5 inhibitor covalently attached to an antibody, typically via a linker, such that covalent attachment does not interfere with binding to the antibody's target.

Techniques for conjugating drugs to antibodies are well known in the art (See, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In one example, the antibody or fragment thereof is fused via a covalent bond (e.g., a peptide bond), through the antibody's N-terminus or the C-terminus or internally, to an amino acid sequence of another protein (or portion thereof; for example, at least a 10, 20 or 50 amino acid portion of the protein). The antibody, or fragment thereof, can linked to the other protein at the N-terminus of the constant domain of the antibody. Recombinant DNA procedures can be used to create such fusions, for example as described in WO 86/01533 and EP0392745. In another example the effector molecule can increase half-life in vivo, and/or enhance the delivery of an antibody across an epithelial barrier to the immune system. Examples of suitable effector molecules of this type include polymers, albumin, albumin binding proteins or albumin binding compounds such as those described in PCT publication no. WO 2005/117984.

The metabolic process or reaction may be an enzymatic process, such as proteolytic cleavage of a peptide linker of the ADC, or hydrolysis of a functional group such as a hydrazone, ester, or amide. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an antibody-drug conjugate (ADC) whereby the covalent attachment, i.e. linker, between the drug moiety (D) and the antibody (Ab) is broken, resulting in the free drug dissociated from the antibody inside the cell. The cleaved moieties of the ADC are thus intracellular metabolites.

5.2. The Antibody Component

The present disclosure provides antibodies drug conjugates in which the antibody component binds to a T cell surface molecule. Unless indicated otherwise, the term "antibody" (Ab) refers to an immunoglobulin molecule that specifically binds to, or is immunologically reactive with, a particular antigen, and includes polyclonal, monoclonal, genetically engineered and otherwise modified forms of antibodies, including but not limited to chimeric antibodies, humanized antibodies, heteroconjugate antibodies (e.g., bispecific antibodies, diabodies, triabodies, and tetrabodies), and antigen binding fragments of antibodies, including, e.g., Fab', F(ab')$_2$, Fab, Fv, rIgG, and scFv fragments. Moreover, unless otherwise indicated, the term "monoclonal antibody" (mAb) is meant to include both intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue binding than an intact antibody (Wahl et al., 1983, J. Nucl. Med. 24:316).

The term "scFv" refers to a single chain Fv antibody in which the variable domains of the heavy chain and the light chain from a traditional antibody have been joined to form one chain.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab. Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 Daltons, composed of two identical light (L) chains and two identical heavy (H) chains. Each heavy chain has at the amino terminus a variable domain (VH) followed by a number of constant domains. Each light chain has a variable domain at the amino terminus (VL) and a constant domain at the carboxy terminus.

For optimal delivery of the ALK5 inhibitor within a cell, the antibodies are preferably internalizing. Internalizing antibodies, after binding to their target molecules on cellular surface, are internalized by the cells as a result of the binding. The effect of this is that the ADC is taken up by cells. Processes which allow the determination of the internalization of an antibody after binding to its antigen are known to the skilled person and are described for example on page 80 of PCT publication no. WO 2007/070538 and in Section 6.11 below. Once internalized, if a cleavable linker is used to attach the ALK5 inhibitor to the antibody, for example as described in Section 5.4, the ALK5 inhibitor can be released from the antibody by cleavage in the lysosome or by other cellular mechanism.

The term "antibody fragment" refers to a portion of a full-length antibody, generally the target binding or variable region. Examples of antibody fragments include Fab, Fab', F(ab')2 and Fv fragments. An "Fv" fragment is the minimum antibody fragment which contains a complete target recognition and binding site. This region consists of a dimer of one heavy and one light chain variable domain in a tight, noncovalent association (VH-VL dimer). It is in this configuration that the three CDRs of each variable domain interact to define a target binding site on the surface of the VH-VL dimer. Often, the six CDRs confer target binding specificity to the antibody. However, in some instances even a single variable domain (or half of an Fv comprising only three CDRs specific for a target) can have the ability to recognize and bind target. "Single chain Fv" or "scFv" antibody fragments comprise the VH and VL domains of an antibody in a single polypeptide chain. Generally, the Fv polypeptide further comprises a polypeptide linker between the VH and VL domain that enables the scFv to form the desired structure for target binding. "Single domain antibodies" are composed of a single VH or VL domains which exhibit sufficient affinity to the TNF-α. In a specific embodiment, the single domain antibody is a camelid antibody (see, e.g., Riechmann, 1999, Journal of Immunological Methods 231:25-38).

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

In certain embodiments, the antibodies of the disclosure are monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone and not the method by which it is produced. Monoclonal antibodies useful in connection with the present disclosure can be prepared using a wide variety of techniques known in the art including the use of hybridoma, recombinant, and phage display technologies or a combination thereof. The antibodies of the disclosure include chimeric, primatized, humanized, or human antibodies.

The antibodies of the disclosure can be chimeric antibodies. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397, which are incorporated herein by reference in their entireties.

The antibodies of the disclosure can be humanized. "Humanized" forms of non-human (e.g., murine) antibodies are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; European patent publication no. EP239400; PCT publication WO 91/09967; U.S. Pat. No. 5,225,539; European patent publication no. EP592106; European patent publication no. EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The antibodies of the disclosure can be human antibodies. Completely "human" antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publication nos. WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnology 12:899-903).

The antibodies of the disclosure can be primatized. The term "primatized antibody" refers to an antibody comprising monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

The antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein (see Section 7.6 for a discussion of antibody conjugates), etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

In yet another embodiment of the disclosure, the antibodies or fragments thereof can be antibodies or antibody fragments whose sequence has been modified to alter at least one constant region-mediated biological effector function relative to the corresponding wild type sequence. For example, in some embodiments, an antibody of the disclosure can be modified to reduce at least one constant region-mediated biological effector function relative to an unmodified antibody, e.g., reduced binding to the Fc receptor (FcγR). FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

In other embodiments of the disclosure, an antibody or fragment thereof can be modified to acquire or improve at least one constant region-mediated biological effector function relative to an unmodified antibody, e.g., to enhance FcγR interactions (See, e.g., US 2006/0134709). For example, an antibody of the disclosure can have a constant region that binds FcγRIIA, FcγRIIB and/or FcγRIIIA with greater affinity than the corresponding wild type constant region.

Thus, antibodies of the disclosure can have alterations in biological activity that result in decreased opsonization, phagocytosis, or ADCC. Such alterations are known in the art. For example, modifications in antibodies that reduce ADCC activity are described in U.S. Pat. No. 5,834,597.

In yet another aspect, the antibodies or fragments thereof can be antibodies or antibody fragments that have been modified to increase or reduce their binding affinities to the fetal Fc receptor, FcRn, for example, by mutating the immunoglobulin constant region segment at particular regions involved in FcRn interactions (See, e.g., WO 2005/123780). Such mutations can increase the antibody's binding to FcRn, which protects the antibody from degradation and increases its half-life.

In yet other aspects, an antibody has one or more amino acids inserted into one or more of its hypervariable regions, for example as described in Jung and Pluckthun, 1997, Protein Engineering 10(9):959-966; Yazaki et al., 2004, Protein Eng. Des Sel. 17(5):481-9; and U.S. patent publication no. 2007/0280931.

The targets of the antibodies will depend on the desired therapeutic applications of the ADCs. Typically, the targets are molecules present on the surfaces of cells into which it is desirable to deliver ALK5 inhibitors, such as T cells, and the antibodies preferably internalize upon binding to the target. Internalizing antibodies are described in, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

It is desirable to generate antibodies that bind to T cell surface molecules for applications in which the ADCs are intended to stimulate the immune system by reducing TGF-β activity. Without being bound by theory, it is believed that the delivery of ALK5 inhibitors to T cells can, inter alia, activate $CD4^+$ and/or $CD8^+$ T cell activity and inhibit regulatory T cell activity, both of which contribute to immune tolerance of tumors. Accordingly, the use of antibodies that bind to T cell surface molecules in the ADCs of the disclosure is useful for the treatment of various cancers, for example as described in Section 5.7 below. In various embodiments, the antibody binds to $CD4^+$ T cells, $CD8^+$ T cells, $T_{REG}$ cells, or any combination of the foregoing. In some embodiments, the antibody binds to a pan T cell surface molecule. Examples of T cell surface molecules suitable for targeting include, but are not limited to, CD1, CD2, CD3, CD4, CD5, CD6, CD7, CD8, CD25, CD28, CD70, CD71, CD103, CD184, Tim3, LAG3, CTLA4, and PD1. Examples of antibodies that bind to T cell surface molecules and believed to be internalizing include OKT6 (anti-CD1; ATCC deposit no. CRL8020), OKT11 (anti-CD2; ATCC deposit no. CRL8027); OKT3 (anti-CD3; ATCC deposit no. CRL8001); OKT4 (anti-CD4; ATCC deposit no. CRL8002); OKT8 (anti-CD8; ATCC deposit no. CRL8014); 7D4 (anti-CD25; ATCC deposit no. CRL1698); OKT9 (anti-CD71; ATCC deposit no. CRL8021); CD28.2 (anti-CD28, BD Biosciences Cat. No. 556620); UCHT1 (anti-CD3, BioXCell Cat. No. BE0231); M290 (anti-CD103, BioXCell Cat. No. BE0026); and FR70 (anti-CD70, BioXCell Cat. No. BE0022).

5.3. The ALK5 Inhibitor

The ALK5 inhibitors of the disclosure are preferably small molecules that competitively and reversibly bind to ATP binding site in the cytoplasmic kinase domain of the ALK5 receptor, preventing downstream R-Smad phosphorylation.

The ALK5 inhibitors may but not need be specific or selective for ALK5 vs. other TGF-β family receptors, such as ALK4 and/or ALK7 and/or TGF-β receptor II. In some embodiments, the ALK5 inhibitors have activity towards both ALK5 and TGF-β receptor II. While it is preferable that the ALK5 inhibitor have limited inhibitory activity towards the BMP II receptor, this is not necessary because the ADCs of the disclosure are targeted to T cells, in which BMP II activity is minimal or absent.

The ALK5 inhibitors of the disclosure preferably have an $IC_{50}$ of 100 nM or less, more preferably 50 nM or less, and most preferably 20 nM or less when measured in an in vitro cellular assay using T cells from at least 3 subjects, at least 5 subjects or at least 10 subjects. An exemplary cellular assay set forth in Section 6.6 below. Human instead of mouse cells as well as antibodies recognizing human instead of mouse CD28 and CD3 can be used when the ADC targets a human rather than mouse T cell surface molecule.

Illustrative examples of ALK5 inhibitors suitable for use in the antibody-drug conjugates of the present disclosure include imidazole-benzodioxol compounds, imidazole-quinoxaline compounds, pyrazole-pyrrolo compounds and thiazole type compounds.

In accordance with one aspect of the present disclosure, imidazole-benzodioxol type ALK5 inhibitors have the formula

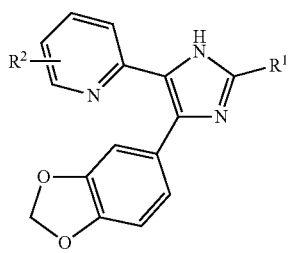

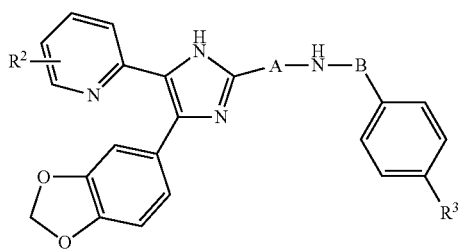

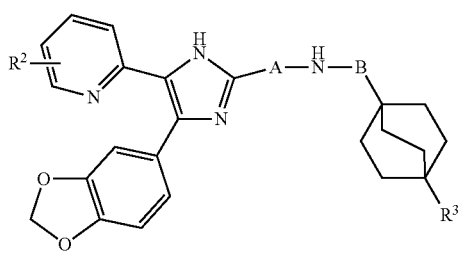

where R¹ is hydrogen or a lower alkyl having from 1 to about 5 carbon atoms, R² is hydrogen or lower alkyl having from 1 to about 5 carbon atoms and R³ is an amide, nitrile, alkynyl having from 1 to about 3 carbon atoms, carboxyl or alkanol group having from 1 to about 5 carbon atoms, A is a direct bond or an alkyl having from 1 to about 5 carbon atoms and B is a direct bond or an alkyl having from 1 to about 5 carbon atoms. In separate preferred embodiments of the present disclosure, R² is hydrogen or methyl, A has 1 carbon atom and B is a direct bond to the benzyl group and R³ is an amide. In a combined preferred embodiment of the present disclosure, R² is hydrogen or methyl, A has 1 carbon atom and B is a direct bond to the benzyl group.

In accordance with another aspect of the present disclosure, imidazole-quinoxaline type ALK5 inhibitors have the formula

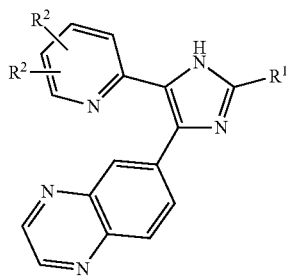

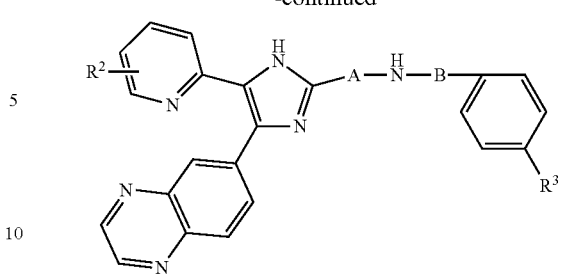

where R¹ is hydrogen or a lower alkyl having from 1 to about 5 carbon atoms, R² is hydrogen, halogen or lower alkyl having from 1 to about 5 carbon atoms and R³ is an amide, nitrile, alkynyl having from 1 to about 3 carbon atoms, carboxyl or alkanol group having from 1 to about 5 carbon atoms, A is a direct bond or an alkyl having from 1 to about 5 carbon atoms and B is a direct bond or an alkyl having from 1 to about 5 carbon atoms. In separate preferred embodiments of the present disclosure, R² is hydrogen or methyl, halogens include fluorine or chlorine, A has 1 carbon atom and B is a direct bond to the benzyl group and R³ is an amide. In a combined preferred embodiment of the present disclosure, R² is hydrogen or methyl, A has 1 carbon atom and B is a direct bond to the benzyl group.

In accordance with another aspect of the present disclosure, pyrazole type ALK5 inhibitors have the formula

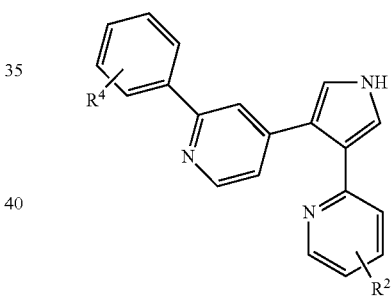

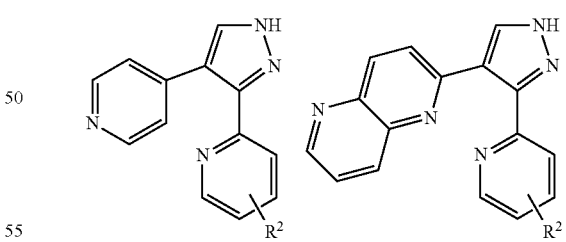

Where R² is hydrogen, halogen or lower alkyl having from 1 to about 5 carbon atoms, R⁴ is hydrogen, halogen, lower alkyl having from 1 to about 5 carbon atoms, alkoxy having from 1 to about 5 carbon atoms, haloalkyl, carboxyl, carboxyalkylester, nitrile, alkylamine or a group having the formula

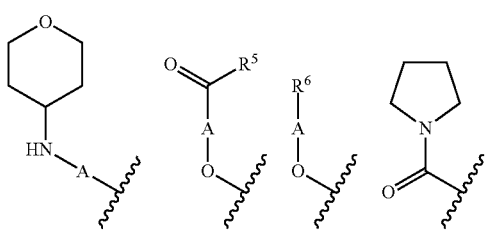
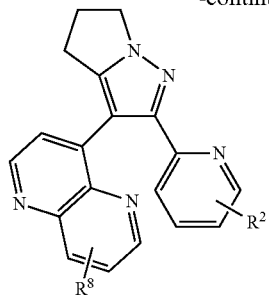

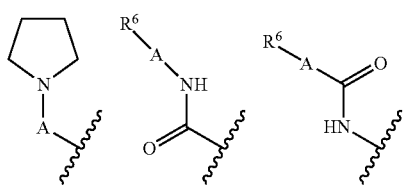

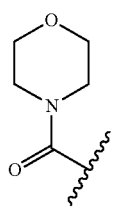

where $R^5$ is lower alkyl having from 1 to about 5 carbon atoms, halogen or morpholino, and $R^6$ is pyrole, cyclohexyl, morpholino, pyrazole, pyran, imidazole, oxane, pyrrolidinyl or alkylamine, and A is a direct bond or an alkyl having from 1 to about 5 carbon atoms.

In accordance with another aspect of the present disclosure, pyrazole-pyrrolo type ALK5 inhibitors have the formula

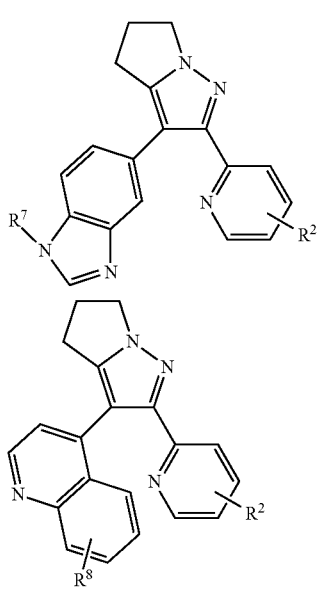

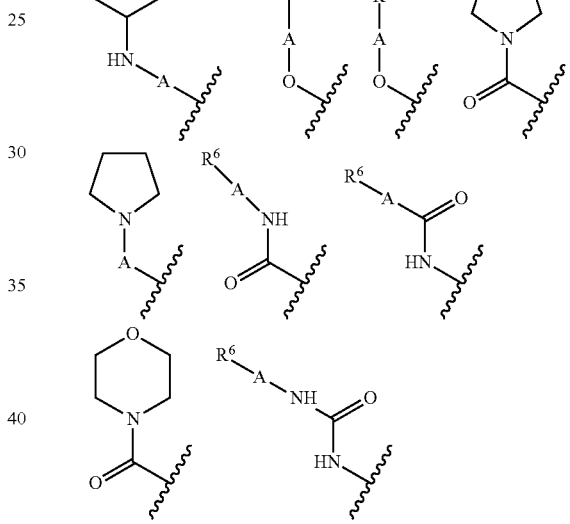

where $R^7$ is hydrogen, halogen, lower alkyl having from 1 to about 5 carbon atoms, alkanol, morpholino or alkylamine, $R^2$ is hydrogen, halogen or lower alkyl having from 1 to about 5 carbon atoms and $R^8$ is hydrogen, hydroxyl, amino, halogen or a group having the formula where $R^5$ is piperazinyl, $R^6$ is morpholino, piperidinyl, piperazinyl, alkoxy, hydroxyl, oxane, halogen, thioalkyl or alkylamine, and A is a lower alkyl having from 1 to about 5 carbon atoms.

In accordance with another aspect of the present disclosure, thiazole type ALK5 inhibitors have the formula

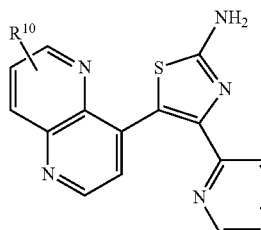

where $R^9$ is hydrogen, halogen or lower alkyl having from 1 to about 5 carbon atoms, and $R^{10}$ is hydrogen or lower alkyl having from 1 to about 5 carbon atoms.

In certain embodiments, the ALK5 inhibitor is selected from any of the compounds designated A to M in Table 1 below:

TABLE 1

| Designation | Structure | Name |
| --- | --- | --- |
| A | 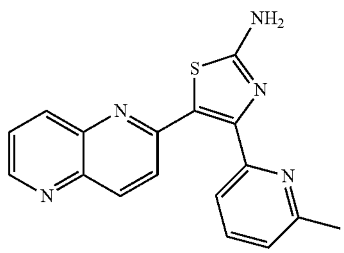 [SMILES: Cc1cccc(-c2nc(N)sc2-c2ccc3ncccc3n2)n1] | 4-(6-methylpyridin-2-yl)-5-(1,5-naphthyridin-2-yl)thiazol-2-amine |
| B | 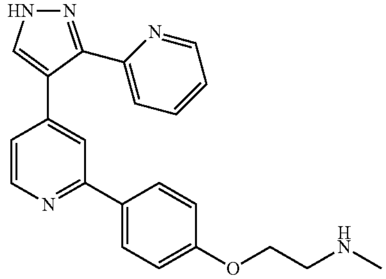 [SMILES: CNCCOc1ccc(-c2cc(-c3c[nH]nc3-c3ccccn3)ccn2)cc1] | N-methyl-2-(4-(4-(3-(pyridin-2-yl)-1H-pyrazol-4-yl)pyridin-2-yl)phenoxy)ethan-1-amine |
| C | 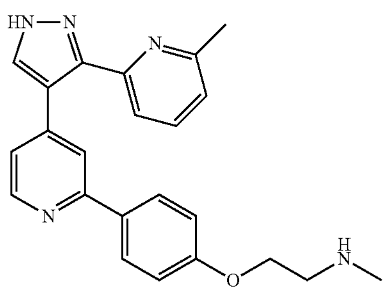 | N-methyl-2-(4-(4-(3-(6-methylpyridin-2-yl)-1H-pyrazol-4-yl)pyridin-2-yl)phenoxy)ethan-1-amine |
| D | 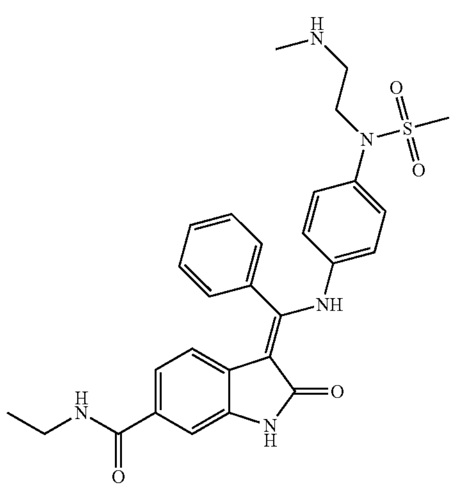 [SMILES: CCNC(=O)c1ccc2c(c1)NC(=O)/C2=C(\Nc1ccc(N(CCNC)S(C)(=O)=O)cc1)c1ccccc1] | (Z)-N-ethyl-3-(((4-(N-(2-(methylamino)ethyl)methylsulfonamido)phenyl)amino)(phenyl)methylene)-2-oxoindoline-6-carboxamide |

TABLE 1-continued

| Designation | Structure | Name |
|---|---|---|
| E | 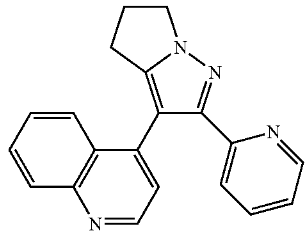 [SMILES: c1ccc(-c2nn3c(c2-c2ccnc4ccccc24)CCC3)nc1] | 4-(2-(pyridin-2-yl)-5,6-dihydro-4H-pyrrolo[1,2-b]pyrazol-3-yl)quinoline |
| F | 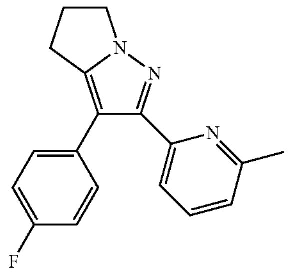 [SMILES: Cc1cccc(-c2nn3c(c2-c2ccc(F)cc2)CCC3)n1] | 3-(4-fluorophenyl)-2-(6-methylpyridin-2-yl)-5,6-dihydro-4H-pyrrolo[1,2-b]pyrazole |
| G | 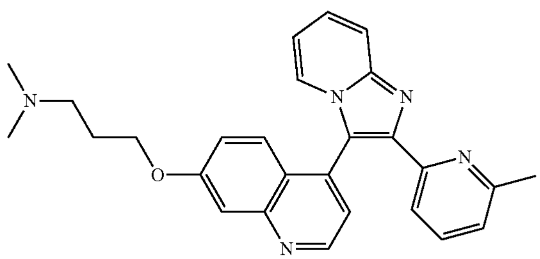 | N,N-dimethyl-3-((4-(2-(6-methylpyridin-2-yl)pyrazolo[1,5-a]pyridin-3-yl)quinolin-7-yl)oxy)propan-1-amine |
| H | 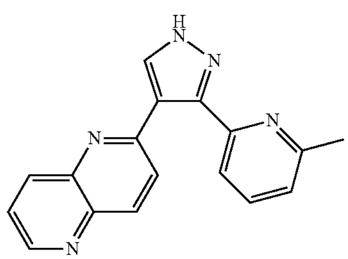 [SMILES: Cc1cccc(-c2n[nH]cc2-c2ccc3ncccc3n2)n1] | 2-(3-(6-methylpyridin-2-yl)-1H-pyrazol-4-yl)-1,5-naphthyridine |
| I | 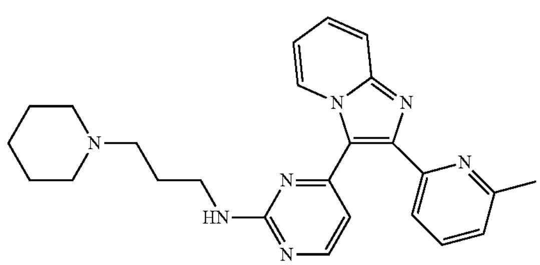 [SMILES: Cc1cccc(-c2nc3ccccn3c2-c2ccnc(NCCCN3CCCCC3)n2)n1] | 4-(2-(6-methylpyridin-2-yl)imidazo[1,2-a]pyridin-3-yl)-N-(3-(piperidin-1-yl)propyl)pyrimidin-2-amine |
| J | 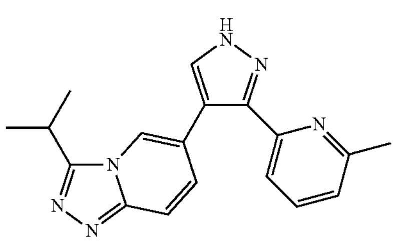 [SMILES: Cc1cccc(-c2n[nH]cc2-c2ccc3nnc(C(C)C)n3c2)n1] | 3-isopropyl-6-(5-(6-methylpyridin-2-yl)-2H-1,2,3-triazol-4-yl)-[1,2,4]triazolo[4,3-a]pyridine |

TABLE 1-continued

| Designation | Structure | Name |
|---|---|---|
| K | 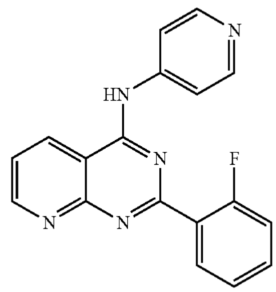 [SMILES: Fc1ccccc1-c1nc(Nc2ccncc2)c2cccnc2n1] | 2-(2-fluorophenyl)-N-(pyridin-4-yl)pyrido[2,3-d]pyrimidin-4-amine |
| L | 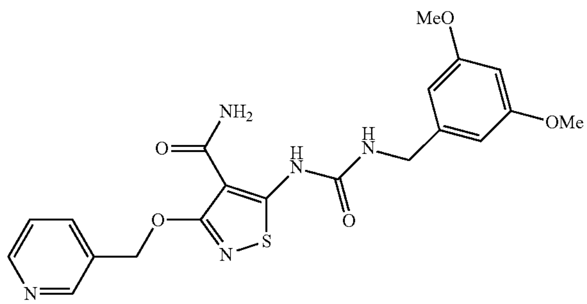 [SMILES: COc1cc(CNC(=O)Nc2snc(OCc3cccnc3)c2C(N)=O)cc(OC)c1] | 5-(3-(2,5-dimethoxybenzyl)ureido)-3-(pyridin-3-ylmethoxy)isothiazole-4-carboxamide |
| M | 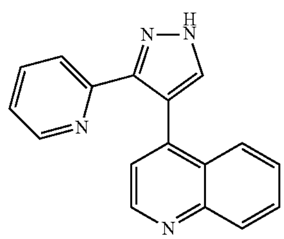 [SMILES: c1ccc(-c2n[nH]cc2-c2ccnc3ccccc23)nc1] | 4-(3-(pyridin-2-yl)-1H-pyrazol-4-yl)quinoline |

In further specific embodiments, the ALK5 inhibitor is selected from any of the compounds designated 1 to 283 in Table 2 below:

TABLE 2

| Designation | Compound Name |
|---|---|
| 1 | 4-(4-(2,3-dihydrobenzo[b][1,4]dioxin-6-yl)-5-(pyridin-2-yl)-1H-imidazol-2-yl)benzamide |
| 2 | 4-((4-(benzo[d][1,3]dioxol-5-yl)-5-(6-methylpyridin-2-yl)-1H-imidazol-2-ylamino) methyl)benzonitrile |
| 3 | 3-((4-(benzo[d][1,3]dioxol-5-yl)-5-(6-methylpyridin-2-yl)-1H-imidazol-2-yl)methylamino) benzonitrile |
| 4 | 3-((4-(benzo[d][1,3]dioxol-5-yl)-5-(6-methylpyridin-2-yl)-1H-imidazol-2-yl)methylamino) benzamide |
| 5 | 4-((4-(benzo[d][1,3]dioxol-5-yl)-5-(6-ethylpyridin-2-yl)-1H-imidazol-2-yl)methylamino) benzamide |
| 6 | 4-(4-(benzo[d][1,3]dioxol-5-yl)-5-(pyridin-2-yl)-1H-imidazol-2-yl)benzamide |
| 7 | 3-((4-(benzo[d][1,3]dioxol-5-yl)-5-(6-methylpyridin-2-yl)-1H-imidazol-2-ylamino)methyl) benzonitrile |
| 8 | 4-(4-(benzo[d][1,3]dioxol-5-yl)-5-(pyridin-2-yl)-1H-imidazol-2-yl)benzamide |
| 9 | 4-((4-(benzo[d][1,3]dioxol-5-yl)-5-(6-methylpyridin-2-yl)-1H-imidazol-2-ylamino)methyl) benzonitrile |
| 10 | 3-((4-(3a,4-dihydrobenzo[d][1,3]dioxol-5-yl)-5-(6-ethylpyridin-2-yl)-1H-imidazol-2-yl) methylamino)benzonitrile |
| 11 | 4-(3a,4-dihydrobenzo[d][1,3]dioxol-5-yl)-N-(4-ethynylbenzyl)-5-(6-methylpyridin-2-yl)-1H-imidazol-2-amine |
| 12 | 4-((4-(3a,4-dihydrobenzo[d][1,3]dioxol-5-yl)-5-(6-methylpyridin-2-yl)-1H-imidazol-2-ylamino) methyl) benzonitrile |
| 13 | 4-((4-(3a,4-dihydrobenzo[d][1,3]dioxol-5-yl)-5-(6-methylpyridin-2-yl)-1H-imidazol-2-yl) methylamino) benzonitrile |
| 14 | 4-((4-(3a,4-dihydrobenzo[d][1,3]dioxol-5-yl)-5-(6-methylpyridin-2-yl)-1H-imidazol-2-yl) methylamino) benzamide |

TABLE 2-continued

| Designation | Compound Name |
|---|---|
| 15 | 4-((4-(3a,4-dihydrobenzo[d][1,3]dioxol-5-yl)-5-(6-ethylpyridin-2-yl)-1H-imidazol-2-yl) methylamino)benzonitrile |
| 16 | 4-(4-(3a,4-dihydrobenzo[d][1,3]dioxol-5-yl)-5-(pyridin-2-yl)-1H-imidazol-2-yl)benzoic acid |
| 17 | 4-(4-(benzo[d][1,3]dioxol-5-yl)-5-(pyridin-2-yl)-1H-imidazol-2-yl)benzamide |
| 18 | 4-(4-(benzo[d][1,3]dioxol-5-yl)-5-(pyridin-2-yl)-1H-imidazol-2-yl)benzoic acid |
| 19 | 4-(4-(benzo[d][1,3]dioxol-5-yl)-5-(pyridin-2-yl)-1H-imidazol-2-yl)benzoic acid |
| 20 | 4-(4-(benzo[d][1,3]dioxol-5-yl)-5-(pyridin-2-yl)-1H-imidazol-2-yl)benzamide |
| 21 | 3-((4-(benzo[d][1,3]dioxol-5-yl)-5-(6-methylpyridin-2-yl)-1H-imidazol-2-ylamino)methyl) benzonitrile |
| 22 | (4-(4-(benzo[d][1,3]dioxol-5-yl)-5-(pyridin-2-yl)-1H-imidazol-2-yl)phenyl) methanol |
| 23 | 4-(4-(benzo[d][1,3]dioxol-5-yl)-5-(pyridin-2-yl)-1H-imidazol-2-yl)benzonitrile |
| 24 | 2-(4-(benzo[d][1,3]dioxol-5-yl)-2-tert-butyl-1H-imidazol-5-yl)-6-methylpyridine |
| 25 | 2-(4-(benzo[d][1,3]dioxol-5-yl)-2-tert-butyl-1H-imidazol-5-yl)-6-methylpyridine |
| 26 | 3-((5-(6-methylpyridin-2-yl)-4-(quinoxalin-6-yl)-1H-imidazol-2-yl)methyl)benzamide |
| 27 | 4-((5-(6-methylpyridin-2-yl)-4-(1,4,4a,8a-tetrahydroquinoxalin-6-yl)-1H-imidazol-2-yl) methylamino)benzamide |
| 28 | 3-((5-(6-methylpyridin-2-yl)-4-(quinoxalin-6-yl)-1H-imidazol-2-yl)methyl)benzamide |
| 29 | 3-((5-(6-methylpyridin-2-yl)-4-(quinoxalin-6-yl)-1 H-imidazol-2-yl)methylamino)benzonitrile |
| 30 | 6-(2-tert-butyl-5-(6-methylpyridin-2-yl)-1 H-imidazol-4-yl)quinoxaline |
| 31 | 4-(5-fluoro-6-methylpyridin-2-yl)-5-(quinoxalin-6-yl)-1H-imidazol-2-amine |
| 32 | 4-((5-(6-ethylpyridin-2-yl)-4-(1,4,4a,8a-tetrahydroquinoxalin-6-yl)-1H-imidazol-2-yl) methylamino)benzonitrile |
| 33 | N-((5-(6-ethylpyridin-2-yl)-4-(1,4,4a,8a-tetrahydroquinoxalin-6-yl)-1H-imidazol-2-yl) methyl)-3-ethynylaniline |
| 34 | 4-((5-(6-ethylpyridin-2-yl)-4-(1,4,4a,8a-tetrahydroquinoxalin-6-yl)-1H-imidazol-2-yl) methylamino)benzamide |
| 35 | 2-(3-(pyridin-2-yl)-1H-pyrazol-4-yl)-1,5-naphthyridine |
| 36 | 3-((5-(6-Methylpyridin-2-yl)-4-(1,5-naphthyridin-2-yl)-1H-pyrazol-1-yl)methyl)benzamide |
| 37 | 2-(3-(6-methylpyridin-2-yl)-1H-pyrazol-4-yl)-1,5-naphthyridine |
| 38 | 3-((3-(6-Methylpyridin-2-yl)-4-(1,5-naphthyridin-2-yl)-1H-pyrazol-1-yl)methyl)benzamide |
| 39 | 2-(3-(6-methylpyridin-2-yl)-1H-pyrazol-4-yl)-1,5-naphthyridine |
| 40 | 2-(3-(pyridin-2-yl)-1H-pyrazol-4-yl)-1,5-naphthyridine |
| 41 | 3-((5-(6-Methylpyridin-2-yl)-4-(1,5-naphthyridin-2-yl)-1H-pyrazol-1-yl)methyl)benzonitrile |
| 42 | 2-(3-(6-methylpyridin-2-yl)-1H-pyrazol-4-yl)-1,5-naphthyridine |
| 43 | 2-(3-(pyridin-2-yl)-1H-pyrazol-4-yl)-1,5-naphthyridine |
| 44 | 3-((3-(6-Methylpyridin-2-yl)-4-(1,5-naphthyridin-2-yl)-1H-pyrazol-1-yl)methyl)benzonitrile |
| 45 | 2-(3-(pyridin-2-yl)-1H-pyrazol-4-yl)-1,5-naphthyridine |
| 46 | dimethyl-{2-[(4-{4-[3-(pyridin-2-yl)-1H-pyrazol-4-yl]-2-pyridinyl}phenyl)oxy]ethyl}amine |
| 47 | 2-(4-chlorophenyl)-4-(3-(pyridin-2-yl)-1H-pyrazol-4-yl)pyridine |
| 48 | [(4-{4-[3-(pyridin-2-yl)-1H-pyrazol-4-yl]-pyridin-2-yl}phenyl)-methyl]tetrahydro-2H-pyran-4-ylamine |
| 49 | 2-{4-[(2-chloroethyl)oxy]phenyl}-4[3-(pyridin-2-yl)-1H-pyrazol-4-yl]pyridine |
| 50 | N-(2-methoxyethyl)-4-(4-(3-(pyridin-2-yl)-1H-pyrazol-4-yl)pyridin-2-yl)benzamide |
| 51 | 2[4-methylphenyl]-4-(3-pyridin-2-yl)-1H-pyrazol-4-yl pyridine |
| 52 | 4-(3-(pyridin-2-yl)-1H-pyrazol-4-yl)-2-(3-(trifluoromethyl)phenyl)pyridine |
| 53 | N-(2-methoxyethyl)-4-(4-(3-(pyridin-2-yl)-1H-pyrazol-4-yl)pyridin-2-yl)benzamide |
| 54 | 2-(4-chlorophenyl)-4-(3-(pyridin-2-yl)-1H-pyrazol-4-yl)pyridine |
| 55 | 2[2-(trifluoromethyl)phenyl]-4-(3-pyridin-2-yl-1H-pyrazol-4-yl)pyridine |
| 56 | 2-(2-fluorophenyl)-4-(3-(pyridin-2-yl)-1H-pyrazol-4-yl)pyridine |
| 57 | 2-(4-(2-(1H-imidazol-1-yl)ethoxy)phenyl)-4-(3-(pyridin-2-yl)-1H-pyrazol-4-yl)pyridine |
| 58 | 2[4-isopropylphenyl]-4-[3-(pyridin-2-yl)-1H-pyrazol-4-yl]pyridine |
| 59 | N-(4-(4-(3-(pyridin-2-yl)-1H-pyrazol-4-yl)pyridin-2-yl)phenyl)tetrahydro-2H-pyran-4-carboxam ide |
| 60 | 2-phenyl-4-(3-(pyridin-2-yl)-1H-pyrazol-4-yl)pyridine |
| 61 | 2-(4-(2-cyclohexylethoxy)phenyl)-4-(3-(pyridin-2-yl)-1H-pyrazol-4-yl)pyridine |
| 62 | 2-pyrrolidin-1-yl-N-{4-[4-(3-pyridin-2-yl-1H-pyrazol-4-yl)-pyridin-2-yl[phenyl}acetamide |
| 63 | 4-[3-(pyridin-2-yl)-1H-pyrazol-4-yl]-2-[4-(1-pyrrolidinylmethyl)phenyl]pyridine |
| 64 | 2-(3-methoxyphenyl)-4-(3-(pyridin-2-yl)-1H-pyrazol-4-yl)pyridine |

TABLE 2-continued

| Designation | Compound Name |
|---|---|
| 65 | 4-(4-(3-(pyridin-2-yl)-1H-pyrazol-4-yl)pyridin-2-yl)benzonitrile |
| 66 | 4-(3-(pyridin-2-yl)-1H-pyrazol-4-yl)-2-(4-(trifluoromethyl)phenyl)pyridine |
| 67 | 2-(2-fluorophenyl)-4-(3-(pyridin-2-yl)-1H-pyrazol-4-yl)pyridine |
| 68 | N-methyl-4-(4-(3-(pyridin-2-yl)-1H-pyrazol-4-yl)pyridin-2-yl)-N-(tetrahydro-2H-pyran-4-yl) benzamide |
| 69 | 2-(4-fluorophenyl)-4-(3-(pyridin-2-yl)-1H-pyrazol-4-yl)pyridine |
| 70 | 4-(3-(pyridin-2-yl)-1H-pyrazol-4-yl)-2-(3-(trifluoromethyl)phenyl)pyridine |
| 71 | 2-(3-methoxyphenyl)-4-(3-(pyridin-2-yl)-1H-pyrazol-4-yl)pyridine |
| 72 | N-methyl-4-(4-(3-(pyridin-2-yl)-1H-pyrazol-4-yl)pyridin-2-yl)-N-(tetrahydro-2H-pyran-4-yl) benzamide |
| 73 | 2[3-methylphenyl]-4-(3-pyridin-2-yl-1H-pyrazol-4-yl)pyridine |
| 74 | 4-{2-[(4-{4-[3-(pyridin-2-yl)-1H-pyrazol-4-yl]-pyridin-2-yl}-phenyl)oxy]ethyl}morpholine |
| 75 | 2-(2-methylphenyl)-4-[3-(pyridin-2-yl)-1H-pyrazol-4-yl]pyridine |
| 76 | 4-(3-(pyridin-2-yl)-1H-pyrazol-4-yl)-2-(4-(trifluoromethyl)phenyl)pyridine |
| 77 | 4-(4-(3-(pyridin-2-yl)-1H-pyrazol-4-yl)pyridin-2-yl)benzonitrile |
| 78 | 1-(4-(4-(3-(pyridin-2-yl)-1H-pyrazol-4-yl)pyridin-2-yl)phenoxy)propan-2-one |
| 79 | 4-(4-(4-(3-(pyridin-2-yl)-1H-pyrazol-4-yl)pyridin-2-yl)benzyl)morpholine |
| 80 | 4-(4-(3-(pyridin-2-yl)-1H-pyrazol-4-yl)pyridin-2-yl)-N-(tetrahydro-2H-pyran-4-yl) benzamide |
| 81 | N-(4-(4-(3-(pyridin-2-yl)-1H-pyrazol-4-yl)pyridin-2-yl)benzyl)tetrahydro-2H-pyran-3-amine |
| 82 | 1-(4-(4-(3-(pyridin-2-yl)-1H-pyrazol-4-yl)pyridin-2-yl)phenoxy)propan-2-one |
| 83 | 4-(3-(pyridin-2-yl)-1H-pyrazol-4-yl)-2-(4-(2-(pyrrolidin-1-yl)ethoxy)phenyl)pyridine |
| 84 | 4-(3-(pyridin-2-yl)-1H-pyrazol-4-yl)-2-(4-(2-(pyrrolidin-1-yl)ethoxy)phenyl)pyridine |
| 85 | 4-(4-(3-(pyridin-2-yl)-1H-pyrazol-4-yl)pyridin-2-yl)benzyl)morpholine |
| 86 | 4-(4-(3-pyridin-2-yl-1H-pyrazol-4-yl)pyridin-2-yl]benzoic acid methyl ester 4-(4-(3-(pyridin-2-yl)-1H-pyrazol-4-yl)pyridin-2-yl)benzoic acid |
| 87 | N-(4-(4-(3-(pyridin-2-yl)-1H-pyrazol-4-yl)pyridin-2-yl)phenyl)-2-(pyrrolidin-1-yl)acetamide |
| 88 | N,N-dimethyl-3-(3-(4-(3-(pyridin-2-yl)-1H-pyrazol-4-yl)pyridin-2-yl)phenyl)propan-1-amine |
| 89 | 2[4-methoxyphenyl]-4-(3-pyridin-2-yl-1H-pyrazol-4-yl)pyridine |
| 90 | 4-(3-(pyridin-2-yl)-1H-pyrazol-4-yl)quinoline |
| 91 | 4-(1-benzyl-3-(pyridin-2-yl)-1H-pyrazol-4-yl)quinoline |
| 92 | 3-((5-(6-Methylpyridin-2-yl)-4-(quinolin-6-yl)-1H-pyrazol-1-yl)methyl)benzamide |
| 93 | 4-(3-(pyridin-2-yl)-1H-pyrazol-4-yl)quinoline |
| 94 | 3-((4-(6-Methylpyridin-2-yl)-3-(quinolin-6-yl)-1H-pyrazol-1-yl)methyl)benzamide |
| 95 | 3-((5-(6-Methylpyridin-2-yl)-4-(quinolin-6-yl)-1H-pyrazol-1-yl)methyl)benzonitrile |
| 96 | 4-(3-(pyridin-2-yl)-1H-pyrazol-4-yl)quinoline |
| 97 | 3-((3-(6-Methylpyridin-2-yl)-4-(quinolin-6-yl)-1H-pyrazol-1-yl)methyl)benzamide |
| 98 | 4-(3-(5-fluoropyridin-2-yl)-1H-pyrazol-4-yl)quinoline |
| 99 | 4-(5-cyclopropyl-3-(pyridin-2-yl)-1H-pyrazol-4-yl)quinoline |
| 100 | 4-(4-(pyridin-2-yl)-1H-pyrazol-3-yl)quinoline |
| 101 | 4-(3-(5-fluoropyridin-2-yl)-1H-pyrazol-4-yl)quinoline |
| 102 | 4-(1-benzyl-3-(pyridin-2-yl)-1H-pyrazol-4-yl)quinoline |
| 103 | 4-(3-(5-fluoropyridin-2-yl)-1H-pyrazol-4-yl)quinoline |
| 104 | 4-(3-(pyridin-2-yl)-1H-pyrazol-4-yl)quinoline |
| 105 | 4-[3-(6-Bromo-pyridin-2-yl)-1H-pyrazol-4-yl]-quinoline |
| 106 | 4-(3-(5-chloropyridin-2-yl)-1H-pyrazol-4-yl)quinoline |
| 107 | 4-(1-benzyl-3-(pyridin-2-yl)-1H-pyrazol-4-yl)quinoline |
| 108 | 4-(3-(5-fluoropyridin-2-yl)-1H-pyrazol-4-yl)quinoline |
| 109 | 4-(3-(3-(trifluoromethyl)phenyl)-1H-pyrazol-4-yl)quinoline |
| 110 | 3-((4-(6-Methylpyridin-2-yl)-3-(quinolin-6-yl)-1H-pyrazol-1-yl)methyl)benzonitrile |
| 111 | 4-[3-(6-Methyl-pyridin-2-yl)-1H-pyrazol-4-yl]-quinoline |
| 112 | 4-(3-(pyridin-2-yl)-1H-pyrazol-4-yl)quinoline |
| 113 | 4-(1-benzyl-3-(pyridin-2-yl)-1H-pyrazol-4-yl)quinoline |
| 114 | 4-(3-(3-(trifluoromethyl)phenyl)-1H-pyrazol-4-yl)quinoline |
| 115 | 3-((3-(6-Methylpyridin-2-yl)-4-(quinolin-6-yl)-1H-pyrazol-1-yl)methyl)benzonitrile |
| 116 | 4-(3-(thiophen-2-yl)-1H-pyrazol-4-yl)quinoline |
| 117 | 4[5-Methyl-3-(6-methyl-pyridin-2-yl)-1H-pyrazol-4-yl]-quinoline |
| 118 | 4-[5-Methyl-3-(6-methyl-pyridin-2-yl)-1H-pyrazol-4-yl]-quinoline |
| 119 | 4-(3-(thiophen-2-yl)-1H-pyrazol-4-yl)quinoline |
| 120 | 4-[5-Methyl-3-(6-methyl-pyridin-2-yl)-1H-pyrazol-4-yl]-quinoline |
| 121 | 1,2-dimethyl-4-phenyl-5-(quinoxalin-6-yl)-1H-pyrazol-3(2H)-one |
| 122 | 4-(3-chlorophenyl)-1,2-dimethyl-5-(quinoxalin-6-yl)-1H-pyrazol-3(2H)-one |
| 123 | 4-(3-fluorophenyl)-1,2-dimethyl-5-(quinoxalin-6-yl)-1H-pyrazol-3(2H)-one |
| 124 | methyl 3-(1,2-dimethyl-3-oxo-5-(quinoxalin-6-yl)-2,3-dihydro-1H-pyrazol-4-yl)benzoate |

TABLE 2-continued

| Designation | Compound Name |
|---|---|
| 125 | 1,2-dimethyl-4-(2-methylpyridin-4-yl)-5-(quinoxalin-6-yl)-1H-pyrazol-3(2H)-one |
| 126 | 1,2-dimethyl-5-(quinoxalin-6-yl)-4-m-tolyl-1H-pyrazol-3(2H)-one |
| 127 | 4-(2-hydroxyphenyl)-1,2-dimethyl-5-(quinoxalin-6-yl)-1H-pyrazol-3(2H)-one |
| 128 | 4-(1H-indol-5-yl)-1,2-dimethyl-5-(quinoxalin-6-yl)-1H-pyrazol-3(2H)-one |
| 129 | 1-(3-(1,2-dimethyl-3-oxo-5-(quinoxalin-6-yl)-2,3-dihydro-1H-pyrazol-4-yl)phenyl)-3-methylurea |
| 130 | 4-(3-acetylphenyl)-1,2-dimethyl-5-(quinoxalin-6-yl)-1H-pyrazol-3(2H)-one |
| 131 | 4-(3-(methoxymethyl)phenyl)-1,2-dimethyl-5-(quinoxalin-6-yl)-1H-pyrazol-3(2H)-one |
| 132 | 4-(2-aminophenyl)-1,2-dimethyl-5-(quinoxalin-6-yl)-1H-pyrazol-3(2H)-one |
| 133 | 3-(1,2-dimethyl-3-oxo-5-(quinoxalin-6-yl)-2,3-dihydro-1H-pyrazol-4-yl)benzonitrile |
| 134 | 4-(3-methoxyphenyl)-1,2-dimethyl-5-(quinoxalin-6-yl)-1H-pyrazol-3(2H)-one |
| 135 | 1,2-dimethyl-4-(pyridin-3-yl)-5-(quinoxalin-6-yl)-1H-pyrazol-3(2H)-one |
| 136 | 1,2-dimethyl-5-(quinoxalin-6-yl)-4-(thiophen-2-yl)-1H-pyrazol-3(2H)-one |
| 137 | 1,2-dimethyl-5-(quinoxalin-6-yl)-4-(3-vinylphenyl)-1H-pyrazol-3(2H)-one |
| 138 | 2-(3-(1,2-dimethyl-3-oxo-5-(quinoxalin-6-yl)-2,3-dihydro-1H-pyrazol-4-yl)phenyl)acetonitrile |
| 139 | N-(3-(1,2-dimethyl-3-oxo-5-(quinoxalin-6-yl)-2,3-dihydro-1H-pyrazol-4-yl)phenyl)acetamide 3-(1,2-dimethyl-3-oxo-5-(quinoxalin-6-yl)-2,3-dihydro-1H-pyrazol-4-yl)benzamide |
| 140 | 1,2-dimethyl-5-(quinoxalin-6-yl)-4-(thiophen-3-yl)-1H-pyrazol-3(2H)-one |
| 141 | 4-(furan-2-yl)-1,2-dimethyl-5-(quinoxalin-6-yl)-1H-pyrazol-3(2H)-one |
| 142 | 4-(furan-3-yl)-1,2-dimethyl-5-(quinoxalin-6-yl)-1H-pyrazol-3(2H)-one |
| 143 | 4-(benzo[c][1,2,5]oxadiazol-5-yl)-1,2-dimethyl-5-(quinoxalin-6-yl)-1H-pyrazol-3(2H)-one |
| 144 | N-(3-(1,2-dimethyl-3-oxo-5-(quinoxalin-6-yl)-2,3-dihydro-1H-pyrazol-4-yl)phenyl)ethanesulfonamide |
| 145 | 1,2-dimethyl-5-(quinoxalin-6-yl)-4-(3-(trifluoromethyl)phenyl)-1H-pyrazol-3(2H)-one |
| 146 | 4-(4-aminophenyl)-1,2-dimethyl-5-(quinoxalin-6-yl)-1H-pyrazol-3(2H)-one |
| 147 | 4-(3-ethylphenyl)-1,2-dimethyl-5-(quinoxalin-6-yl)-1H-pyrazol-3(2H)-one |
| 148 | 4-(3-hydroxyphenyl)-1,2-dimethyl-5-(quinoxalin-6-yl)-1H-pyrazol-3(2H)-one |
| 149 | 4-(3-aminophenyl)-1,2-dimethyl-5-(quinoxalin-6-yl)-1H-pyrazol-3(2H)-one |
| 150 | 4-(3-isopropylphenyl)-1,2-dimethyl-5-(quinoxalin-6-yl)-1H-pyrazol-3(2H)-one |
| 151 | 2-(1,2-dimethyl-3-oxo-5-(quinoxalin-6-yl)-2,3-dihydro-1H-pyrazol-4-yl)benzonitrile |
| 152 | 1,2-dimethyl-4-(6-methylpyridin-2-yl)-5-(quinoxalin-6-yl)-1H-pyrazol-3(2H)-one |
| 153 | N-(3-(1,2-dimethyl-3-oxo-5-(quinoxalin-6-yl)-2,3-dihydro-1H-pyrazol-4-yl)phenyl)methanesulfonamide |
| 154 | 1,2-dimethyl-4-(pyridin-2-yl)-5-(quinoxalin-6-yl)-1-pyrazol-3(2H)-one |
| 155 | 1,2-dimethyl-4-(3-(methylthio)phenyl)-5-(quinoxalin-6-yl)-1H-pyrazol-3(2H)-one |
| 156 | 4-(3-(aminomethyl)phenyl)-1,2-dimethyl-5-(quinoxalin-6-yl)-1H-pyrazol-3(2H)-one |
| 157 | 4-(4-hydroxyphenyl)-1,2-dimethyl-5-(quinoxalin-6-yl)-1H-pyrazol-3(2H)-one |
| 158 | 4-(benzo[b]thiophen-3-yl)-1,2-dimethyl-5-(quinoxalin-6-yl)-1H-pyrazol-3(2H)-one |
| 159 | 4-(3-bromophenyl)-1,2-dimethyl-5-(quinoxalin-6-yl)-1H-pyrazol-3(2H)-one |
| 160 | 4-(3-(hydroxymethyl)phenyl)-1,2-dimethyl-5-(quinoxalin-6-yl)-1H-pyrazol-3(2H)-one |
| 161 | 1-methyl-5-(2-pyridin-2-yl-5,6-dihydro-4H-pyrrolo[1,2-b]pyrazol-3-yl)-1H-benzoimidazole |
| 162 | 1-methyl-6-[2-(6-methylpyridin-2-yl)-5,6-dihydro-4H-pyrrolo-[1,2-b]pyrazol-3-yl]-1H-benzoimidazole |
| 163 | N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine |
| 164 | N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine |
| 165 | N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine |
| 166 | 3-[6-(2-pyridin-2-yl-5,6-dihydro-4H-pyrrolo[1,2-b]pyrazol-3-yl)-benzoimidazol-1-yl]-propan-1-ol |
| 167 | 3-[6-(2-pyridin-2-yl-5,6-dihydro-4H-pyrrolo[1,2-b]pyrazol-3-yl)-benzoimidazol-1-yl]-propan-1-ol |
| 168 | 3-(6-(2-(6-methylpyridin-2-yl)-5,6-dihydro-4H-pyrrolo[1,2-b]pyrazol-3-yl)-1H-benzo[d]imidazol-1-yl)propan-1-ol |
| 169 | 1-methyl-5-(2-pyridin-2-yl-5,6-dihydro-4H-pyrrolo[1,2-b]pyrazol-3-yl)-1H-benzoimidazole |
| 170 | 3-(6-(2-(6-methylpyridin-2-yl)-5,6-dihydro-4H-pyrrolo[1,2-b]pyrazol-3-yl)-1H-benzo[d]imidazol-1-yl)propan-1-ol |
| 171 | 1-methyl-5-(2-pyridin-2-yl-5,6-dihydro-4H-pyrrolo[1,2-b]pyrazol-3-yl)-1H-benzoimidazole |

TABLE 2-continued

| Designation | Compound Name |
|---|---|
| 172 | dimethyl-{3-[6-(2-pyridin-2-yl-5,6-dihydro-4H-pyrrolo[1,2-b]pyrazol-3-yl)-benzoimidazol-1-yl]-propyl}-amine |
| 173 | 5-[2-(6-methylpyridin-2-yl)-5,6-dihydro-4H-pyrrolo[1,2-b]pyrazol-3-yl]-1-[3-(tetrahydropyran-2-yloxy)-propyl]-1H-benzoimidazole |
| 174 | 3-[6-(2-pyridin-2-yl-5,6-dihydro-4H-pyrrolo[1,2-b]pyrazol-3-yl)-benzoimidazol-1-yl]-propan-1-ol |
| 175 | 5-(2-pyridin-2-yl-5,6-dihydro-4H-pyrrolo[1,2-b]pyrazol-3-yl)-1-[3-(tetrahydro-pyran-2-yloxy)-propyl]-1H-benzoimidazole |
| 176 | 6-[2-(6-methyl-pyridin-2-yl)-5,6-dihydro-4H-pyrrolo[1,2-b]pyrazol-3-yl]-1-(3-pyrrolidin-1-yl-propyl)-1 H-benzoimidazole |
| 177 | 1-methyl-6-[2-(6-methylpyridin-2-yl)-5,6-dihydro-4H-pyrrolo-[1,2-b]pyrazol-3-yl]-1H-benzoimidazole |
| 178 | 1-methyl-6-(2-pyridin-2-yl-5,6-dihydro-4H-pyrrolo[1,2-b]pyrazol-3-yl)-Benzoimidazole |
| 179 | N,N-diethyl-3-(6-(2-(6-methylpyridin-2-yl)-5,6-dihydro-4H-pyrrolo[1,2-b]pyrazol-3-yl)-1H-benzo[d]imidazol-1-yl)propan-1-amine |
| 180 | 5-(2-pyridin-2-yl-5,6-dihydro-4H-pyrrolo[1,2-b]pyrazol-3-yl)-1-[3-(tetrahydro-pyran-2-yloxy)-propyl]-1H-benzoimidazole |
| 181 | 6-[2-(6-methyl-pyridin-2-yl)-5,6-dihydro-4H-pyrrolo[1,2-b]pyrazol-3-yl]-1-(3-pyrrolidin-1-yl-propyl)-1 H-benzoimidazole |
| 182 | 5-(2-pyridin-2-yl-5,6-dihydro-4H-pyrrolo[1,2-b]pyrazol-3-yl)-1-[3-(tetrahydro-pyran-2-yloxy)-propyl]-1 H-benzoimidazole |
| 183 | 6-(2-(pyridin-2-yl)-5,6-dihydro-4H-pyrrolo[1,2-b]pyrazol-3-yl)-1-(3-(pyrrolidin-1-yl)propyl)-1 H-benzo[d]imidazole |
| 184 | 5-(2-(pyridin-2-yl)-5,6-dihydro-4H-pyrrolo[1,2-b]pyrazol-3-yl)-1H-benzo[d]imidazole |
| 185 | 3-(6-(2-(6-methylpyridin-2-yl)-5,6-dihydro-4H-pyrrolo[1,2-b]pyrazol-3-yl)-1H-benzo[d]imidazol-1-yl)propan-1-ol |
| 186 | 1-methyl-6-(2-pyridin-2-yl-5,6-dihydro-4H-pyrrolo[1,2-b]pyrazol-3-yl)-1 Benzoimidazole |
| 187 | 6-[2-(6-methyl-pyridin-2-yl)-5,6-dihydro-4H-pyrrolo[1,2-b]pyrazol-3-yl]-1Hbenzoimidazole |
| 188 | 6-[2-(6-methyl-pyridin-2-yl)-5,6-dihydro-4H-pyrrolo[1,2-b]pyrazol-3-yl]-1-(3-piperidin-1-yl-propyl)-1H-benzoimidazole |
| 189 | 6-(2-(pyridin-2-yl)-5,6-dihydro-4H-pyrrolo[1,2-b]pyrazol-3-yl)-1-(3-(pyrrolidin-1-yl)propyl)-1H-benzo[d]imidazole |
| 190 | 4-(3-(6-(2-(6-methylpyridin-2-yl)-5,6-dihydro-4H-pyrrolo[1,2-b]pyrazol-3-yl)-1H-benzo[d]imidazol-1-yl)propyl)morpholine |
| 191 | 6-[2-(6-methyl-pyridin-2-yl)-5,6-dihydro-4H-pyrrolo[1,2-b]pyrazol-3-yl]-1-(3-piperidin-1-yl-propyl)-1H-benzoimidazole |
| 192 | 4-(3-(6-(2-(6-methylpyridin-2-yl)-5,6-dihydro-4H-pyrrolo[1,2-b]pyrazol-3-yl)-1H-benzo[d]imidazol-1-yl)propyl)morpholine |
| 193 | 6-[2-(6-methyl-pyridin-2-yl)-5,6-dihydro-4H-pyrrolo[1,2-b]pyrazol-3-yl]-1Hbenzoimidazole |
| 194 | 1-methyl-5-(2-(6-methylpyridin-2-yl)-5,6-dihydro-4H-pyrrolo[1,2-b]pyrazol-3-yl)-H-benzo[d]imidazole |
| 195 | N,N-dimethyl-3-(5-(2-(pyridin-2-yl)-5,6-dihydro-4H-pyrrolo[1,2-b]pyrazol-3-yl)-1H-benzo[d]imidazol-1-yl)propan-1-amine |
| 196 | 6-(2-(pyridin-2-yl)-5,6-dihydro-4H-pyrrolo[1,2-b]pyrazol-3-yl)-1-(3-(pyrrolidin-1-yl)propyl)-1H-benzo[d]imidazole |
| 197 | dimethyl-(3-{6-[2-(6-methyl-pyridin-2-yl)-5,6-dihydro-4H-pyrrolo[1,2-b]pyrazol-3-yl]-benzoimidazol-1-yl}-propyl)-amine |
| 198 | 4-(3-(6-(2-(6-methylpyridin-2-yl)-5,6-dihydro-4H-pyrrolo[1,2-b]pyrazol-3-yl)-1H-benzo[d]imidazol-1-yl)propyl)morpholine |
| 199 | 3-(benzo[d][1,3]dioxol-5-yl)-2-(pyridin-2-yl)-6,7-dihydro-5H-pyrrolo[1,2-a]imidazole |
| 200 | 3-hydroxy-N-(4-(2-(pyridin-2-yl)-5,6-dihydro-4H-pyrrolo[1,2-b]pyrazol-3-yl)quinolin-7-yl)propanamide |
| 201 | 4-(2-(pyridin-2-yl)-5,6-dihydro-4H-pyrrolo[1,2-b]pyrazol-3-yl)-2-(pyrrolidin-1-yl)quinolone |
| 202 | 4-[4-(2-pyridin-2-yl-5,6-dihydro-4H-pyrrolo[1,2-b]pyrazol-3-yl)-quinolin-7-yloxy]-benzonitrile |
| 203 | 1-(3-(dimethylamino)propyl)-3-(4-(2-(pyridin-2-yl)-5,6-dihydro-4H-pyrrolo[1,2-b]pyrazol-3-yl)quinolin-7-yl)urea |
| 204 | 4-[4-(2-pyridin-2-yl-5,6-dihydro-4H-pyrrolo[1,2-b]pyrazol-3-yl)-quinolin-7-yloxy]-benzamide |
| 205 | methyl 4-(2-(pyridin-2-yl)-5,6-dihydro-4H-pyrrolo[1,2-b]pyrazol-3-yl)quinolin-7-ylcarbamate |
| 206 | dimethyl-{5-[4-(2-pyridin-2-yl-5,6-dihydro-4H-pyrrolo[1,2-b]pyrazol-3-yl)-quinolin-7-yloxy]-pentyl}-amine |
| 207 | dimethyl-{4-[4-(2-pyridin-2-yl-5,6-dihydro-4H-pyrrolo[1,2-b]pyrazol-3-yl)-quinolin-7-yloxy]-benzyl}-amine |
| 208 | 2-hydroxyethyl 4-(2-(pyridin-2-yl)-5,6-dihydro-4H-pyrrolo[1,2-b]pyrazol-3-yl)quinolin-7-ylcarbamate |
| 209 | ethyl-methyl-{2-[4-(2-pyridin-2-yl-5,6-dihydro-4H-pyrrolo[1,2-b]pyrazol-3-yl)-quinolin-7-yloxy]-ethyl}-amine |
| 210 | 4-(2-(6-ethylpyridin-2-yl)-5,6-dihydro-4H-pyrrolo[1,2-b]pyrazol-3-yl)quinoline |

TABLE 2-continued

| Designation | Compound Name |
|---|---|
| 211 | 2-(dimethylamino)-N-(4-(2-(pyridin-2-yl)-5,6-dihydro-4H-pyrrolo[1,2-b]pyrazol-3-yl)quinolin-7-yl)acetamide |
| 212 | 2-(4-(2-(pyridin-2-yl)-5,6-dihydro-4H-pyrrolo[1,2-b]pyrazol-3-yl)quinolin-7-yloxy)ethanol |
| 213 | 3-methoxy-N-(4-(2-(pyridin-2-yl)-5,6-dihydro-4H-pyrrolo[1,2-b]pyrazol-3-yl)quinolin-7-yl)propanamide |
| 214 | 1-(2-(dimethylamino)ethyl)-3-(4-(2-(pyridin-2-yl)-5,6-dihydro-4H-pyrrolo[1,2-b]pyrazol-3-yl)quinolin-7-yl)urea |
| 215 | N-(4-(2-(pyridin-2-yl)-5,6-dihydro-4H-pyrrolo[1,2-b]pyrazol-3-yl)quinolin-7-yl)acetamide |
| 216 | 2-(ethylthio)-4-(2-(pyridin-2-yl)-5,6-dihydro-4H-pyrrolo[,2-b]pyrazol-3-yl)quinolone |
| 217 | 7-[3-(4-methyl-piperazin-1-yl)-propoxy]-4-(2-pyridin-2-yl-5,6-dihydro-4H-pyrrolo[1,2-b]pyrazol-3-yl)-quinoline |
| 218 | 4-(2-(pyridin-2-yl)-5,6-dihydro-4H-pyrrolo[1,2-b]pyrazol-3-yl)quinolin-7-amine |
| 219 | N-(2-(dimethylamino)ethyl)-4-(2-(6-methylpyridin-2-yl)-5,6-dihydro-4H-pyrrolo[1,2-b]pyrazol-3-yl)quinoline-6-carboxamide |
| 220 | 4-(2-(5-fluoropyridin-2-yl)-5,6-dihydro-4H-pyrrolo[1,2-b]pyrazol-3-yl)quinoline |
| 221 | 7-(2-chloro-ethoxy)-4-(2-pyridin-2-yl-5,6-dihydro-4H-pyrrolo[1,2-b]pyrazol-3-yl)-quinoline |
| 222 | N,N-dimethyl-4-[4-(2-pyridin-2-yl-5,6-dihydro-4H-pyrrolo[1,2-b]pyrazol-3-yl)-quinolin-7-yloxy]-benzamide |
| 223 | 4-(2-(6-methylpyridin-2-yl)-5,6-dihydro-4H-pyrrolo[1,2-b]pyrazol-3-yl)quinoline |
| 224 | 4-(2-(pyridin-2-yl)-5,6-dihydro-4H-pyrrolo[1,2-b]pyrazol-3-yl)quinoline |
| 225 | 4-[4-(2-pyridin-2-yl-5,6-dihydro-4H-pyrrolo[1,2-b]pyrazol-3-yl)-quinolin-7-yloxy]-benzoic acid |
| 226 | 4-(2-pyridin-2-yl-5,6-dihydro-4H-pyrrolo[1,2-b]pyrazol-3-yl)-quinolin-7-ol |
| 227 | 2-chloro-4-(2-(pyridin-2-yl)-5,6-dihydro-4H-pyrrolo[1,2-b]pyrazol-3-yl)quinolone |
| 228 | 7-[3-(1-methyl-pyrrolidin-2-yl)-propoxy]-4-(2-pyridin-2-yl-5,6-dihydro-4H-pyrrolo[1,2-b]pyrazol-3-yl)-quinoline |
| 229 | methyl 4-(2-(6-methylpyridin-2-yl)-5,6-dihydro-4H-pyrrolo[1,2-b]pyrazol-3-yl)quinoline-6-carboxylate |
| 230 | 4-(2-pyridin-2-yl-5,6-dihydro-4H-pyrrolo[1,2-b]pyrazol-3-yl)-7-(tetrahydro-furan-2-ylmethoxy)-quinoline |
| 231 | 7-[2-(4-methyl-piperazin-1-yl)-ethoxy]-4-(2-pyridin-2-yl-5,6-dihydro-4H-pyrrolo[1,2-b]pyrazol-3-yl)-quinoline |
| 232 | [4-(2-pyridin-2-yl-5,6-dihydro-4H-pyrrolo[1,2-b]pyrazol-3-yl)-quinolin-7-yloxy]-acetic acid ethyl ester |
| 233 | 2-methoxy-4-(2-(pyridin-2-yl)-5,6-dihydro-4H-pyrrolo[1,2-b]pyrazol-3-yl)quinolone |
| 234 | dimethyl-{2-[4-(2-pyridin-2-yl-5,6-dihydro-4H-pyrrolo[1,2-b]pyrazol-3-yl)-quinolin-7-yloxy]-ethyl}-amine |
| 235 | 4-{[4-(5,6-Dimethyl-2-pyridin-2-yl-pyridin-3-yl)oxypyridin-2-yl]amino}-N,Ndimethyl-benzamide |
| 236 | 4-(5,6-Dimethyl-2-pyridin-2-yl-pyridin-3-yl)oxy-N-(3-methoxyphenyl)pyridin-2-amine |
| 237 | 4-(5,6-Dimethyl-2-pyridin-2-yl-pyridin-3-yl)oxy-N-(2-morpholin-4-ylphenyl)pyridin-2-amine |
| 238 | 4-(5,6-Dimethyl-2-pyridin-2-yl-pyridin-3-yl)oxy-N-(2-methoxyphenyl)pyridin-2-amine |
| 239 | 4-{[4-(5,6-Dimethyl-2-pyridin-2-yl-pyridin-3-yl)oxypyridin-2-yl]amino}benzenesulfonamide |
| 240 | 4-(2-Methylpyridin-3-yl)oxy-N-(3,4,5-trimethoxyphenyl)-pyridin-2-amine |
| 241 | 4-(2-Methylpyridin-3-yl)oxy-N-(3,4,5-trimethoxyphenyl)-pyridin-2-amine |
| 242 | 4-(5,6-Dimethyl-2-pyridin-2-yl-pyridin-3-yl)oxy-N-(4-methoxyphenyl)pyridin-2-amine |
| 243 | 4-(5,6-Dimethyl-2-pyridin-2-yl-pyridin-3-yl)oxy-N-(2-methoxyphenyl)pyridin-2-amine |
| 244 | 4-(2,6-Dimethylpyridin-3-yl)oxy-N-(3,4,5-trimethoxyphenyl)-pyridin-2-amine |
| 245 | 4-({4-[(2,6-Dimethylpyridin-3-yl)oxy]pyridin-2-yl}amino)benzenesulfonamide |
| 246 | 4-(5,6-Dimethyl-2-pyridin-2-yl-pyridin-3-yl)oxy-N-(4-morpholin-4-ylphenyl)pyridin-2-amine |
| 247 | 4-[5,6-dimethyl-2,2'-bipyridin-3-yl-oxy]-N-(3,4,5-trimethyloxyphenyl)pyridine-2-amine |
| 248 | 4-(5,6-Dimethyl-2-pyridin-2-yl-pyridin-3-yl)oxy-N-(4-morpholin-4-ylphenyl)pyridin-2-amine |
| 249 | 4-Pyridin-3-yloxy-N-(3,4,5-trimethoxyphenyl)pyridin-2-amine |
| 250 | 4-(6-Methyl-2-pyridin-2-yl-pyridin-3-yl)oxy-N-(3,4,5-trimethoxyphenyl)pyridin-2-amine |
| 251 | 4-{[4-(5,6-Dimethyl-2-pyridin-2-yl-pyridin-3-yl)oxypyridin-2-yl]amino}benzenesulfonamide |

TABLE 2-continued

| Designation | Compound Name |
|---|---|
| 252 | 4-(2,6-Dimethylpyridin-3-yl)oxy-N-(3,4,5-trimethoxyphenyl)-pyridin-2-amine |
| 253 | 4-(6-Methylpyridin-3-yl)oxy-N-(3,4,5-trimethoxyphenyl)-pyridin-2-amine |
| 254 | 4-(5,6-Dimethyl-2-pyridin-2-yl-pyridin-3-yl)oxy-N-(3-morpholin-4-ylphenyl)pyridin-2-amine |
| 255 | 4-({4-[(2,6-Dimethylpyridin-3-yl)oxy]pyridin-2-yl}amino)benzenesulfonamide |
| 256 | 4-(5,6-Dimethyl-2-pyridin-2-yl-pyridin-3-yl)oxy-N-(4-methoxyphenyl)pyridin-2-amine |
| 257 | 4-(5,6-Dimethyl-2-pyridin-2-yl-pyridin-3-yl)oxy-N-(4-fluorophenyl)pyridin-2-amine |
| 258 | 4-(6-Methylpyridin-3-yl)oxy-N-(3,4,5-trimethoxyphenyl)-pyridin-2-amine |
| 259 | 4-(6-Methyl-2-pyridin-2-yl-pyridin-3-yl)oxy-N-(3,4,5-trimethoxyphenyl)pyridin-2-amine |
| 260 | 5-(6-Ethoxy-[1,5]naphthyridin-2-yl)-4-pyridin-2-yl-thiazol-2-ylamine |
| 261 | 4-(3-chlorophenyl)-5-(1,5-naphthyridin-2-yl)thiazol-2-amine |
| 262 | 4-(4-fluorophenyl)-5-(1,5-naphthyridin-2-yl)thiazol-2-amine |
| 263 | 5-(6-Ethoxy-[1,5]naphthyridin-2-yl)-4-pyridin-2-yl-thiazol-2-ylamine |
| 264 | 4-(6-Methyl-pyridin-2-yl)-5-[1,5]naphthyridin-2-yl-thiazol-2-ylamine |
| 265 | 5-(1,5-naphthyridin-2-yl)-4-(pyridin-2-yl)thiazol-2-amine |
| 266 | 4-(3-chlorophenyl)-5-(1,5-naphthyridin-2-yl)thiazol-2-amine |
| 267 | 4-(4-fluorophenyl)-5-(1,5-naphthyridin-2-yl)thiazol-2-amine |
| 268 | 4-(3-chlorophenyl)-5-(1,5-naphthyridin-2-yl)thiazol-2-amine |
| 269 | 5-(6-methyl-1,5-naphthyridin-4-yl)-4-(pyridin-2-yl)thiazol-2-amine |
| 270 | 5-[1,8]Naphthyridin-4-yl-4-pyridin-2-yl-thiazol-2-ylamine |
| 271 | 5-(1,5-naphthyridin-2-yl)-4-(pyridin-2-yl)thiazol-2-amine |
| 272 | 5-(8-Methyl-[1,5]naphthyridin-2-yl)-4-pyridin-2-yl-thiazol-2-ylamine |
| 273 | 5-(6-methyl-1,5-naphthyridin-4-yl)-4-(pyridin-2-yl)thiazol-2-amine |
| 274 | 4-(3-methylpyridin-2-yl)-5-(1,5-naphthyridin-2-yl)thiazol-2-amine |
| 275 | 5[1,8]Naphthyridin-4-yl-4-pyridin-2-yl-thiazol-2-ylamine |
| 276 | 4-[5-Benzo[1,3]dioxol-5-yl-4-(6-ethyl-pyridin-2-yl)-1H-imidazol-2-yl]-bicylo[2.2.2]octane-1-carboxylic acid amide |
| 277 | 4-[5-Benzo[1,3]dioxol-5-yl-4-(6-ethyl-pyridin-2-yl)-1H-imidazol-2-yl]-bicylo[2.2.2]octane-1-carboxylic acid |
| 278 | 4-[5,6-dihydro-2-(2-pyridinyl)-4H-pyrrolo[1,2-b]pyrazol-3-yl]-7-[2-(4-morpholinyl)ethoxy]-quinoline |
| 279 | 4-[5,6-dihydro-2-(6-methyl-2-pyridinyl)-4H-pyrrolo[1,2-b]pyrazol-3-yl]-6-quinolinecarboxamide |
| 280 | 2-(5-Chloro-2-fluorophenyl)-4-[(4-pyridyl)amino]pteridine |
| 281 | 2-(5-benzo[1,3]dioxol-5-yl-2-tert-butyl-3H-imidazol-4-yl)-6-methylpyridine hydrochloride |
| 282 | 4-(5-benzo[1,3]dioxol-5-yl-4-pyridin-2-yl-1H-imidazol-2-yl)-benzamide |
| 283 | [3-(pyridin-2yl)-4-(4-quinonyl)]-1H pyrazole |

The preparation and use of ALK5 inhibitors is well-known and well-documented in the scientific and patent literature. PCT publication no. WO 2000/61576 and U.S. patent publication no. US 2003/0149277 disclose triarylimidazole derivatives and their use as ALK5 inhibitors. PCT publication no. WO 2001/62756 discloses pyridinylimidazole derivatives and their use as ALK5 inhibitors. PCT publication no. WO 2002/055077 discloses use of imidazolyl cyclic acetal derivatives as ALK5 inhibitors. PCT publication no. WO 2003/087304 discloses tri-substituted heteroaryls and their use as ALK5 and/or ALK4 inhibitors. WO 2005/103028, U.S. patent publication no. US 2008/0319012 and U.S. Pat. No. 7,407,958 disclose 2-pyridyl substituted imidazoles as ALK5 and/or ALK4 inhibitors. One of the representative compounds, IN-1130, shows ALK5 and/or ALK4 inhibitor activity in several animal models. The following patents and patent publications provide additional examples of ALK5 inhibitors and provide illustrative synthesis schemes and methods of using ALK5 inhibitors: U.S. Pat. Nos. 6,465,493; 6,906,089; 7,365,066; 7,087,626; 7,368,445; 7,265,225; 7,405,299; 7,407,958; 7,511,056; 7,612,094; 7,691,865; 7,863,288; 8,410,146; 8,410,146; 8,420,685; 8,513,2228,614,226; 8,791,113; 8,815,893; 8,846,931; 8,912,216; 8,987,301; 9,051,307; 9,051,318; 9,073,918 and PCT publication nos. WO 2004/065392; WO 2009/050183; WO 2009/133070; WO 2011/146287; and WO 2013/009140. The foregoing patents and patent publications are incorporated by reference in their entirety.

Several ALK5 inhibitors are commercially available, including SB-525334 (CAS 356559-20-1), 5B-505124 (CAS 694433-59-5), 5B-431542 (CAS 301836-41-9), 5B-202474 (EMD4 Biosciences Merck KGaA, Darmstadt, Germany), LY-364947 (CAS 396129-53-6), IN-1130, GW-788388 and D4476 (EMD4 Biosciences Merck KGaA, Darmstadt, Germany).

The structures and names of ALK5 inhibitors described herein refer to the molecule prior to the attachment to the antibody and/or linker.

Preferred ALK5 inhibitors are those which can be attached to a linker via a free NH or $NH_2$ group, preferably an NH or $NH_2$ group attached to or part of an alkyl, heteroaryl, or aryl group (e.g., as in Compounds 1-23, 26-29, 31, 35, 37, 39, 40, 42, 43, 45-48, 50-85, 87-90, 93, 96, 98-104, 106, 108, 109, 111, 112, 114, 116-120, 132, 146, 149, 156, 184, 187, 193, 218, 260-277, 282, and 283 shown in Table 2). ALK5 inhibitors can be derivatized to add a free NH or $NH_2$ group. Design of derivatized ALK5 inhibitors should preferably take into account the inhibitors' structure activity relationships (SAR) to reduce the likelihood of abolishing inhibitory activity when adding an NH or $NH_2$ group, although the activity may also be determined empirically. Exemplary derivatized counterparts of several compounds shown in Table 1 are shown below in Table 3.

TABLE 3
| Table 1 Designation | Derivative 1 |
|---|---|
| A | 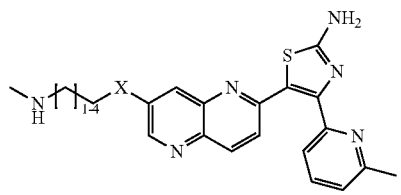<br>X = O, NH |
| E | 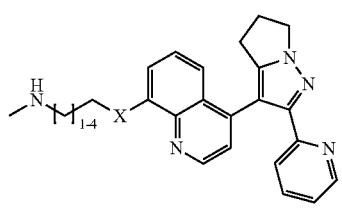<br>X = O, NH |
| F | 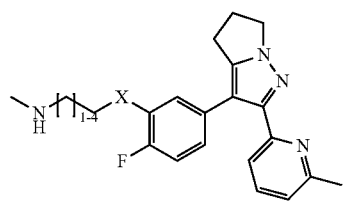<br>X = O, NH |
| H | 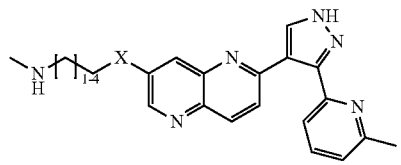<br>X = O, NH |
| L | 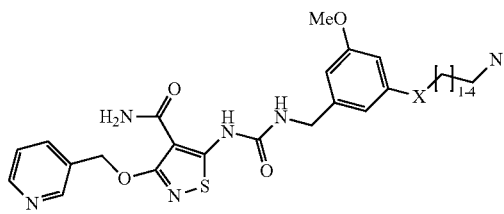<br>X = O, NH |
| M | 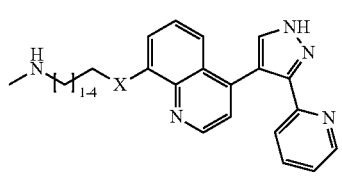<br>X = O, NH |

TABLE 3-continued

| Table 1 Designation | Derivative 2 |
|---|---|
| A | 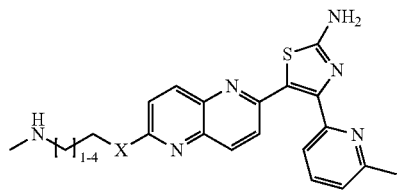<br>X = O, NH |
| E | 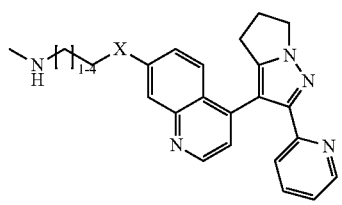<br>X = O, NH |
| F<br>H | 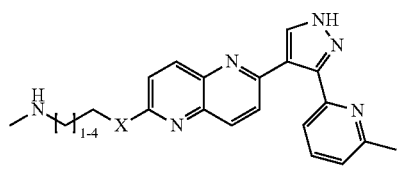<br>X = O, NH |
| L<br>M | 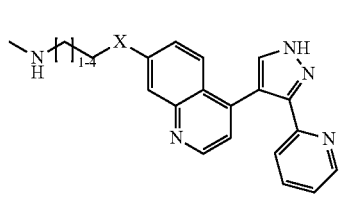<br>X = O, NH |

5.4. Linkers

Typically, the ADCs comprise a linker between the ALK5 inhibitor and the antibody. Linkers are moieties comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —$(CR_2)_nO(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

A linker may comprise one or more linker components, such as stretcher and spacer moieties. For example, a peptidyl linker can comprise a peptidyl component of two or more amino acids and, optionally, one or more stretcher and/or spacer moieties. Various linker components are known in the art, some of which are described below.

A linker may be a "cleavable linker," facilitating release of a drug in the cell. For example, an acid-labile linker (e.g., hydrazone), protease-sensitive (e.g., peptidase-sensitive) linker, photolabile linker, dimethyl linker or disulfide-containing linker (Chari et al., 1992, Cancer Research 52:127-131; U.S. Pat. No. 5,208,020) may be used.

Examples of linkers and linker components known in the art include aleimidocaproyl (mc); maleimidocaproyl-p-aminobenzylcarbamate; maleimidocaproyl-peptide-aminobenzylcarbamate linkers, e.g., maleimidocaproyl-L-phenylalanine-L-lysine-p-aminobenzylcarbamate and maleimidocaproyl-L-valine-L-citrulline-p-aminobenzylcarbamate (vc); N-succinimidyl 3-(2-pyridyldithio)proprionate (also known as N-succinimidyl 4-(2-pyridyldithio)pentanoate or SPP); 4-succinimidyl-oxycarbonyl-2-methyl-2-(2-pyridyldithio)-toluene (SMPT); N-succinimidyl 3-(2-pyridyldithio)propionate (SPDP); N-succinimidyl 4-(2-pyridyldithio)butyrate (SPDB); 2-iminothiolane; S-acetylsuccinic anhydride; disulfide benzyl carbamate; carbonate; hydrazone linkers; N-(α-Maleimidoacetoxy)succinimide ester; N-[4-(p-Azidosalicylamido)butyl]-3'-(2'-pyridyldithio)propionamide (AMAS); N[β-Maleimidopropyloxy]succinimide ester (BMPS); [N-ε-Maleimidocaproyloxy]succinimide ester (EMCS); N-[γ-

Maleimidobutyryloxy]succinimide ester (GMBS); Succinimidyl-4-[N-Maleimidomethyl]cyclohexane-1-carboxy-[6-amidocaproate] (LC-SMCC); Succinimidyl 6-(3-[2-pyridyldithio]-propionamido)hexanoate (LC-SPDP); m-Maleimidobenzoyl-N-hydroxysuccinimide ester (MBS); N-Succinimidyl[4-iodoacetyl]aminobenzoate (STAB); Succinimidyl 4-[N-maleimidomethyl]cyclohexane-1-carboxylate (SMCC); N-Succinimidyl 3-[2-pyridyldithio]-propionamido (SPDP); [N-ε-Maleimidocaproyloxy]sulfosuccinimide ester (Sulfo-EMCS); N-[γ-Maleimidobutyryloxy]sulfosuccinimide ester (Sulfo-GMBS); 4-Sulfosuccinimidyl-6-methyl-α-(2-pyridyldithio)toluamidoThexanoate-) (Sulfo-LC-SMPT); Sulfosuccinimidyl 6-(3'-[2-pyridyldithio]-propionamido)hexanoate (Sulfo-LC-SPDP); m-Maleimidobenzoyl-N-hydroxysulfosuccinimide ester (Sulfo-MBS); N-Sulfosuccinimidyl[4-iodoacetyl]aminobenzoate (Sulfo-SIAB); Sulfosuccinimidyl 4-[N-maleimidomethyl]cyclohexane-1-carboxylate (Sulfo-SMCC); Sulfosuccinimidyl 4-[p-maleimidophenyl]butyrate (Sulfo-SMPB); ethylene glycol-bis(succinic acid N-hydroxysuccinimide ester) (EGS); disuccinimidyl tartrate (DST); 1,4,7,10-tetraazacyclododecane-1,4,7,10-tetraacetic acid (DOTA); diethylenetriamine-pentaacetic acid (DTPA); thiourea linkers; and oxime containing linkers.

In some embodiments, the linker is cleavable under intracellular or extracellular conditions, such that cleavage of the linker releases the ALK5 inhibitor from the antibody in the appropriate environment. In yet other embodiments, the linker is not cleavable and the drug is released, for example, by antibody degradation in lysosomes (see U.S. patent publication 2005/0238649 incorporated by reference herein in its entirety and for all purposes).

Examples of non-cleavable linkers that can be used in the ADCs of the disclosure include N-maleimidomethylcyclohexanel-carboxylate, maleimidocaproyl or mercaptoacetamidocaproyl linkers.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker comprises a peptidyl component that is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). For example, a peptidyl linker that is cleavable by the thiol-dependent protease cathepsin-B (e.g., a Phe-Leu or a Gly-Phe-Leu-Gly linker). Other examples of such linkers are described, e.g., in U.S. Pat. No. 6,214,345, incorporated herein by reference in its entirety and for all purposes.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SM PT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of ADC, are cleaved when the ADC presents in an extracellular environment (for example, in plasma).

Whether a linker is not substantially sensitive to the extracellular environment can be determined, for example, by incubating with plasma the ADC for a predetermined time period (for example, 2, 4, 8, 16, or 24 hours) and then quantitating the amount of free drug present in the plasma.

In other, non-mutually exclusive embodiments, the linker can promote cellular internalization. In certain embodiments, the linker promotes cellular internalization when conjugated to the therapeutic agent (that is, in the milieu of the linker-therapeutic agent moiety of the ADC as described herein). In yet other embodiments, the linker promotes cellular internalization when conjugated to both the ALK5 inhibitor and the antibody.

In many embodiments, the linker is self-immolative. As used herein, the term "self-immolative" refers to a bifunctional chemical moiety that is capable of covalently linking together two spaced chemical moieties into a stable tripartite molecule. It will spontaneously separate from the second chemical moiety if its bond to the first moiety is cleaved. See for example, PCT publication nos. WO 2007/059404, WO 2006/110476, WO 2005/112919, WO 2010/062171, WO 2009/017394, WO 2007/089149, WO 2007/018431, WO 2004/043493 and WO 2002/083180, which are directed to drug-cleavable substrate conjugates where the drug and cleavable substrate are optionally linked through a self-immolative linker and which are all expressly incorporated by reference. Examples of self-immolative spacer units that can be used to generated self-immolative linkers are described under Formula I below.

A variety of exemplary linkers that can be used with the present compositions and methods are described in PCT publication no. WO 2004/010957, U.S. patent publication no. US 2006/0074008, U.S. patent publication no. US 2005/0238649, and U.S. patent publication no. US 2006/0024317

(each of which is incorporated by reference herein in its entirety and for all purposes).

An ADC of the disclosure may be of Formula I, below, wherein an antibody (Ab) is conjugated to one or more ALK5 inhibitor drug moieties (D) through an optional linker (L)

Accordingly, the antibody may be conjugated to the drug either directly or via a linker. In Formula I, p is the average number of drug (i.e., ALK5 inhibitor) moieties per antibody, which can range, e.g., from about 1 to about 20 drug moieties per antibody, and in certain embodiments, from 2 to about 8 drug moieties per antibody. Further details of drug loading are described in Section 5.5 below.

In some embodiments, a linker component may comprise a "stretcher" that links an antibody e.g., via a cysteine residue, to another linker component or to a drug moiety. Exemplary stretchers are shown below (wherein the left wavy line indicates the site of covalent attachment to an antibody and the right wavy line indicates the site of covalent attachment to another linker component or drug moiety):

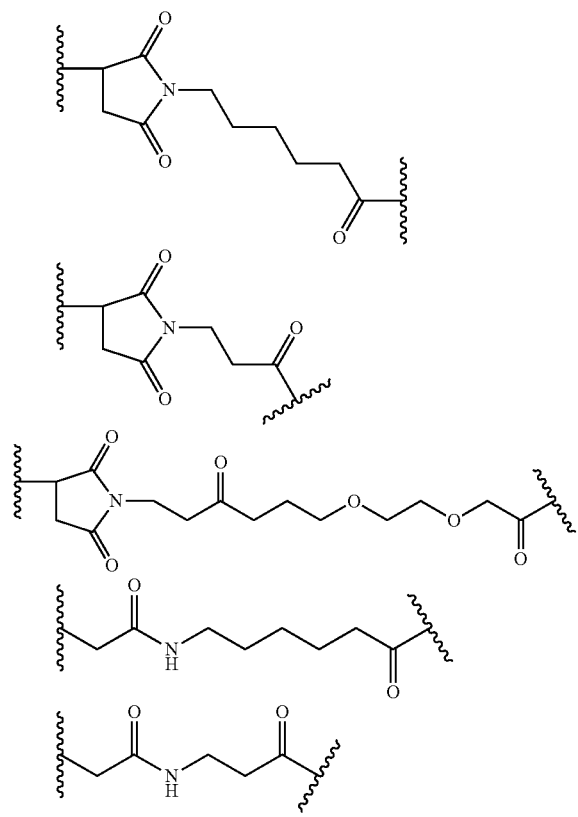

See, U.S. Pat. No. 9,109,035; Ducry et al., 2010, Bioconjugate Chem. 21:5-13.

In some embodiments, a linker component may comprise an amino acid unit. In one such embodiment, the amino acid unit allows for cleavage of the linker by a protease, thereby facilitating release of the drug from the ADC upon exposure to intracellular proteases, such as lysosomal enzymes. See, e.g., Doronina et al., 2003, Nat. Biotechnol. 21:778-784. Exemplary amino acid units include, but are not limited to, a dipeptide, a tripeptide, a tetrapeptide, and a pentapeptide. Exemplary dipeptides include: valine-citrulline (VC or val-cit), alanine-phenylalanine (AF or ala-phe); phenylalanine-lysine (FK or phe-lys); or N-methyl-valine-citrulline (Me-val-cit). Exemplary tripeptides include: glycine-valine-citrulline (gly-val-cit) and glycine-glycine-glycine (gly-gly-gly). An amino acid unit may comprise amino acid residues that occur naturally, as well as minor amino acids and non-naturally occurring amino acid analogs, such as citrulline amino acid units can be designed and optimized in their selectivity for enzymatic cleavage by a particular enzyme, for example, cathepsin B, C and D, or a plasmin protease.

In some embodiments, a linker component may comprise a "spacer" unit that links the antibody to a drug moiety, either directly or by way of a stretcher and/or an amino acid unit. A spacer unit may be "self-immolative" or a "non-self-immolative." A "non-self-immolative" spacer unit is one in which part or all of the spacer unit remains bound to the drug moiety upon enzymatic (e.g., proteolytic) cleavage of the ADC. Examples of non-self-immolative spacer units include, but are not limited to, a glycine spacer unit and a glycine-glycine spacer unit. A "self-immolative" spacer unit allows for release of the drug moiety without a separate hydrolysis step. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. See, e.g., Hamann et al., 2005, Expert Opin. Ther. Patents 15:1087-1103. In one embodiment, the spacer unit is p-aminobenzyloxycarbonyl (PAB). In certain embodiments, the phenylene portion of a p-amino benzyl unit is substituted with $Q_m$, wherein Q is —$C_1$-$C_8$ alkyl, —O—($C_1$-$C_8$ alkyl), -halogen, -nitro or -cyano; and m is an integer ranging from 0-4. Examples of self-immolative spacer units further include, but are not limited to, aromatic compounds that are electronically similar to p-aminobenzyl alcohol (see, e.g., U.S. patent publication no. US 2005/0256030), such as 2-aminoimidazol-5-methanol derivatives (Hay et al., 1999, Bioorg. Med. Chem. Lett. 9:2237) and ortho- or para-aminobenzylacetals. Spacers can be used that undergo cyclization upon amide bond hydrolysis, such as substituted and unsubstituted 4-aminobutyric acid amides (Rodrigues et al., 1995, Chemistry Biology 2:223); appropriately substituted bicyclo[2.2.1] and bicyclo[2.2.2] ring systems (Storm et al., 1972, Amer. Chem. Soc. 94:5815); and 2-aminophenylpropionic acid amides (Amsberry et al., 1990, J. Org. Chem. 55:5867). Elimination of amine-containing drugs that are substituted at the a-position of glycine (Kingsbury et al., 1984, J. Med. Chem. 27:1447) are also examples of self-immolative spacers useful in ADCs.

In one embodiment, a spacer unit is a branched bis (hydroxymethyl)styrene (BHMS) unit as depicted below, which can be used to incorporate and release multiple drugs.

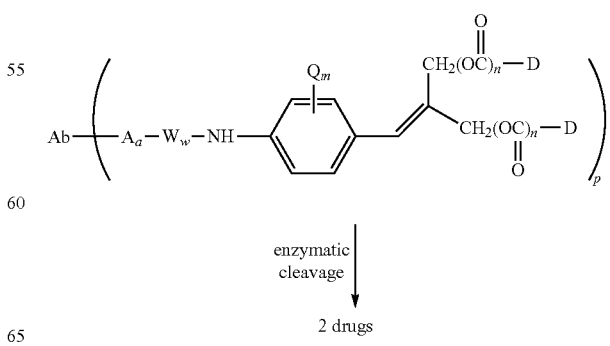

wherein Ab and D are defined as above for Formula I; A is a stretcher, and a is an integer from 0 to 1; W is an amino acid unit, and w is an integer from 0 to 12; Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to about 20.

A linker may comprise any one or more of the above linker components. In certain embodiments, a linker is as shown in brackets in the following ADC formula:

Ab-(-[A$a$-W$w$-Y$y$]-D)$_p$  II wherein Ab, A, a, W, w, D, and p are as defined in the preceding paragraph; Y is a spacer unit, and y is 0, 1, or 2; and. Exemplary embodiments of such linkers are described in U.S. patent publication no. 2005/0238649 A1, which is incorporated herein by reference.

Exemplary linker components and combinations thereof are shown below in the context of ADCs of Formula II:

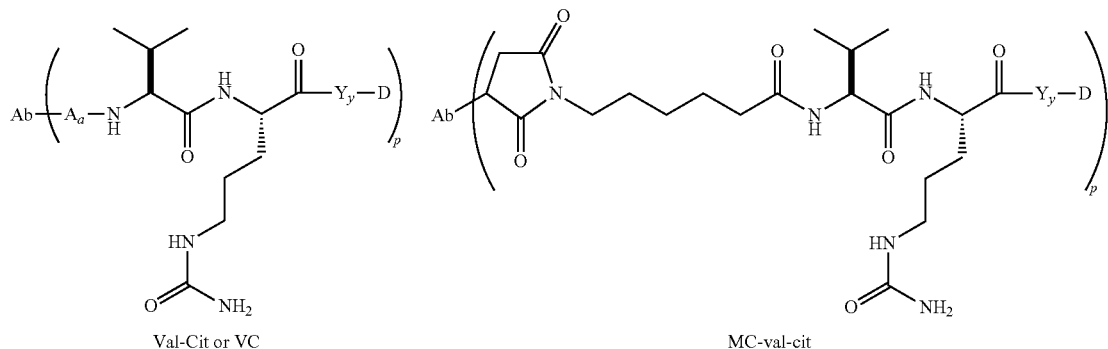

Val-Cit or VC

MC-val-cit

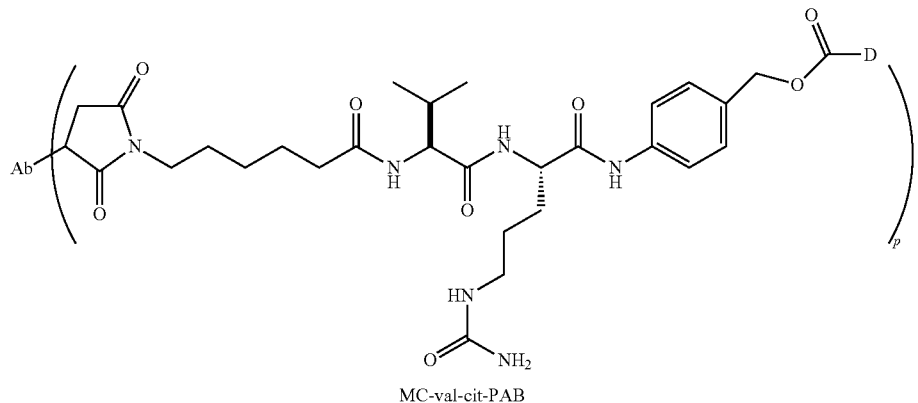

MC-val-cit-PAB

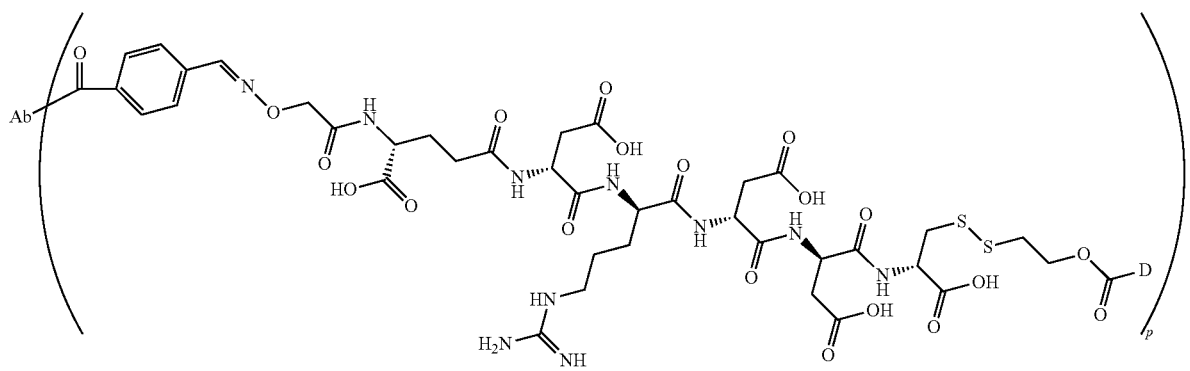

Linkers components, including stretcher, spacer, and amino acid units, may be synthesized by methods known in the art, such as those described in U.S. patent publication no. 2005/0238649.

5.5. Drug Loading

Drug loading is represented by p and is the average number of ALK5 inhibitor moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, ALK5 inhibitor loading averages from 2 to 8 drug moieties per antibody, more preferably 2 to 4 drug moieties per antibody or 5 to 7 drug moieties per antibody.

As would be understood by one of skill in the art, in many instances references to an ADC is shorthand for a population or collection of ADC molecules (sometimes in the context of a pharmaceutical composition), each molecule composed of an antibody covalently attached to one or more ALK5 inhibitor moieties, with the drug loading ratio representing the average drug loading in the population or collection, although the ratio on an individual molecule basis may vary from one ADC molecule to another in the population. In some embodiments, the population or collection contains ADC molecules comprising an antibody covalently attached to anywhere between 1 and 30 drug moieties, and in some embodiments anywhere between 1 and 20, between 1 and 15, between 2 and 12 or between 2 and 8 drug moieties. Preferably, the average in the population is as described in the preceding paragraph, e.g., 2 to 8 drug moieties per antibody, more preferably 4 to 8 drug moieties per antibody or 5 to 7 drug moieties per antibody.

Some ADC populations can be in the form of compositions comprising ADCs as described herein and antibody molecules lacking drug moieties, e.g., antibodies to which attachment of the ALK5 antibody was unsuccessful.

The average number of ALK5 inhibitor moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other ALK5 inhibitor loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g., p>5, may cause aggregation, insolubility, toxicity, or loss of cellular permeability of certain antibody-drug conjugates. In certain embodiments, the drug loading for an ADC of the disclosure ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See U.S. patent publication no. US 2005/0238649 (herein incorporated by reference in its entirety).

In certain embodiments, less than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed in PCT publication no. WO 2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

5.6. Formulations and Administration

Suitable routes of administration of the ADCs include, without limitation, oral, parenteral, rectal, transmucosal, intestinal administration, intramedullary, intrathecal, direct intraventricular, intravenous, intravitreal, intracavitary, intraperitoneal, or intratumoral injections. The preferred routes of administration are parenteral, more preferably intravenous. Alternatively, one may administer the compound in a local rather than systemic manner, for example, via injection of the compound directly into a solid or hematological tumor.

Immunoconjugates can be formulated according to known methods to prepare pharmaceutically useful compositions, whereby the ADC is combined in a mixture with a pharmaceutically suitable excipient. Sterile phosphate-buffered saline is one example of a pharmaceutically suitable excipient. Other suitable excipients are well-known to those in the art. See, for example, Ansel et al., Pharmaceutical Dosage Forms And Drug Delivery Systems, 5th Edition (Lea & Febiger 1990), and Gennaro (ed.), Remington's Pharmaceutical Sciences, 18th Edition (Mack Publishing Company 1990), and revised editions thereof.

In a preferred embodiment, the ADC is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino)ethanesulfonic acid (MES); 3-(N-morpholino)propanesulfonic acid (MOPS); 3-(N-morpholinyl)-2-hydroxypropanesulfonic acid (MOPSO); and piperazine-N,N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The ADC can be formulated for intravenous administration via, for example, bolus injection, slow infusion or continuous infusion. Preferably, the ADC is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the ADC. Control release preparations can be prepared through the use of polymers to complex or adsorb the ADC. For example, biocompatible polymers include matrices of poly(ethylene-co-vinyl acetate) and matrices of a polyanhydride copolymer of a stearic acid dimer and sebacic acid. Sherwood et al., 1992, Bio/Technology 10:1446. The rate of release of an ADC from such a matrix depends upon the molecular weight of the ADC, the amount of ADC within the matrix, and the size of dispersed particles. Saltzman et al., 1989, Biophys. J. 55:163; Sherwood et al., supra. Other solid dosage forms are described in Ansel et al., Pharmaceutical Dosage Forms And Drug Delivery Systems, 5th Edition (Lea & Febiger 1990), and Gennaro (ed.), Remington's Pharmaceutical Sciences, 18th Edition (Mack Publishing Company 1990), and revised editions thereof.

Generally, the dosage of an administered ADC for humans will vary depending upon such factors as the patient's age, weight, height, sex, general medical condition and previous medical history. It may be desirable to provide the recipient with a dosage of ADC that is in the range of from about 0.3 mg/kg to 5 mg/kg as a single intravenous infusion, although a lower or higher dosage also may be administered as circumstances dictate. A dosage of 0.3-5 mg/kg for a 70 kg patient, for example, is 21-350 mg, or 12-20$^6$ mg/m$_2$ for a 1.7-m patient. The dosage may be repeated as needed, for example, once per week for 2-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 0.3 mg/kg, 0.5 mg/kg, 0.7 mg/kg, 1.0 mg/kg, 1.2 mg/kg, 1.5 mg/kg, 2.0 mg/kg, 2.5 mg/kg, 3.0 mg/kg, 3.5 mg/kg, 4.0 mg/kg, 4.5 mg/kg, and 5.0 mg/kg. More preferred dosages are 0.6 mg/kg for weekly administration and 1.2 mg/kg for less frequent dosing. Any amount in the range of 0.3 to 5 mg/kg may be used. The dosage is preferably administered multiple times, once a week. A minimum dosage schedule of 4 weeks, more preferably 8 weeks, more preferably 16 weeks or longer may be used, with the dose frequency dependent on toxic side-effects and recovery therefrom, mostly related to hematological toxicities. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 2, 4, 6, 8, 10, or 12 times or more.

Alternatively, an ADC may be administered as one dosage every 2 or 3 weeks, repeated for a total of at least 3 dosages. Or, twice per week for 4-6 weeks. The dosage may be administered once every other week or even less frequently, so the patient can recover from any drug-related toxicities. Alternatively, the dosage schedule may be decreased, namely every 2 or 3 weeks for 2-3 months. The dosing schedule can optionally be repeated at other intervals and dosage may be given through various parenteral routes, with appropriate adjustment of the dose and schedule.

5.7. Methods of Treatment

The ADCs of the disclosure can be used for the treatment of various cancers. The ADCs can be used as monotherapy or as part of a combination therapy regimen, for example with a standard of care agent or regimen. Suitable antibodies for inclusion in ADCs for treatment of cancers are those that target surface antigens of T cells. Exemplary antibodies are described in Section 5.2.

Examples of cancers which can be treated using the ADCs of the disclosure include but not limited to pancreatic cancer, glioblastoma, myelodysplastic syndromes, prostate cancer, hepatocellular carcinoma, melanoma, and breast cancers.

For treatment of melanomas carrying a BRAF mutation, the ADCs of the disclosure can be used in combination with drugs that specifically target the BRAF mutations, such as venurafenibm, dabrafenib and trametinib.

For treatment of malignant melanomas, the ADCs of the disclosure can be used in combination with a checkpoint inhibitor, such as ipilimumab or nivolumab or pembrolizumab.

For treatment of non-small-cell lung carcinoma (NSCLC), the ADCs of the disclosure can be used in combination with standard of care chemotherapy treatments such as cisplatin, carboplatin, paclitaxel, gemcitabine, vinorelbin, irinotecan, etoposide, or vinblastine would be included. In addition, the ADCs can be used in combination with targeted therapies, such as bevacizumab or Erbitux.

For treatment of bladder cancer, the ADCs of the disclosure can be used in combination with standard of care treatments, including but not limited to cisplatin, mitomycin-C, carboplatin, docetaxel, paclitaxel, doxorubicin, 5-FU, methotrexate, vinblastine, ifosfamide, and pemetrexed.

For treatment of renal cancer, the ADCs of the disclosure can be used in combination with standard of care treatments, for example agents that block angiogenesis and/or specific tyrosine kinases, such as sorafenib, sunitinib, temsirolimus, everolimus, pazopanib, and axitinib.

For treatment of breast cancer, the ADCs of the disclosure can be used in combination with standard of care chemotherapeutic agents, such as the anthracyclines (doxorubicin or epirubicin) and the taxanes (paclitaxel or docetaxel), as well as fluorouracil, cyclophosphamide and carboplatin. In addition, the ADCs of the disclosure can be used in combination with targeted therapies. Targeted therapies for HER2/neu positive tumors include trastuzumab and pertuzumab and for estrogen receptor (ER) positive tumors include tamoxifen, toremifene and fulvestrant.

For pancreatic cancer, the ADCs of the disclosure can be used in combination with standard of care chemotherapeutic agents, such as gemcitabine, 5-fluouracil, irinotecan, oxaliplatin, paclitaxel, capecitabine, cisplatin, or docetaxel. In addition, ADCs can be used in combination with targeted therapies, such as erlotinib, which inhibits EGFR.

For glioblastoma, the ADCs of the disclosure can be used in combination with standard of care chemotherapeutic agents, such as carboplatin, cyclophosphamide, etoposide, lomustine, methotrexate or procarbazine.

For prostate cancer, the ADCs of the disclosure can be used in combination with standard of care chemotherapeutic agents, including docetaxel, optionally with the steroid prednisone, or cabazitaxel.

6. EXAMPLES

The following abbreviations are found throughout the Examples:

Boc—tert-butyloxycarbonyl
DCM—dichloromethane
DMA—dimethylamine
DMF—dimethylformamide
DIPEA—N,N-Diisopropylethylamine
EtOAc—ethyl acetate
EtOH—ethanol
Fmoc—Fluorenylmethyloxycarbonyl
HOBt—Hydroxybenzotriazole
MeOH—methanol
NaHMDS—sodium hexamethyldisilazide
RT—room temperature, approximately 21° C.
TBTU—O-(Benzotriazol-1-yl)-N,N,N',N'-tetramethyluronium tetrafluoroborate
TEA—triethylamine
THF—tetrahyrdrofuran
TFA—trifluoroacetic acid
TMS-imidazole—1-(Trimethylsilyl)imidazole

6.1. Example 1: Synthesis of 4-(6-methylpyridin-2-yl)-5-(1,5-naphthyridin-2-yl)-1,3-thiazol-2-amine (Compound A)

Compound A was prepared according to the general methodology in Scheme 1 below:

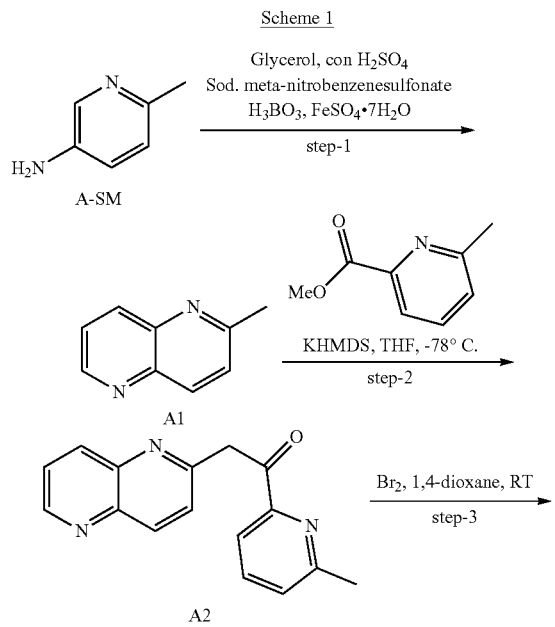

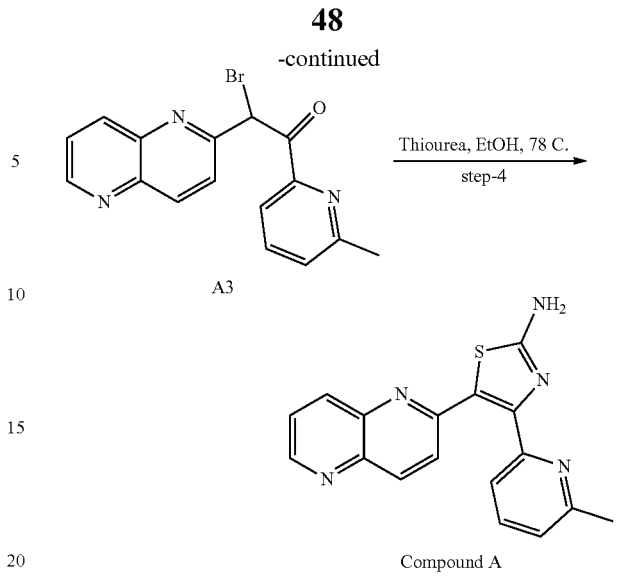

6.1.1. 2-methyl-1,5-naphthyridine (A1)

A mixture of concentrated sulfuric acid (2.5 ml), sodium m-nitrobenzenesulfonate (2.08 g, 9.24 mmol), boric acid (445 mg, 7.21 mmol) and ferrous sulfate heptahydrate (167 mg, 0.60 mmol) was stirred at room temperature. Glycerol (1.5 ml) followed by 5-Amino-2-methylpyridine (A-SM) (500 mg, 4.62 mmol) and water (2.5 ml) was added to the reaction mixture and heated at 135° C. for 18 h. After completion of the reaction as measured by TLC, the reaction mixture was cooled to approximately 21° C., basified using 4N NaOH and extracted with EtOAc (2×100 ml). The organic extracts were combined, washed with water (200 ml), dried over $Na_2SO_4$ and evaporated under reduced pressure to give the crude compound A1. The crude was purified by silica gel column chromatography using (2% MeOH/$CH_2Cl_2$) to afford compound A1 as a pale brown crystalline solid (200 mg, 30%).

$^1$H NMR (500 MHz, $CDCl_3$): δ 8.92 (d, J=3.0 Hz, 1H), 8.35 (d, J=9.0 Hz, 1H), 8.31 (d, J=5.9 Hz, 1H), 7.62 (dd, J=8.5, 4.5 Hz, 1H), 7.54 (d, J=5.9 Hz, 1H), 2.8 (s, 3H)

LC-MS (ESI): m/z 145 [M+H]$^+$

6.1.2. 1-(6-methylpyridin-2-yl)-2-(1,5-naphthyridin-2-yl)ethan-1-one (A2)

A solution of A1 (200 mg, 1.38 mmol) and methyl 6-methylpicolinate (209 mg, 1.38 mmol) in anhydrous THF (10 ml) was placed under $N_2$ atmosphere and cooled to −78° C. Potassium bis (trimethylsilyl) amide (0.5 M in toluene, 6.9 ml, 3.47 mmol) was added drop wise over a period of 5 min. The reaction mixture was stirred at −78° C. for 1 h and then warmed to approximately 21° C. and maintained for 20 h. After completion of the reaction (as measured by TLC), the reaction mixture was quenched with saturated ammonium chloride solution (20 ml). The aqueous layer was extracted with EtOAc (2×20 ml). The combined organic extracts were washed with water (100 ml), dried over $Na_2SO_4$ and evaporated to give the crude compound A2. The crude material was purified by column chromatography (1% MeOH/$CH_2Cl_2$) to afford compound A2 as an orange yellow solid (110 mg, 30.5%).

$^1$H NMR (400 MHz, $CDCl_3$: Enol form): δ 15.74 (brs, —OH), 8.69 (t, J=3.6, 1H), 8.12 (d, J=9.2 Hz, 1H), 8.06 (dd, J=8.4, 4.4 Hz, 2H), 7.82 (t, J=7.6 Hz, 1H), 7.55 (dd, J=8.4, 4.8 Hz, 1H) 7.45 (d, J=9.6 Hz, 1H), 7.3 (dd, J=7.6, 4.0 Hz, 1H), 7.16 (s, 1H), 2.75 (s, 3H)

LC-MS (ESI): m/z 264 [M+H]⁺

6.1.3. 4-(6-methylpyridin-2-yl)-5-(1,5-naphthyridin-2-yl)-1,3-thiazol-2-amine (Compound A)

A solution of A2 (110 mg, 0.418 mmol) in 1,4-Dioxane (10 ml) was treated with bromine (0.025 ml, 0.501 mmol). The resulting reaction mixture was stirred at approximately 21° C. for 1 h and then concentrated under reduced pressure to afford crude A3 (120 mg), which was carried to the next step without further purification. The crude A3 (120 mg) was dissolved in ethanol (15 ml). Thiourea (3.5 mg, 0.046 mmol) was then added and the reaction mixture was heated at 78° C. for 4 h (until complete consumption of starting material was observed by TLC). The reaction mixture was cooled to approximately 21° C. and ammonia solution (25%, 1.5 ml) was added with gentle stirring. The solvent was evaporated, and then the residue was dissolved in CH₂Cl₂ (2×20 ml) and washed with water (50.0 ml). The separated organic layer was then washed with 1N HCl (30 ml×2). The combined aqueous layer was basified with 35% aq. sodium hydroxide (20 ml) and extracted with CH₂Cl₂ (2×20 ml). The organic layer was dried over sodium sulfate and evaporated to give the crude Compound A. The crude Compound A was recrystallized from acetonitrile (2 ml) to afford purified Compound A as a yellow crystalline solid (35 mg, 49% yield over 2 steps).

¹H NMR (400 MHz, CDCl₃): δ 8.86 (dd, J=4.4, 1.6 Hz, 1H), 8.29 (t, J=8.4 Hz, 1H), 8.06 (d, J=9.2 Hz, 1H), 7.64 (t, J=7.6 Hz, 1H), 7.60-7.55 (m, 2H), 7.46 (d, J=8 Hz, 1H), 7.20 (d, J=7.6 Hz, 1H), 5.32 (brs, 2H), 2.57 (s, 3H)

LC-MS (ESI): m/z 320 [M+H]⁺

UPLC purity: 97.6%

6.2. Example 2: Synthesis of N-methyl-2-(4-{4-[3-(pyridin-2-yl)-1H-pyrazol-4-yl]pyridin-2-yl}phenoxy)ethan-1-amine (Compound B)

Compound B was prepared according to the general methodology in Scheme 2 below:

Scheme 2

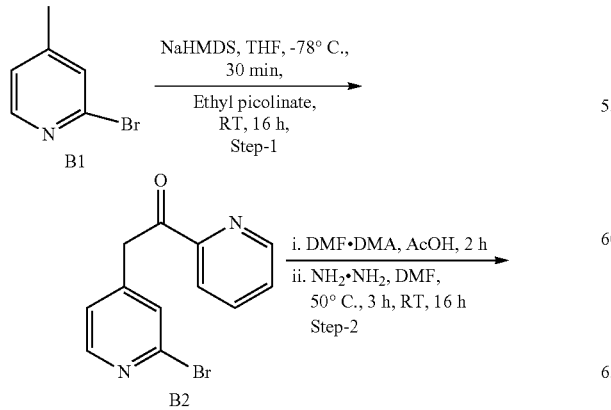

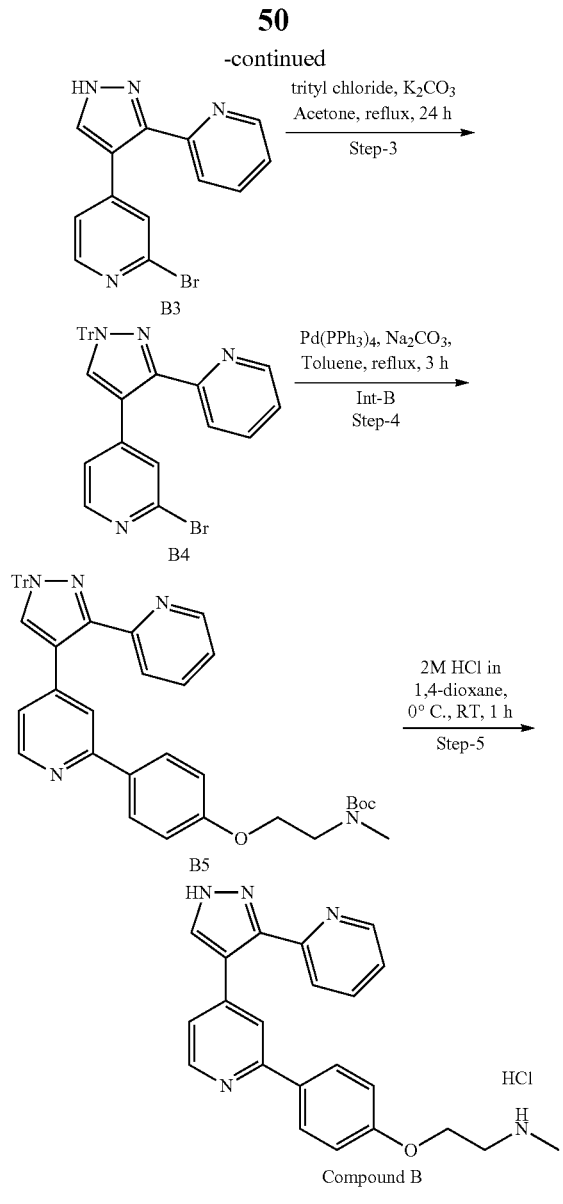

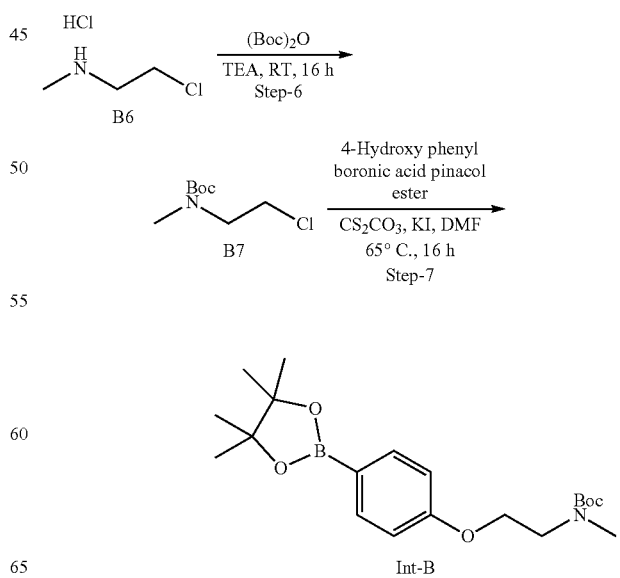

6.2.1. Tert-butyl (2-chloroethyl) (methyl) carbamate (B7)

To a stirred solution of Boc-anhydride (1.7 ml, 7.30 mmol) in THF (4 ml) were simultaneously added a solution of B6 (1 g, 7.69 mmol) in water (4 ml) and a solution of TEA (1 ml, 7.69 mmol) in THF (4 ml) over the course of 1 h. The resulting mixture was stirred at approximately 21° C. for 16 h. The reaction mixture was diluted with saturated NaCl solution (20 ml) and extracted with DCM (3×50 ml). The combined organic extracts were dried over $Na_2SO_4$, concentrated in vacuo to obtain the crude compound, which was purified by silica gel column chromatography using 10% EtOAc/Hexane to afford compound B7 as a pale yellow liquid (1 g, 5.18 mmol, 71%).

$^1$H NMR (400 MHz, $CDCl_3$): δ 3.58-3.52 (m, 4H), 2.93 (s, 3H), 1.46 (s, 9H)

6.2.2. Tert-butyl methyl (2-(4-(4,4,5,5-tetramethyl-1,3,2-dioxaborolan-2-yl) phenoxy)ethyl) carbamate (Int-B)

To a stirred solution of 4-hydroxyphenylboronic acid pinacol ester (789 mg, 3.58 mmol) in DMF (13 ml) were added B7 (900 mg, 4.66 mmol), KI (18 mg, 0.10 mmol) and $Cs_2CO_3$ (2.57 g, 7.88 mmol) under argon atmosphere. The reaction mixture was heated to 65° C. and stirred for 16 h. The reaction mixture was poured into water (20 ml) and extracted with EtOAc (3×20 ml). The combined organic layer was concentrated under reduced pressure to obtain the crude which was purified by column chromatography using 7% EtOAc/Hexane to afford Int-B as a pale yellow solid (580 mg, 1.53 mmol, 43%).

$^1$H NMR (400 MHz, $CDCl_3$): δ 7.74 (d, J=8.4 Hz, 2H), 6.87 (d, J=8.8 Hz, 2H), 4.16-4.06 (m, 2H), 3.65-3.59 (m, 2H), 2.97 (s, 3H), 1.45 (s, 9H), 1.33 (s, 12H) 6.2.3. 2-(2-bromopyridin-4-yl)-1-(pyridin-2-yl)ethan-1-one (B2)

To a stirred solution of 2-Bromo-4-methyl pyridine (B1) (2 g, 11.62 mmol) in THF (30 ml) at −78° C. under argon, a solution of NaHMDS (2 M in THF, 12.7 ml, 25.58 mmol) was added dropwise. The yellow solution was stirred at −78° C. for 30 min. Then a solution of ethyl picolinate (1.72 ml, 12.79 mmol) in THF (10 ml) was added and the reaction mixture warmed to approximately 21° C. and stirred for 16 h. The solvent was evaporated under reduced pressure and the solid residue was triturated with diethyl ether, filtered and washed with diethyl ether. The solid was then diluted with saturated $NH_4Cl$ solution (30 ml) and the aqueous phase was extracted with EtOAc (2×200 ml). The organic layer dried over $Na_2SO_4$ and concentrated. The crude product was purified by silica gel column chromatography using 10% EtOAc/Hexane to afford compound B2 as a yellow solid (2.06 g, 7.46 mmol, 64.3%).

$^1$H NMR (400 MHz, $CDCl_3$): δ 8.75 (d, J=5.2 Hz, 1H), 8.32 (d, J=5.2 Hz, 1H), 8.08 (d, J=8.0 Hz, 1H), 7.89 (t, J=7.6 Hz 1H), 7.56-7.51 (m, 2H), 7.28-7.25 (m, 1H), 4.55 (s, 2H)

LC-MS (ESI): m/z 277 $[M]^+$

6.2.4. 2-bromo-4-[3-(pyridin-2-yl)-1H-pyrazol-4-yl] pyridine (B3)

A solution of B2 (850 mg, 3.07 mmol) in dry DMF (3.4 ml) under argon was treated with glacial acetic acid (0.45 ml, 7.39 mmol) in DMF. DMA (0.6 ml, 4.61 mmol) was added drop wise and the mixture was stirred at approximately 21° C. under argon atmosphere for 2 h. Hydrazine monohydrate (1.15 ml, 23.09 mmol) was added drop wise and the resulting mixture heated at 50° C. for 3 h and at approximately 21° C. for 16 h. The reaction mixture was poured into water (30 ml) and extracted with $CH_2Cl_2$ (3×30 ml). The organic layer was dried over $Na_2SO_4$ and filtered. The solvent was evaporated under reduced pressure to afford the crude compound. The crude product was purified by silica gel column chromatography using 30% EtOAc/Hexane to afford compound B3 as a yellow solid (560 mg, 1.86 mmol, 60.6%).

$^1$H NMR (500 MHz, $CDCl_3$): δ 8.74 (brs, 1H), 8.34 (d, J=5.0 Hz, 1H), 7.83 (brs, 1H), 7.81 (t, J=6.0 Hz, 1H), 7.56 (s, 1H), 7.49 (d, J=8.0 Hz, 1H), 7.39-7.84 (m, 1H), 7.31-7.26 (m, 1H)

LC-MS (ESI): m/z 301 $[M]^+$

6.2.5. 2-Bromo-4-(3-(pyridin-2-yl)-1-trityl-1H-pyrazol-4-yl) pyridine (B4)

To a stirred solution of B3 (500 mg, 1.66 mmol) in acetone (10 ml) was added $K_2CO_3$ (1.37 g, 9.99 mmol) and trityl chloride (464 mg, 2.49 mmol). The reaction mixture was subsequently heated to reflux and stirred for 24 h. The reaction mixture was filtered and the filtrate concentrated, and then partitioned between $CH_2Cl_2$ (20 ml) and water (10 ml). The organic phase was dried over $Na_2SO_4$ and concentrated. The crude solid was purified by silica gel column chromatography using 2% MeOH/$CH_2Cl_2$ to afford compound B4 as a pale yellow solid (402 mg, 0.74 mmol, 44%).

$^1$H NMR (500 MHz, $CDCl_3$): δ 8.53 (d, J=4.5 Hz, 1H), 8.20 (d, J=5.5 Hz, 1H), 7.75-7.05 (m, 2H), 7.56 (s, 1H), 7.51 (s, 1H), 7.35-7.32 (m, 9H), 7.25-7.22 (m, 8H)

6.2.6. Tert-butylmethyl (2-(4-(4-(3-(pyridin-2-yl)-1-trityl-1H-pyrazol-4-yl) pyridin-2-yl) phenoxy) ethyl) carbamate (B5))

To a stirred solution of B4 (100 mg, 0.18 mmol) in toluene (2 ml) was added Int-B (185 mg, 0.49 mmol) in EtOH (0.75 ml) followed by 2M $Na_2CO_3$ solution (0.45 ml) under argon atmosphere. The reaction mixture was degassed with argon for 20 min and then $Pd(PPh_3)_4$ (16 mg, 0.01 mmol) was added and refluxed for 3 h. After complete consumption of starting material (monitored by TLC), the reaction mixture was poured into water and extracted with toluene (3×15 ml). The organic layer was dried over $Na_2SO_4$ and concentrated under reduced pressured to afford the crude product which was purified by silica gel column chromatography using 30% EtOAc/hexane to afford compound B5 as a colorless solid (70 mg, 0.09 mmol, 53%).

$^1$H NMR (400 MHz, $CDCl_3$): δ 8.53 (s, 1H), 8.49 (d, J=4.8 Hz, 1H), 7.82 (d, J=8.8 Hz, 2H) 7.74-7.76 (m, 3H), 7.60 (s, 1H), 7.40-7.34 (s, 8H), 7.31-7.30 (m, 2H), 7.24-7.19 (m, 4H), 7.12-7.10 (m, 1H), 6.93 (d, J=8.8 Hz, 2H), 4.19-4.12 (m, 2H), 3.66-3.58 (m, 2H), 2.98 (s, 3H), 1.46 (s, 9H)

6.2.7. N-methyl-2-(4-(4-(3-(pyridin-2-yl)-1H-pyrazol-4-yl) pyridin-2-yl) phenoxy) ethan-1-amine hydrochloride (Compound B)

To a stirred solution B5 (70 mg, 0.09 mmol) in $CH_2Cl_2$ (6 ml) was added 4 N HCl in 1,4-dioxane (0.5 ml) at 0° C. The reaction mixture was stirred for 1 h under argon atmosphere. After complete consumption of starting material (monitored by TLC), the solvent was evaporated under reduced pressure to obtain the crude compound was triturated with n-pentane (2×1 ml) and dried to afford Compound B HCl salt as a colorless solid (25 mg, 0.06 mmol, 69%).

$^1$H NMR (400 MHz, DMSO-d$_6$): δ 8.94 (brs, 2H), 8.62-8.56 (m, 3H), 8.30 (brs, 1H), 8.03-7.96 (m, 3H), 7.86 (d, J=7.6 Hz, 1H), 7.69 (brs, 1H), 7.49 (dd, J=7.2, 5.6 Hz, 1H), 7.29 (d, J=7.6 Hz, 1H), 7.20 (d, J=8.4 Hz, 1H), 4.36 (t, J=4.8 Hz, 2H), 3.39-3.35 (m, 2H), 2.67-2.63 (m, 3H)

LC-MS (ESI): m/z 372 [M+H]$^+$

6.3. Example 3: Synthesis of N-methyl-2-(4-{4-[3-(6-methylpyridin-2-yl)-1H-pyrazol-4-yl]pyridin-2-yl}phenoxy)ethan-1-amine (Compound C)

Compound C was prepared according to the general methodology in Scheme 3 below:

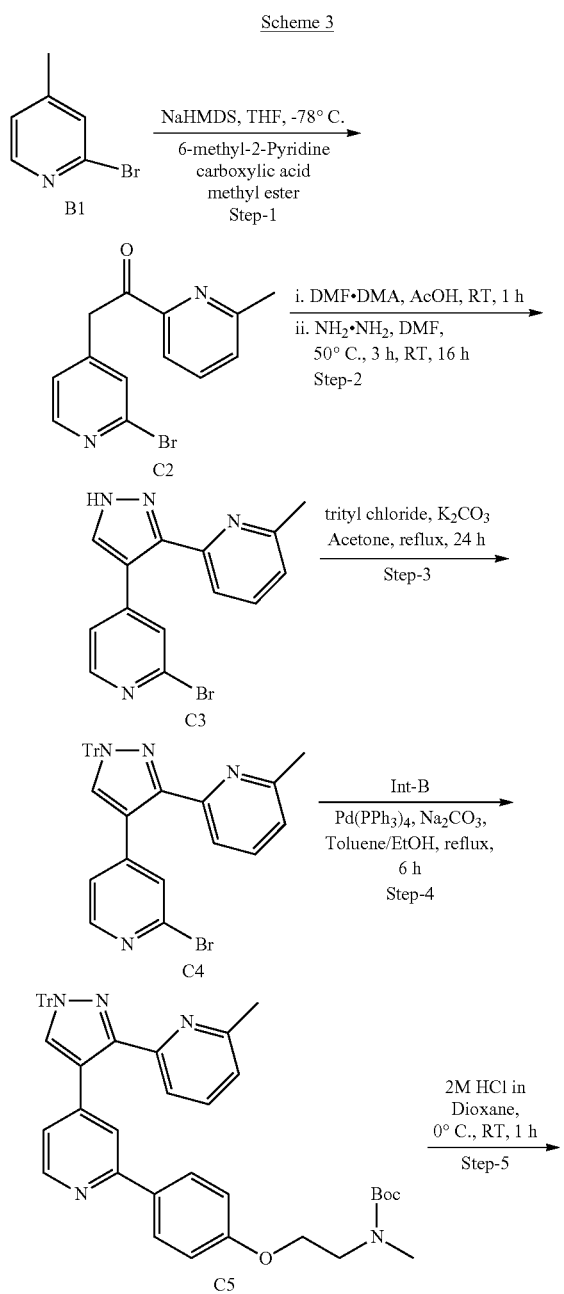

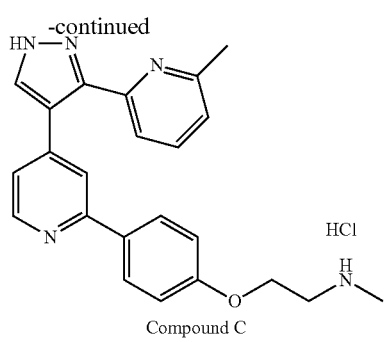

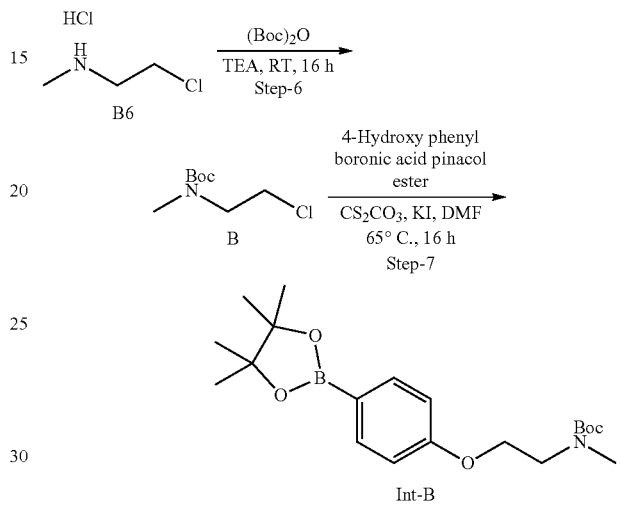

6.3.1. 2-(2-bromopyridin-4-yl)-1-(6-methylpyridin-2-yl)ethan-1-one (C2)

To a stirred solution of 2-Bromo-4-methyl pyridine (B1) (1 g, 5.81 mmol) in THF (15 ml) at −78° C. under argon, a solution of NaHMDS (2 M in THF, 6.39 ml, 12.8 mmol) was added dropwise. The yellow solution was stirred at −78° C. for 30 min. Then a solution of 6-methyl Picolinic acid methyl ester (1.19 ml, 8.72 mmol) in THF (7 ml) was added and the reaction mixture was allowed to warm up to approximately 21° C. and stirred for 16 h. The solvent was evaporated under reduced pressure and the solid residue was triturated with diethyl ether, filtered and washed with diethyl ether. The solid was then diluted with saturated NH$_4$Cl solution (20 ml) and the aqueous phase was extracted with EtOAc (2×150 ml). The organic layer was dried over Na$_2$SO$_4$ and concentrated. The crude product was purified by silica gel column chromatography using 10% EtOAc/Hexane to afford compound C2 as a yellow solid (1.1 g, 3.79 mmol, 65.4%).

$^1$H NMR (500 MHz, CDCl$_3$): δ 8.30 (d, J=5.0 Hz, 1H), 7.86 (d, J=8 Hz, 1H), 7.73 (t, J=7.5 Hz, 1H), 7.51 (s, 1H), 7.36 (d, J=8 Hz, 1H), 7.24 (d, J=5 Hz, 1H), 4.52 (s, 2H), 2.64 (s, 3H)

LC-MS (ESI): m/z 291 [M]$^+$

6.3.2. 2-bromo-4-[3-(6-methylpyridin-2-yl)-1H-pyrazol-4-yl]pyridine (C3)

A solution of C2 (300 mg, 1.03 mmol) in dry DMF (1 ml) under argon was treated with glacial acetic acid (0.14 ml, 2.48 mmol) in DMF. DMA (0.2 ml, 1.55 mmol) was added drop wise and the mixture was stirred at approximately 21°

C. under argon atmosphere for 1 h. Hydrazine monohydrate (0.37 ml, 7.75 mmol) was added drop wise and the resulting mixture heated at 50° C. for 3 h and at approximately 21° C. for 16 h. The reaction mixture was poured into water (20 ml) and extracted with CH$_2$Cl$_2$ (3×20 ml). The organic layer was dried over Na$_2$SO$_4$ and filtered. The solvent was evaporated under reduced pressure to afford crude C3. The crude C3 was purified by silica gel column chromatography using 2% MeOH/DCM to afford purified C3 as a yellow solid (172 mg, 0.54 mmol, 53%).

$^1$H NMR (500 MHz, CDCl$_3$): δ 11.40 (brs, 1H), 8.37 (d, J=5.0 Hz, 1H), 7.74 (s, 1H), 7.64 (s, 1H), 7.58 (t, J=8.0 Hz, 1H), 7.34 (d, J=6.0 Hz, 1H), 7.26 (d, J=8.0 Hz, 1H), 7.17 (d, J=8.0 Hz, 1H), 2.60 (s, 3H)

LC-MS (ESI): m/z 315 [M+H]$^+$

6.3.3. 2-Bromo-4-(3-(6-methylpyridin-2-yl)-1-trityl-1H-pyrazol-4-yl) pyridine (C4)

To a stirred solution of C3 (40 mg, 0.12 mmol) in acetone (2 ml) was added K$_2$CO$_3$ (53 mg, 0.38 mmol) and trityl chloride (53 mg, 0.19 mmol). The reaction mixture was subsequently heated to reflux and stirred for 24 h. The reaction mixture was filtered and the filtrate concentrated, and then partitioned between CH$_2$Cl$_2$ (5 ml) and water (5 ml). The organic phase was dried over Na$_2$SO$_4$ and concentrated. The crude solid was purified by silica gel column chromatography using 2% MeOH/CH$_2$Cl$_2$ to afford compound C4 as a pale yellow solid (30 mg, 0.05 mmol, 41%).

$^1$H NMR (400 MHz, CDCl$_3$): δ 8.22 (d, J=4.8 Hz, 1H), 7.73 (s, 1H), 7.59 (s, 3H), 7.39-7.35 (m, 9H), 7.31 (s, 1H), 7.28-7.25 (m, 6H), 7.24 (d, J=12 Hz, 1H), 2.53 (s, 3H)

LC-MS (ESI): m/z 558 [M+H]$^+$

6.3.4. Tert-butylmethyl (2-(4-(4-(3-(6-methylpyridin-2-yl)-1-trityl-1H-pyrazol-4-yl) pyridin-2-yl) phenoxy) ethyl) carbamate (C5)

To the stirred solution of C4 (150 mg, 0.26 mmol) in toluene (5 ml) was added Int-B (152 mg, 0.40 mmol) in EtOH (1 ml) followed by 2M Na$_2$CO$_3$ solution (0.7 ml) under argon atmosphere. The reaction mixture was degassed with argon for 20 min and then Pd(PPh$_3$)$_4$ (25 mg, 0.02 mmol) was added and refluxed for 6 h. After complete consumption of starting material (monitored by TLC), the reaction mixture was poured into water and extracted with toluene (3×10 ml). The organic layer was dried over Na$_2$SO$_4$ and concentrated under reduced pressure to afford crude C5, which was purified by silica gel column chromatography using 30% EtOAc/hexane to afford purified C5 as a brown solid (51 mg, 0.07 mmol, 26%).

$^1$H NMR (400 MHz, CDCl$_3$): δ 8.48 (d, J=5.2 Hz, 1H), 7.82 (d, J=8.8 Hz, 3H), 7.74 (s, 1H), 7.60 (s, 1H), 7.56 (d, J=15.2 Hz, J=7.6 Hz, 2H), 7.35-7.33 (m, 8H), 7.28-7.27 (m, 6H), 7.08 (d, J=6.8 Hz, 2H), 6.93 (d, J=8.8 Hz, 2H), 4.16-4.08 (m, 2H), 3.63-3.58 (m, 2H), 2.98 (s, 3H), 2.41 (s, 3H), 1.46 (s, 9H)

6.3.5. N-methyl-2-(4-{4-[3-(6-methylpyridin-2-yl)-1H-pyrazol-4-yl]pyridin-2-yl}phenoxy)ethan-1-amine (Compound C)

To a stirred solution of C5 (51 mg, 0.07 mmol) in CH$_2$Cl$_2$ (5 ml) was added 4 N HCl in 1,4-dioxane (0.3 ml) at 0° C. The reaction mixture was then stirred for 1 h under argon atmosphere. After complete consumption of starting material (monitored by TLC), the solvent was evaporated under reduced pressure to obtain crude Compound C. The crude Compound C was then triturated with n-pentane (2×1 ml) and dried to afford Compound C as an HCl salt as a brown solid (20 mg, 0.05 mmol, 74%).

$^1$H NMR (400 MHz, DMSO-d$_6$): δ 8.93 (brs, 2H), 8.61 (d, J=5.6 Hz, 1H), 8.56 (brs, 1H), 8.33 (brs, 1H), 8.03 (d, J=8.8 Hz, 2H), 7.88 (t, J=7.6 Hz, 1H), 7.78-7.74 (m, 1H), 7.65 (d, J=7.2 Hz, 1H), 7.38 (d, J=7.6 Hz, 1H), 7.20 (d, J=8.4 Hz, 2H), 4.36 (t, J=5.2 Hz, 2H), 3.36 (t, J=5.2 Hz, 2H), 2.66-2.63 (m, 3H), 2.50-2.46 (m, 3H)

LC-MS (ESI): m/z 386 [M+H]$^+$

6.4. Example 4: Synthesis of (Z)—N-ethyl-3-(((4-(N-(2-(methylamino)ethyl)methylsulfonamido)phenyl)amino)(phenyl)methylene)-2-oxoindoline-6-carboxamide (Compound D)

Compound D was prepared according to the general methodology in Scheme 4 below:

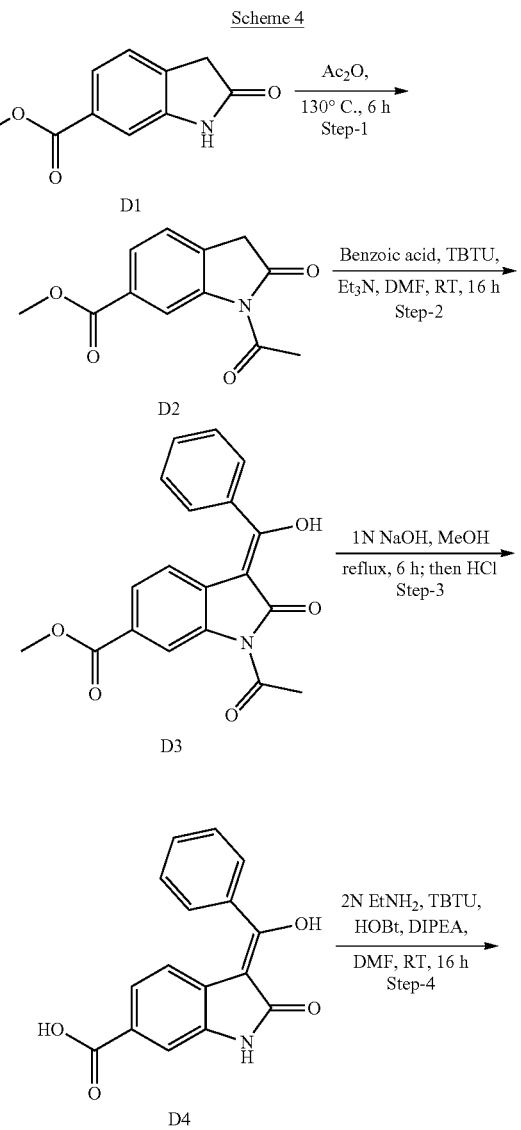

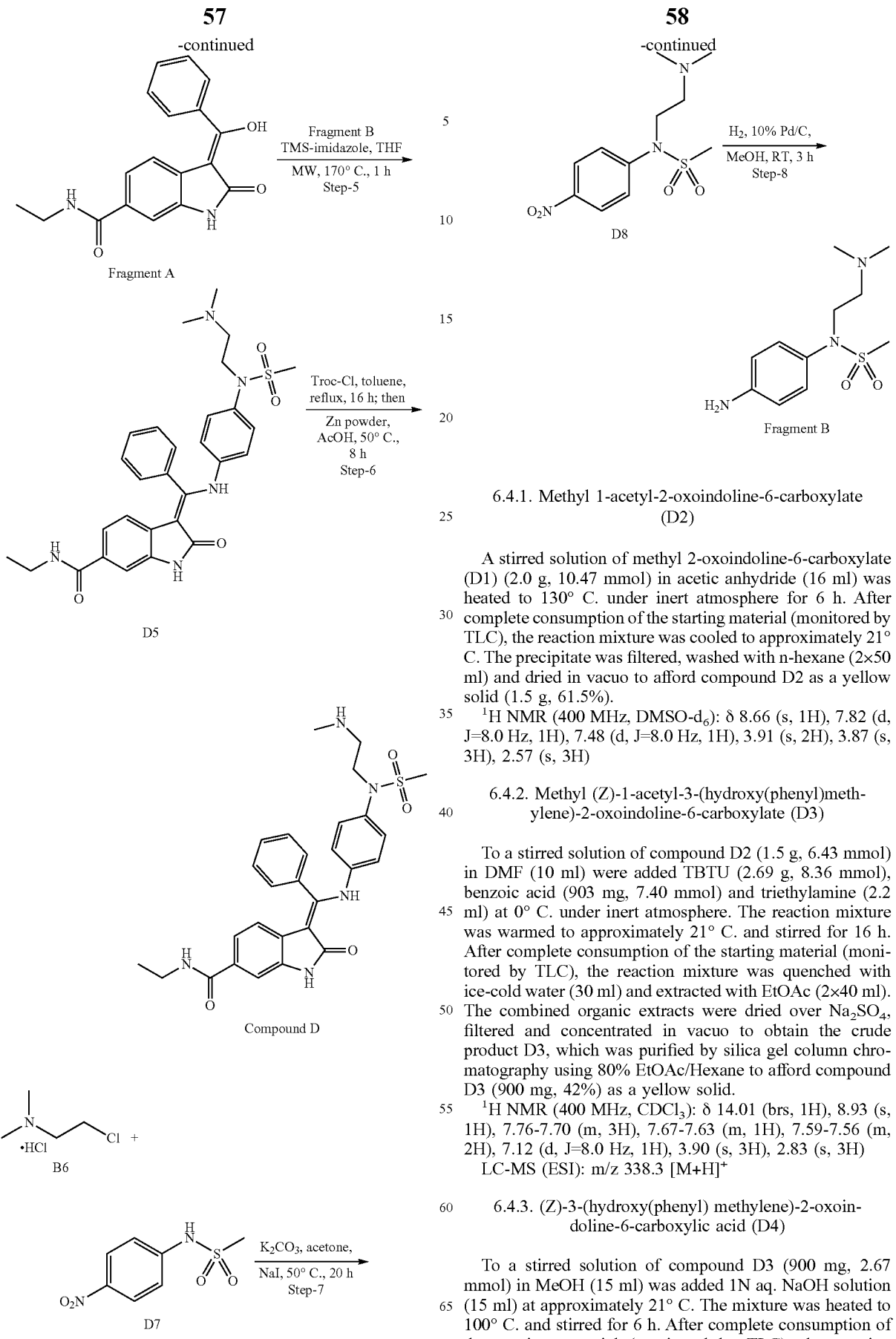

6.4.1. Methyl 1-acetyl-2-oxoindoline-6-carboxylate (D2)

A stirred solution of methyl 2-oxoindoline-6-carboxylate (D1) (2.0 g, 10.47 mmol) in acetic anhydride (16 ml) was heated to 130° C. under inert atmosphere for 6 h. After complete consumption of the starting material (monitored by TLC), the reaction mixture was cooled to approximately 21° C. The precipitate was filtered, washed with n-hexane (2×50 ml) and dried in vacuo to afford compound D2 as a yellow solid (1.5 g, 61.5%).

$^1$H NMR (400 MHz, DMSO-$d_6$): δ 8.66 (s, 1H), 7.82 (d, J=8.0 Hz, 1H), 7.48 (d, J=8.0 Hz, 1H), 3.91 (s, 2H), 3.87 (s, 3H), 2.57 (s, 3H)

6.4.2. Methyl (Z)-1-acetyl-3-(hydroxy(phenyl)methylene)-2-oxoindoline-6-carboxylate (D3)

To a stirred solution of compound D2 (1.5 g, 6.43 mmol) in DMF (10 ml) were added TBTU (2.69 g, 8.36 mmol), benzoic acid (903 mg, 7.40 mmol) and triethylamine (2.2 ml) at 0° C. under inert atmosphere. The reaction mixture was warmed to approximately 21° C. and stirred for 16 h. After complete consumption of the starting material (monitored by TLC), the reaction mixture was quenched with ice-cold water (30 ml) and extracted with EtOAc (2×40 ml). The combined organic extracts were dried over $Na_2SO_4$, filtered and concentrated in vacuo to obtain the crude product D3, which was purified by silica gel column chromatography using 80% EtOAc/Hexane to afford compound D3 (900 mg, 42%) as a yellow solid.

$^1$H NMR (400 MHz, $CDCl_3$): δ 14.01 (brs, 1H), 8.93 (s, 1H), 7.76-7.70 (m, 3H), 7.67-7.63 (m, 1H), 7.59-7.56 (m, 2H), 7.12 (d, J=8.0 Hz, 1H), 3.90 (s, 3H), 2.83 (s, 3H)

LC-MS (ESI): m/z 338.3 [M+H]$^+$

6.4.3. (Z)-3-(hydroxy(phenyl) methylene)-2-oxoindoline-6-carboxylic acid (D4)

To a stirred solution of compound D3 (900 mg, 2.67 mmol) in MeOH (15 ml) was added 1N aq. NaOH solution (15 ml) at approximately 21° C. The mixture was heated to 100° C. and stirred for 6 h. After complete consumption of the starting material (monitored by TLC), the reaction mixture was cooled to approximately 21° C., quenched with 1N aq. HCl solution (13 ml) and stirred for 30 min. The precipitated solid was filtered, washed with 20% EtOAc/Hexane to obtain compound D4 (580 mg, 77%) as an off-white solid, which was carried to the next step without further purification.

$^1$H NMR (400 MHz, DMSO-$d_6$): δ 12.76 (brs, 1H), 11.61 (brs, 1H), 7.77-7.50 (m, 8H), 7.13 (brs, 1H) 6.4.4. (Z)—N-ethyl-3-(hydroxy(phenyl)methylene)-2-oxoindoline-6-carboxamidelate (Fragment A)

To a stirred solution of compound D4 (580 mg, 2.06 mmol) in DMF (10 ml) were added TBTU (729 mg, 2.27 mmol), HOBt (306 mg, 2.27 mmol) and N,N-diisopropyl ethylamine (1.9 ml, 10.32 mmol) at approximately 21° C. under inert atmosphere. After 30 min, 2N ethylamine in THF (2.1 ml, 4.12 mmol) was added at 0° C. and stirred for 1 h. The reaction mixture was then warmed to approximately 21° C. and stirred for additional 16 h. After complete consumption of the starting material (monitored by TLC), the volatiles were removed in vacuo. The residue was diluted with water (15 ml), filtered and washed with 20% EtOAc/Hexane (2×10 ml) to obtain the crude product, which was purified by silica gel column chromatography using 10% MeOH/$CH_2Cl_2$ to afford Fragment A (410 mg, 64.5%) as an off-white solid.

$^1$H NMR (400 MHz, DMSO-$d_6$): δ 13.62 (brs, 1H), 11.39 (brs, 1H), 8.35-8.33 (m, 1H), 7.76-7.52 (m, 5H), 7.44-7.36 (m, 3H), 3.29-3.22 (m, 2H), 1.10 (t, J=7.2 Hz, 3H)

LC-MS (ESI): m/z 307.1 (M–H$^+$) 6.4.5. N-(2-(dimethylamino)ethyl)-N-(4-nitrophenyl)methanesulfonamide (D8)

To a stirred solution of compound D7 (800 mg, 3.70 mmol) in acetone (15 ml) were added potassium carbonate (1.32 g, 9.62 mmol), sodium iodide (110 mg, 0.74 mmol) and compound B6 (799 mg, 5.55 mmol) at 0° C. under inert atmosphere. The reaction mixture was heated to 50° C. and stirred for 20 h. After complete consumption of the starting material (monitored by TLC), the volatiles were removed in vacuo. The residue was diluted with water (20 ml) and extracted with EtOAc (2×40 ml). The combined organic extracts were dried over $Na_2SO_4$, filtered and concentrated in vacuo to obtain the crude product, which was purified by silica gel column chromatography using 5% MeOH/$CH_2Cl_2$ to afford compound D8 (460 mg, 43%) as a pale yellow solid.

$^1$H NMR (500 MHz, DMSO-$d_6$): δ 8.27 (d, J=9.5 Hz, 2H), 7.68 (d, J=9.5 Hz, 2H), 3.85 (t, J=6.5 Hz, 2H), 3.13 (s, 3H), 2.31 (t, J=6.5 Hz, 2H), 2.12 (s, 6H)

LC-MS (ESI): m/z 288.3 [M+H]$^+$ 6.4.6. N-(4-aminophenyl)-N-(2-(dimethylamino)ethyl)methanesulfonamide (Fragment B)

To a stirred solution of compound D8 (460 mg, 1.60 mmol) in MeOH (10 ml) was added 10% Pd/C (40 mg) and stirred at approximately 21° C. under hydrogen atmosphere (balloon pressure) for 3 h. After complete consumption of the starting material (monitored by TLC), the reaction mixture was filtered through a pad of Celite® and washed with MeOH (10 ml). The filtrate was concentrated in vacuo to obtain the crude product, which was purified by silica gel column chromatography using 10% MeOH/$CH_2Cl_2$ to afford Fragment B (300 mg 73%) as a pale yellow solid.

$^1$H NMR (400 MHz, DMSO-$d_6$): δ 6.99 (d, J=8.8 Hz, 2H), 6.54 (d, J=8.8 Hz, 2H), 5.25 (s, 2H), 3.55 (t, J=7.2 Hz, 2H), 2.91 (s, 3H), 2.24 (t, J=7.2 Hz, 2H), 2.12 (s, 6H)

LC-MS (ESI): m/z 258.2 [M+H]$^+$ 6.4.7. (Z)-3-(((4-(N-(2-(dimethylamino)ethyl)methylsulfonamido)phenyl)amino)(phenyl) methylene)-N-ethyl-2-oxoindoline-6-carboxamide (D5)

A solution of Fragment A (200 mg, 0.64 mmol), Fragment B (500 mg, 1.94 mmol) and TMS-imidazole (455 mg, 3.24 mmol) in THF (5 ml) was heated to 170° C. under microwave for 1 h. After consumption of the starting material (monitored by TLC and LC-MS), the volatiles were removed in vacuo. The residue was diluted with water (10 ml) and extracted with EtOAc (3×25 ml) to obtain the crude product, which was purified by preparative HPLC to afford compound D5 (150 mg, 42%) as a pale yellow solid.

$^1$H NMR (400 MHz, DMSO-$d_6$): δ 12.14 (s, 1H), 10.91 (s, 1H), 8.17 (t, J=5.6 Hz, 1H), 7.64-7.57 (m, 3H), 7.53-7.51 (m, 2H), 7.34 (s, 1H), 7.17 (d, J=8.8 Hz, 2H), 7.06 (d, J=8.4 Hz, 1H), 6.84 (d, J=8.8 Hz, 2H), 5.73 (d, J=8.4 Hz, 1H), 3.58 (t, J=6.8 Hz, 2H), 3.23-3.20 (m, 2H), 2.93 (s, 3H), 2.13 (t, J=6.8 Hz, 2H), 1.90 (s, 6H), 1.06 (t, J=7.2 Hz, 3H)

LC-MS (ESI): m/z 548.6 [M+H]$^+$ 6.4.8. (Z)—N-ethyl-3-(((4-(N-(2-(methylamino)ethyl)methylsulfonamido)phenyl)amino)(phenyl) methylene)-2-oxoindoline-6-carboxamide (Compound D)

To a stirred solution of compound D5 (70 mg, 0.12 mmol) in dry toluene (3 ml) was added 2,2,2-trichlorethoxycarbonyl chloride (0.04 ml, 0.19 mmol) at approximately 21° C. under inert atmosphere. The reaction mixture was heated to reflux temperature (120° C.) and maintained for 16 h. After consumption of the starting material (monitored by TLC), the reaction mixture was cooled to approximately 21° C., diluted with EtOAc (30 ml) and washed with 1N aq. HCl solution (15 ml). The organic layer was dried over $Na_2SO_4$, filtered and concentrated in vacuo to obtain the mono de-methylated with di-troc-protected compound (40 mg).

The crude product from the above reaction was dissolved in acetic acid (3 ml) and zinc powder (9 mg, 0.13 mmol) was added at approximately 21° C. under inert atmosphere. The reaction mixture was heated to 50° C. and stirred for 8 h. After complete consumption of the starting material (monitored by TLC), the reaction mixture was cooled to approximately 21° C. and the volatiles were removed in vacuo. The residue was diluted with water (20 ml) and extracted with EtOAc (2×25 ml). The combined organic extracts were washed with saturated $NaHCO_3$ solution (20 ml), dried over $Na_2SO_4$, filtered and concentrated under reduced pressure to obtain the crude Compound D, which was purified by silica gel column chromatography using 5-6% MeOH/$CH_2Cl_2$ to afford 12 mg of Compound D with 83% HPLC purity.

The reaction was repeated on a 60 mg scale and the obtained crude product was combined with above batch and purified by preparative HPLC to afford Compound D (8.0 mg, 6.3%) as a pale yellow solid.

$^1$H NMR (400 MHz, CD$_3$OD): δ 7.65-7.59 (m, 3H), 7.52.7.50 (m, 2H), 7.40 (s, 1H), 7.31 (d, J=8.8 Hz, 2H), 7.07 (d, J=8.4 Hz, 1H), 6.90 (d, J=8.8 Hz, 2H), 5.95 (d, J=8.4 Hz, 1H), 3.95 (t, J=5.6 Hz, 2H), 3.39-3.32 (m, 2H), 3.05 (t, J=5.6 Hz, 2H), 2.93 (s, 3H), 2.71 (s, 3H), 1.19 (t, J=7.2 Hz, 3H)

LC-MS (ESI): m/z 534.6 [M+H]$^+$

UPLC purity: 99.18%

6.5. Example 5: Alternative Synthesis of (Z)—N-ethyl-3-(((4-(N-(2-(methylamino)ethyl)methylsulfonamido)phenyl)amino)(phenyl)methylene)-2-oxoindoline-6-carboxamide (Compound D)

Compound D was also prepared according to the general methodology in Scheme 5 below:

Scheme 5

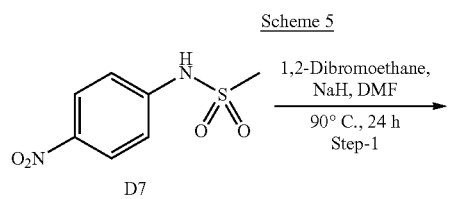
D7
1,2-Dibromoethane, NaH, DMF
90° C., 24 h
Step-1

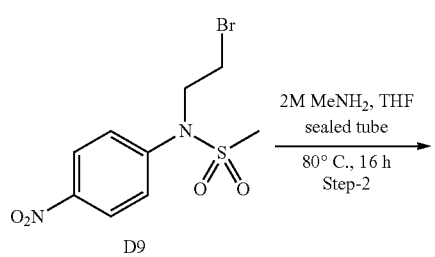
D9
2M MeNH₂, THF sealed tube
80° C., 16 h
Step-2

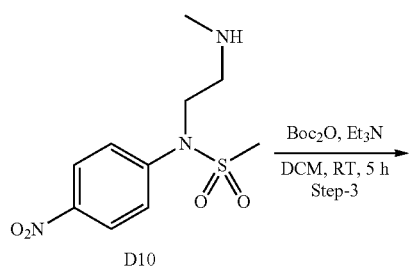
D10
Boc₂O, Et₃N
DCM, RT, 5 h
Step-3

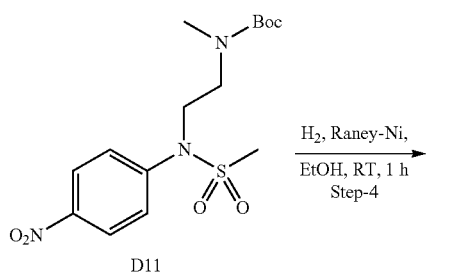
D11
H₂, Raney-Ni,
EtOH, RT, 1 h
Step-4

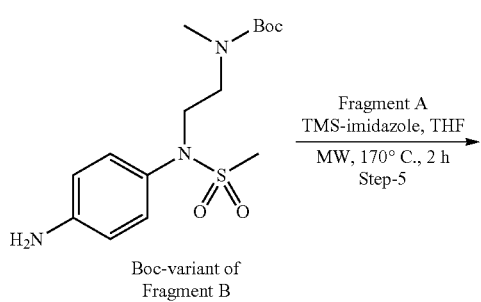
Boc-variant of Fragment B
Fragment A
TMS-imidazole, THF
MW, 170° C., 2 h
Step-5

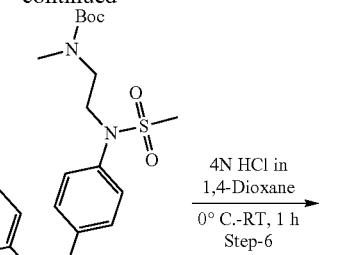
D12
4N HCl in 1,4-Dioxane
0° C.-RT, 1 h
Step-6

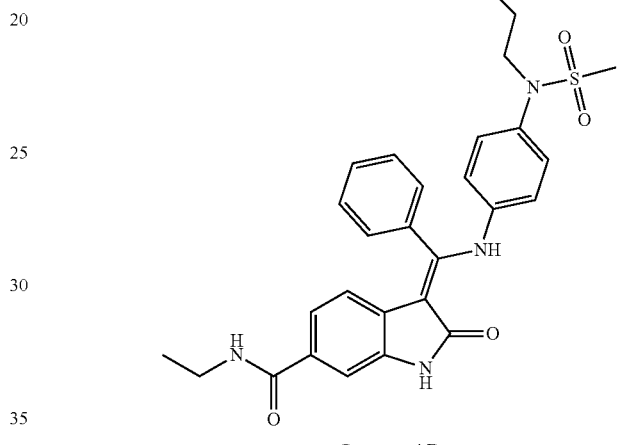
Compound D

6.5.1. N-(2-bromoethyl)-N-(4-nitrophenyl)methanesulfonamide (D9)

To a stirred solution of compound D7 (1.0 g, 4.65 mmol) in DMF (10 ml) was added sodium hydride (60% in mineral oil; 320 mg, 7.99 mmol) at 0° C. under inert atmosphere and stirred at approximately 21° C. for 30 min. To this mixture, 1,2-dibromoethane (2.18 g, 11.60 mmol) was added at approximately 21° C. The mixture was heated to 90° C. and stirred for 24 h. The reaction was monitored by TLC. The reaction mixture was cooled to approximately 21° C., quenched with ice-cold water (30 ml) and extracted with EtOAc (2×40 ml). The combined organic extracts were dried with Na₂SO₄, filtered and concentrated in vacuo to obtain the crude product, which was purified by silica gel column chromatography using 5% MeOH/CH₂Cl₂ to afford 1.2 g of D9 as a mixture containing 40% unreacted starting material. The obtained mixture was directly taken for next reaction without further purification.

$^1$H NMR (500 MHz, CDCl₃): δ 8.29 (d, J=8.5 Hz, 2H), 7.56 (d, J=8.5 Hz, 2H), 4.12 (t, J=7.0 Hz, 2H), 3.44 (t, J=7.0 Hz, 2H), 3.01 (s, 3H)

6.5.2. N-(2-(methylamino)ethyl)-N-(4-nitrophenyl)methanesulfonamide (D10)

To a stirred solution of compound D9 (1.2 g, impure) in THF (10 ml) were added triethylamine (1.6 ml) and methylamine (2M in THF; 9.3 ml, 18.63 mmol) in a sealed tube at approximately 21° C. under inert atmosphere. The reaction mixture was heated to 80° C. and maintained for 16 h. After complete consumption of the starting material (monitored by TLC), the reaction mixture was cooled to approximately 21° C. and concentrated under reduced pressure to obtain crude D10. The crude D10 was purified by silica gel column chromatography using 15% MeOH/CH$_2$Cl$_2$ to afford compound D10 as a yellow solid (500 mg, 39% overall yield in two steps).

$^1$H NMR (500 MHz, DMSO-d$_6$): δ 8.94 (brs, 1H), 8.31 (d, J=9.0 Hz, 2H), 7.80 (d, J=8.5 Hz, 2H), 4.06 (t, J=6.0 Hz, 2H), 3.15 (s, 3H), 3.00 (t, J=6.0 Hz, 2H), 2.55 (s, 3H)

6.5.3. tert-butyl methyl(2-(N-(4-nitrophenyl)methylsulfonamido)ethyl)carbamate (011)

To a stirred solution of D10 (500 mg, 1.83 mmol) in CH$_2$Cl$_2$ (10 ml) were added triethylamine (0.4 ml, 2.61 mmol) and Boc-anhydride (659 mg, 3.02 mmol) at approximately 21° C. under inert atmosphere and maintained for 5 h. After complete consumption of the starting material (monitored by TLC), the volatiles were removed in vacuo to obtain the crude product, which was purified by silica gel column chromatography using 5% MeOH/CH$_2$Cl$_2$ to afford 011 as a colorless thick syrup (320 mg, 47%).

$^1$H NMR (400 MHz, DMSO-d$_6$): δ 8.27 (d, J=8.4 Hz, 2H), 7.68 (d, J=8.4 Hz, 2H), 3.91 (t, J=6.4 Hz, 2H), 3.28-3.25 (m, 2H), 3.07 (s, 3H), 2.72-2.70 (m, 3H), 1.33-1.27 (m, 9H)

LC-MS (ESI): m/z 274.2 (M+−B° C.)

6.5.4. tert-butyl (2-(N-(4-aminophenyl)methylsulfonamido)ethyl)(methyl)carbamate (Boc-variant of Fragment B)

To a solution of compound 011 (250 mg, 0.67 mmol) in EtOH (10 ml) was added Raney-Ni (40 mg) and stirred at approximately 21° C. under hydrogen atmosphere (balloon pressure) for 1 h. After complete consumption of the starting material (monitored by TLC), the reaction mixture was filtered through a pad of Celite® and washed with EtOH (10 ml). The combined filtrate was concentrated in vacuo to obtain the crude product, which was purified by silica gel column chromatography using 10% MeOH/CH$_2$Cl$_2$ to afford Boc-variant of Fragment B as a pale yellow solid (180 mg, 77%).

H NMR (400 MHz, DMSO-d$_6$): δ 7.01 (d, J=8.4 Hz, 2H), 6.53 (d, J=8.4 HZ, 2H), 5.24 (s, 2H), 3.60 (t, J=6.4 Hz, 2H), 3.18 (t, J=6.4 HZ, 2H), 2.88 (s, 3H), 2.75-2.71 (m, 3H), 1.36-1.33 (m, 9H)

LC-MS (ESI): m/z 244.2 (M$^+$−B° C.)

6.5.5. tert-butyl (Z)-(2-(N-(4-(((6-(ethylcarbamoyl)-2-oxoindolin-3-ylidene)(phenyl)methyl)amino)phenyl) methylsulfonamido)ethyl)(methyl)carbamate (D10)

A solution of Fragment A (70 mg, 0.22 mmol), Boc-variant of Fragment B (155 mg, 0.45 mmol) and TMS-imidazole (159 mg, 1.13 mmol) in THF (3 ml) was heated to 170° C. under microwave for 160 min. After consumption of the starting material (monitored by TLC and LC-MS), the volatiles were removed in vacuo to obtain the residue, which was purified by preparative HPLC to afford compound D10 (50 mg, 36%) as a pale yellow solid.

$^1$H NMR (400 MHz, CDCl$_3$): δ 12.13 (brs, 1H), 8.01 (brs, 1H), 7.61-7.51 (m, 3H), 7.44-7.41 (m, 3H), 7.13-7.11 (m, 2H), 6.98 (d, J=8.4 HZ, 1H), 6.75 (d, J=8.4 HZ, 2H), 5.96-5.91 (m, 2H), 3.74-3.71 (m, 2H), 3.49-3.41 (m, 2H), 3.30-3.27 (m, 2H), 2.80 (s, 6H), 1.40-1.36 (m, 9H), 1.19 (t, J=7.2 HZ, 3H)

LC-MS (ESI): m/z 634.6 [M+H]$^+$

6.5.6. (Z)—N-ethyl-3-(((4-(N-(2-(methylamino)ethyl)methylsulfonamido)phenyl)amino)(phenyl)methylene)-2-oxoindoline-6-carboxamide hydrochloride (Compound D as HCl salt)

To a stirred solution of compound D10 (20 mg, 0.03 mmol) in diethyl ether (3 ml) was added 4N HCl in 1,4-dioxane (0.3 ml) at 0° C. under inert atmosphere. The reaction mixture was stirred at approximately 21° C. for 1 h. After complete consumption of the starting material (monitored by TLC), the volatiles were removed in vacuo to obtain the crude product, which was triturated with n-pentane (2×4 ml) to afford Compound D as an HCl salt (12 mg, 71%) as a pale yellow solid.

$^1$H NMR (400 MHz, CD$_3$OD): δ 7.65-7.59 (m, 3H), 7.52.7.50 (m, 2H), 7.40 (s, 1H), 7.31 (d, J=8.8 Hz, 2H), 7.07 (d, J=8.4 Hz, 1H), 6.90 (d, J=8.8 Hz, 2H), 5.95 (d, J=8.4 Hz, 1H), 3.95 (t, J=5.6 Hz, 2H), 3.39-3.32 (m, 2H), 3.05 (t, J=5.6 Hz, 2H), 2.93 (s, 3H), 2.71 (s, 3H), 1.19 (t, J=7.2 Hz, 3H).

LC-MS (ESI): m/z 534.7 [M+H]$^+$

UPLC purity: 96.26%

6.6. Example 6: In Vitro Assays to Test Activity of Compounds A-D

6.6.1. N-(2-bromoethyl)-N-(4-nitrophenyl)methanesulfonamide (2)

Compounds A-D were tested to determine whether they could inhibit TGF-β-induced luciferase activity in HEK293T cells in vitro.

30,000 HEK293T cells were seeded in a 96 well white flat bottom plate overnight. The next day 100 ng of a SMAD luciferase reporter plasmid per well was transfected into the cells using lipofectamine for 24 hours. The next day cells were treated with Compounds A-D and 100 pM TGFβ for 24 hours. Luciferase activity was measured using the Dual-Glo® luciferase assay kit (Promega). The assay was run twice for Compounds A, B, and D, and three times for Compound C. The results are shown in Table 4.

TABLE 4

| Compound | Experiment 1 IC$_{50}$ (nM) | Experiment 2 IC$_{50}$ (nM) | Experiment 3 IC$_{50}$ (nM) |
|---|---|---|---|
| Compound A | 18.7 | 29.8 | — |
| Compound B | 51.8 | 11.3 | — |
| Compound C | 10.1 | 21.2 | 13.2 |
| Compound D | 1070 | 1520 | — |

The activity data for Experiment 1 are shown in FIG. 5.

Compounds A-C demonstrated the greatest inhibitory activity.

6.6.2. MTS Proliferation Assay

Compounds A-D were tested to determine whether they could inhibit TGF-β signaling in primary mouse CD4$^+$ T cells.

Primary mouse CD4$^+$ T cells were isolated from the spleens of C57/B6 mice using the RoboSep™ cell isolation system (Stemcell Technologies). 0.5 µg/ml of hamster anti-mouse CD3e antibody (145-2C11; eBioscience) was coated onto a 96 well flat bottom plate overnight. $1\times10^5$ purified CD4$^+$ T cells were incubated with 1 µg/ml soluble hamster anti-mouse CD28 antibody (37.51, BD Biosciences), 1 nM TGF-β1 and 8-fold serial dilutions of Compounds A-D. After 72 hours, cell proliferation was measured using an MTS assay (Promega) in accordance with the manufacturer's instructions. The results are shown in Table 5.

6.7. Example 7: Synthesis of 4-((S)-2-((S)-2-(6-(2, 5-dioxo-2H-pyrrol-1(5H)-yl)hexanamido)-3-methylbutanamido)-5-ureidopentanamido)benzyl methyl (2-(4-(4-(3-(6-methylpyridin-2-yl)-1H-pyrazol-4-yl) pyridin-2-yl)phenoxy)ethyl)carbamate Compound C was linked to a valine-citrulline linker according to the general methodology in Scheme 6 below:

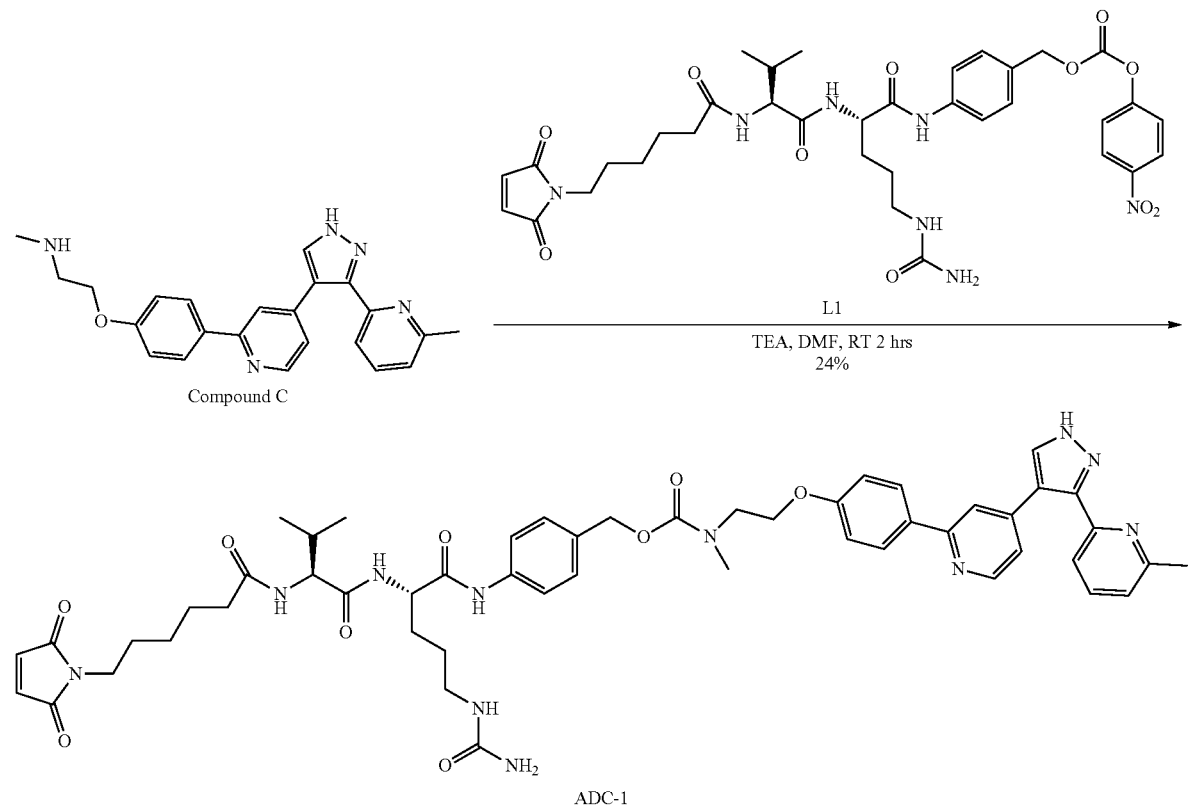

TABLE 5

| Compound | Experiment 1 IC$_{50}$ (nM) | Experiment 2 IC$_{50}$ (nM) |
|---|---|---|
| Compound A | Value not obtained | 153 |
| Compound B | 60 | 34 |
| Compound C | 20 | 33 |
| Compound D | Value not obtained | Value not obtained |

Data for Experiment 1 are shown in FIG. 6.

In two different experiments, an IC$_{50}$ value was not obtained for Compound D. Compound A also did not show consistent effects in mouse CD4$^+$ T cells. Compounds B and C, however, both reversed TGFβ-mediated inhibition of T cell proliferation.

Based on the two assays, Compound C was selected to conjugate into an ADC.

L1 (122 mg, 0.165 mmol, 1.1 equiv.) and TEA (52 µl, 0.375 mmol, 2.5 equiv.) was added to a solution of Compound C (58 mg, 0.150 mmol, 1.0 equiv.) in DMF (2 ml) at 0° C. and the reaction mixture was stirred at approximately 21° C. for 2 hours to afford crude ADC-1. The crude ADC-1 was purified by preparative HPLC to afford purified ADC-1 as a white solid (34 mg, 24% yield).

6.8. Example 8: Generation of Antibody Drug Conjugate 1 (ADC1)

Anti-mouse transferrin receptor antibody R17217 and rat anti-mouse IgG2A isotype control antibody (BioXCell) were dialyzed overnight into conjugation buffer (25 mM Sodium Borate/25 mM NaCl, and 0.3 mM EDTA, final pH 7.4). Antibodies were reduced using tris(2-carboxyethyl) phosphine (TCEP) for 2 hr at reduction ratios of 10-30. ADC-1 was dissolved in DMSO to a final concentration of 10 mM and then conjugated to antibody in the presence of 15% DMSO at conjugation ratios of 5-30. All reactions were carried out at approximately 21° C. For some drug antibody ratios (DAR), 50% propylene glycol was used as the organic solvent during the conjugation step. The final ADC was dialyzed in PBS overnight, filtered using a 0.22 μm filter and analyzed via HPLC-HIC to determine DAR and HPLC-SEC to determine levels of aggregation. For HPLC-HIC, samples were run over a TSKgel® butyl-NPR column with a flow rate of 0.5 ml/min. Phase A was 25 mM sodium phosphate and 1.5 M ammonium sulfate at pH 6.95 while Phase B was 75% 25 mM sodium phosphate at pH 6.95 and 25% isopropyl alcohol. For HPLC-SEC analysis, a TSKgel® G3000SW column (Tosoh Bioscience) was used with a flow rate of 0.25 ml/min for 25 min, at 280 nM.

6.9. Example 9: Synthesis of Compound C Linked to a Disulfide Linker (ADC-2)

Compound C was linked to a disulfide linker according to the general methodology in Scheme 7A-B below:

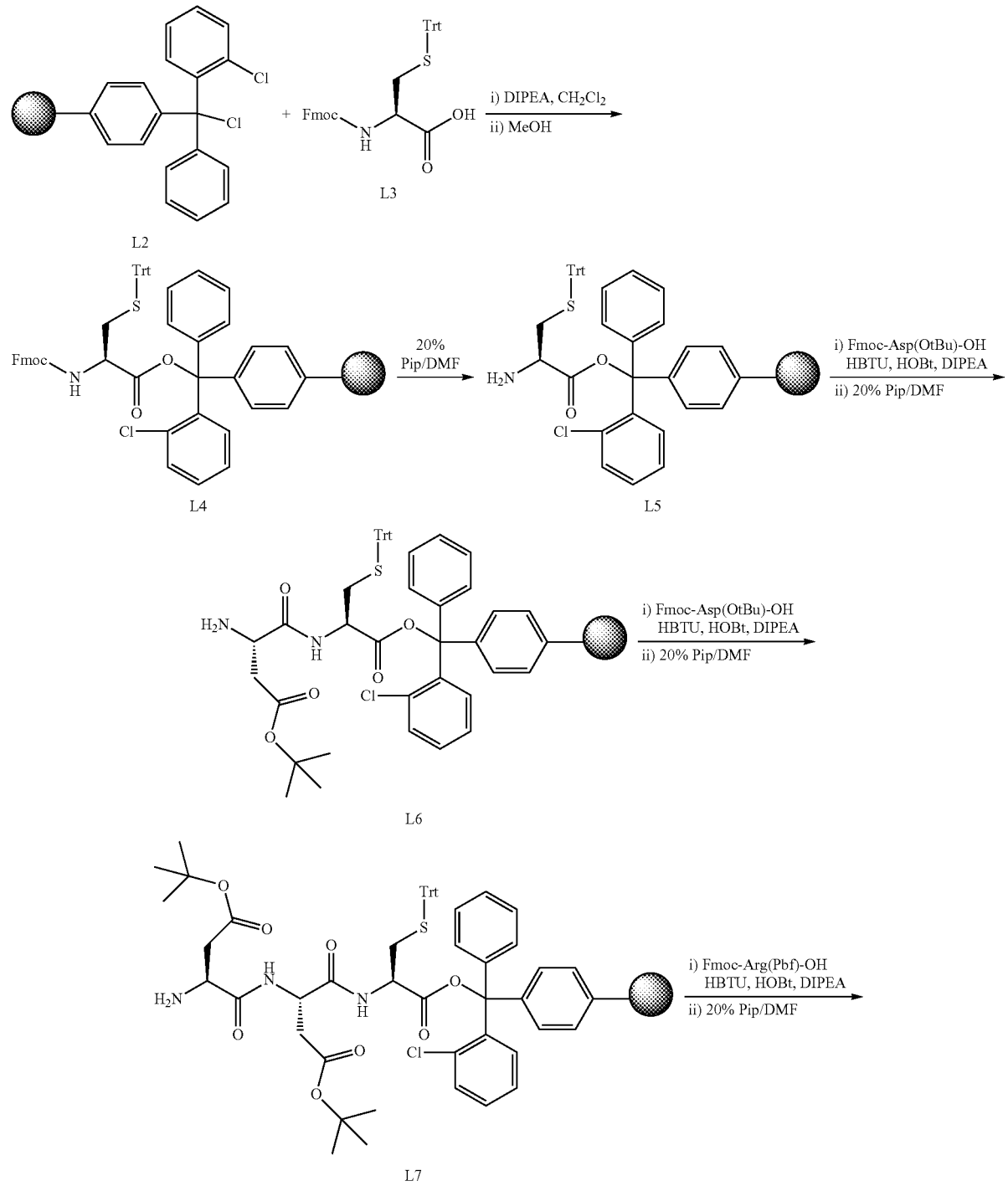

Scheme 7A

-continued
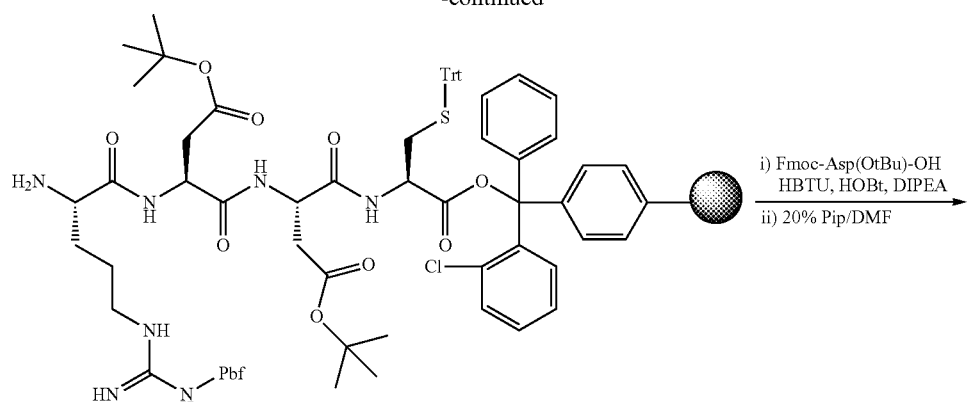
L8
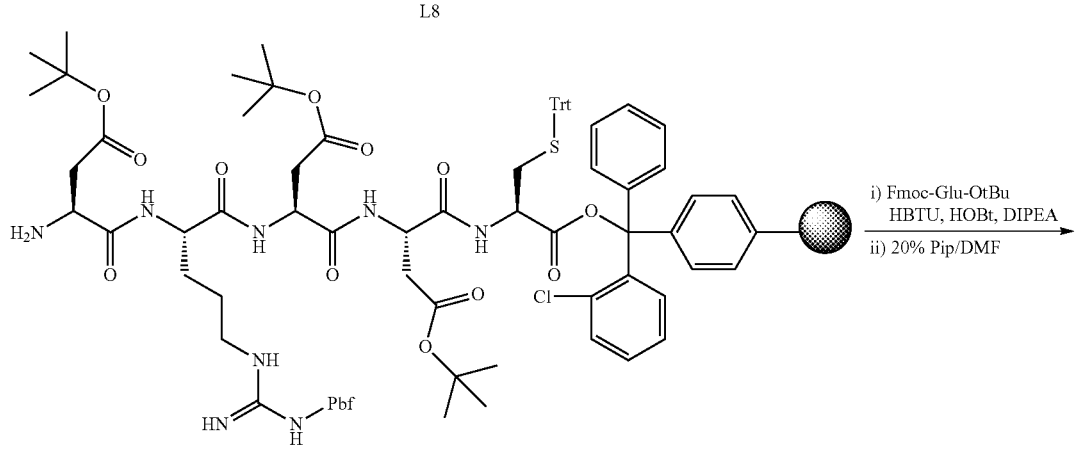
L9
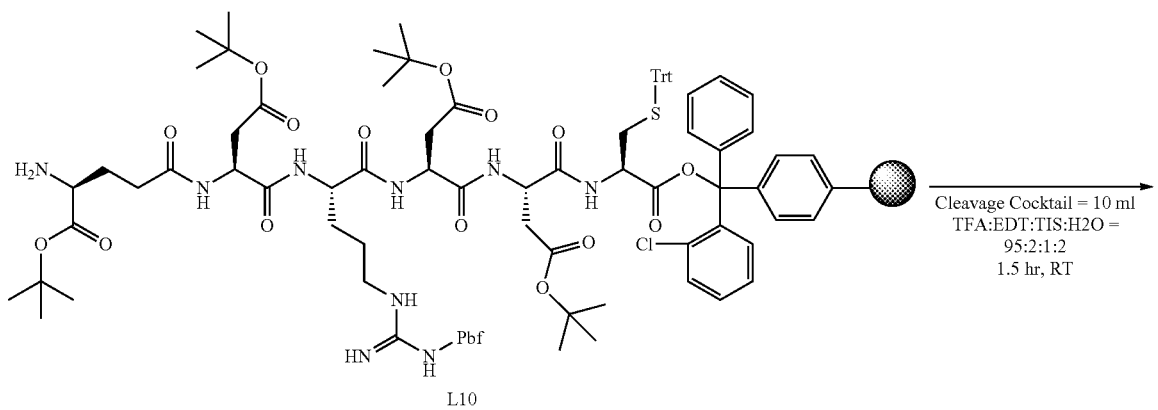
L10
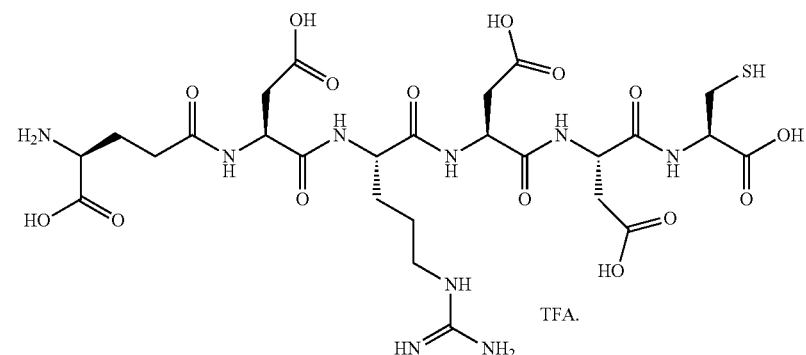
intermediate A

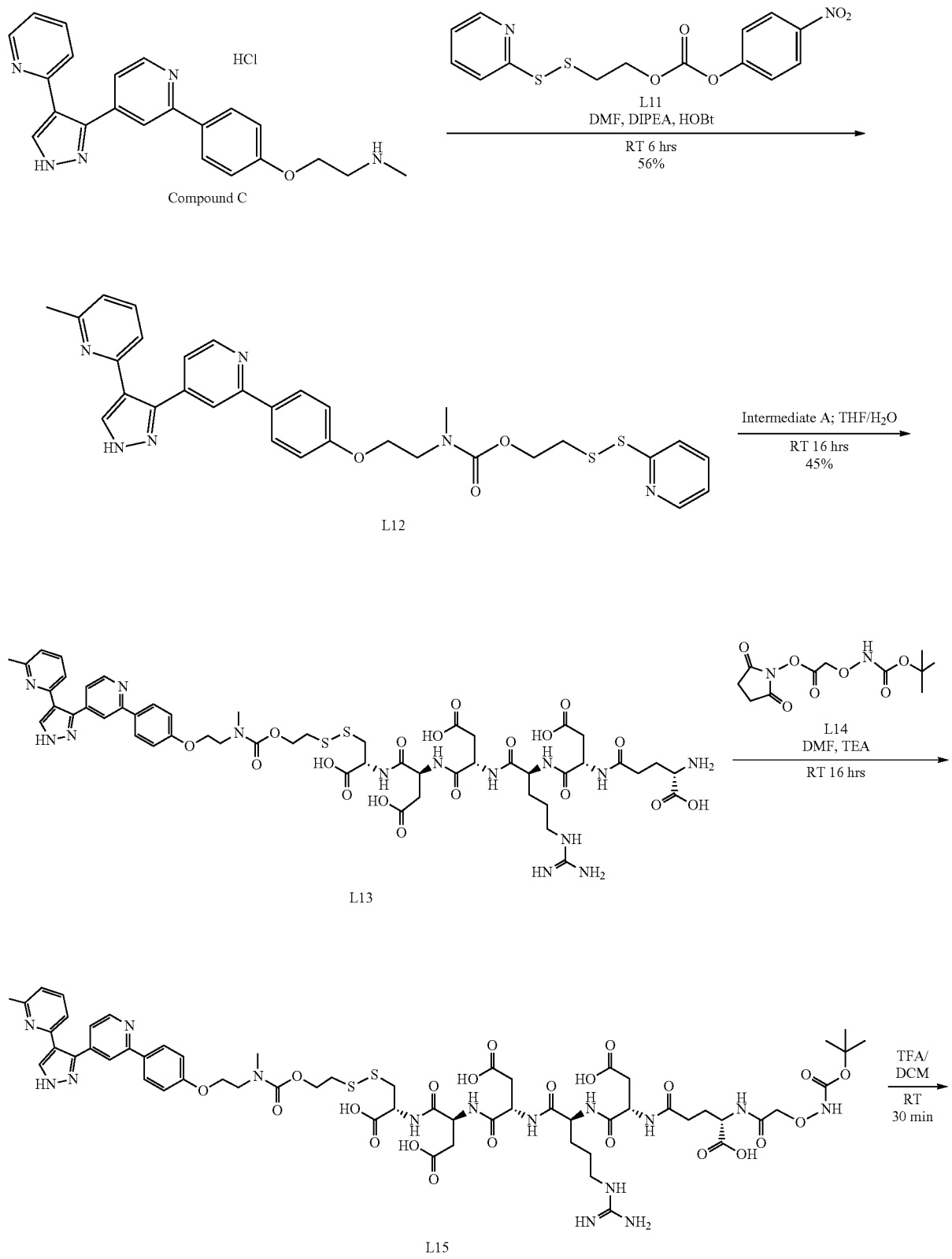

-continued

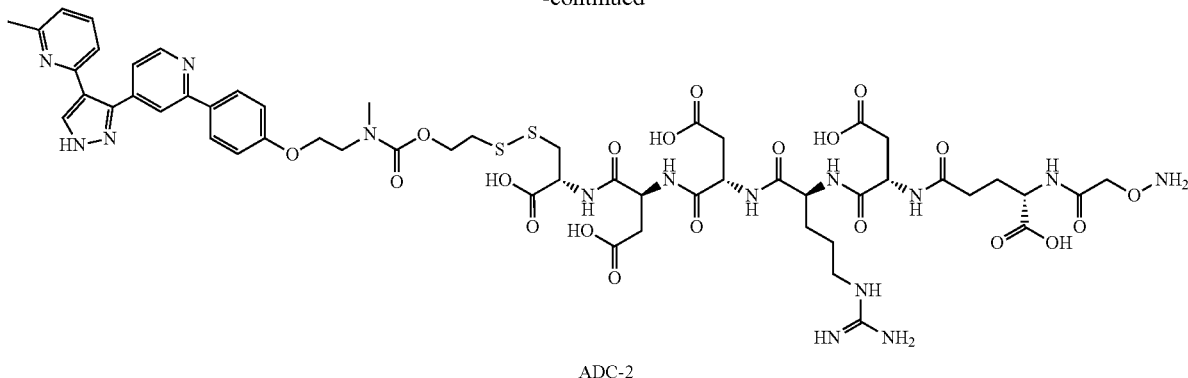

ADC-2

6.9.1. Synthesis of Intermediate A 2-chlorotrityl chloride resin (L2) (4 g, 4 mmol) is washed with DCM (2×40 ml), swelled in 50 ml DCM for 10 min, and then drained. Fmoc-Cys(Trt)-OH (L3) (7.03 g, 12 mmol) is dissolved in 40 ml DCM and added to the vessel containing the 2-chlorotrityl chloride resin. 8.7 ml DIPEA (6.8 ml, 40 mmol) is added to the vessel, and the mixture is swirled for 2 hr at approximately 21° C. 10 ml of methanol is then added to the mixture and swirled for 30 minutes. The resulting resin (L4) is then drained and washed five times with DMF. Resin L4 is then deprotected to provide resin L5 by adding approximately 40 ml of 20% piperidine in DMF to resin L4, shaking the mixture, and then draining the liquid from the resin. Another 40 ml of 20% piperidine in DMF is added to the resin and shaken for 15 minutes. The resin L5 is then drained of liquid and washed with DMF (6×40 ml).

Solutions of Fmoc-amino acid are prepared by separately combining Fmoc-Asp(OtBu)-OH (4.93 g, 12 mmol), Fmoc-Asp(OtBu)-OH (4.93 g, 12 mmol), Fmoc-Arg(Pbf)-OH (7.79 g, 12 mmol), Fmoc-Asp(OtBu)-OH (4.93 g, 12 mmol), and Fmoc-Glu-OtBu (5.1 g, 12 mmol) with HBTU/HOBT (4.55 g, 12 mmol/1.62 g, 12 mmol) and DIPEA (2 ml, 12 mmol).

The Fmoc-Asp(OtBu)-OH solution is added to resin L5 and shaken for 60 minutes to provide resin L6. The resin L6 is washed with DMF (6×40 ml), and then deprotected with 20% piperidine in DMF as above. Resins L7, L8, L9, and L10 are then made by performing sequential couplings using the Fmoc-amino acid solutions and the same procedure used to make resin L6 from resin L5.

In an exemplary synthesis, dry resin L10 (8 g) was added to a flask and 80 ml cleavage solution was added (TFA:TES:EDT:H$_2$O=90:5:3:2, v/v/v/v). The reaction was allowed to proceed for 1.5 hours. The resin was then separated from the reaction mixture by filtration under pressure. The resin was then washed twice with TFA. The filtrates were combined, and a 10-fold volume of cold MTBE was added dropwise. The precipitated peptide (Intermediate A) was then centrifuged and washed with cold MTBE four times. Intermediate A was then dried at reduced pressure, and purified by preparative HPLC to provide 1.1 g of Intermediate A as a white solid (yield: 37%). LC-MS (ESI) m/z: 752 [M+H]+.

6.9.2. 2-(pyridin-2-yldisulfanyl)ethylmethyl(2-(4-(4-(4-(6-methylpyridin-2-yl)-1H-pyrazol-3-yl)pyridin-2-yl)phenoxy)ethyl)carbamate (L12)

To a solution of Compound C (40 mg, 0.1038 mmol) and 4-nitrophenyl 2-(pyridin-2-yldisulfanyl)ethyl carbonate (L11) (80 mg, 0.2272 mmol) in DMF (5 ml) was added DIPEA (0.5 ml) and HOBt (14 mg, 0.1038 mmol). The mixture was stirred at approximately 21° C. under N$_2$ for 16 hrs to provide L12. The crude L12 was purified by preparative-HPLC to give 35 mg of purified L12 as a white solid (yield 56%).

6.9.3. (2R,5S,8S,11S,14S,19S)-19-amino-5,8,14-tris(carboxy methyl)-11-(3-guanidinopropyl)-2-(((2-(methyl(2-(4-(4-(4-(6-methylpyridin-2-yl)-1H-pyrazol-3-yl)pyridin-2-yl)phenoxy)ethyl)carbamoyloxy)ethyl) disulfanyl) methyl)-4,7,10,13,16-pentaoxo-3,6,9,12,15-pentaazaicosane-1,20-dioic acid (L13)

To a solution of L12 (35 mg, 0.058 mmol) in THF/H$_2$O (5 ml/5 ml) was added Intermediate A (80 mg, 0.106 mmol) under N$_2$. The mixture was stirred at approximately 21° C. for 16 hr to provide L13. The crude L13 was purified by preparative HPLC to provide 23 mg of purified L13 as a white solid (yield 31%).

6.9.4. (2R,5S,8S,11S,14S,19S)-19-(2-(tert-butoxy carbonyl aminooxy)acetamido)-5,8,14-tris(carboxymethyl)-11-(3-guanidinopropyl)-2-(((2-(methyl (2-(4-(4-(4-(6-methylpyridin-2-yl)-1H-pyrazol-3-yl)pyridin-2-yl)phenoxy)ethyl)carbamoyloxy)ethyl)disulfanyl)methyl)-4,7,10,13,16-pentaoxo-3,6,9,12,15-pentaazaicosane-1,20-dioic acid (L15)

To a solution of L13 (32 mg, 0.025 mmol) in DMF (3 ml) was added 2,5-dioxopyrrolidin-1-yl2-(tert-butoxycarbonylaminooxy)acetate (L14) (28 mg, 0.097 mmol) followed by TEA (0.5 ml). The reaction mixture was stirred at approximately 21° C. under N$_2$ atmosphere for 16 hr to provide L15. The crude L15 was purified by preparative HPLC to provide 12 mg of purified L15 as white solid (yield 33%)

6.9.5. (2R,5S,8S,11S,14S,19S)-19-(2-(aminooxy) acetamido)-5,8,14-tris(carboxymethyl)-11-(3-guanidinopropyl)-2-(((2-(methyl(2-(4-(4(4-(6-methylpyridin-2-yl)-1H-pyrazol-3-yl)pyridin-2-yl)phenoxy) ethyl)carbamoyloxy)ethyl)disulfanyl)methyl)-4,7,10, 13,16-pentaoxo-3,6,9,12,15-penta azaicosane-1,20-dioic acid (ADC-2)

To a mixture of L15 (12 mg, 0.0085 mmol) in DCM (5 ml) was added TFA (1 ml). The mixture was stirred at approximately 21° C. for 30 minutes to provide ADC-2. The crude ADC-2 was concentrated and purified with preparative HPLC to provide 3.5 mg of purified ADC-2 as a white solid (yield 31%).

6.10. Example 10: Generation of Antibody Drug Conjugate 2 (ADC2)

ADC-2 was attached to an anti-TfR antibody via antibody lysine residues according to the general methodology in Scheme 8 below:

The heterobifunctional linker S-4FB was purchased from Solulink. Rat anti-mouse IgG2a and anti-mouse transferrin receptor antibody R17217 were dialyzed into PBS, pH 7.4. S-4FB was added to the antibodies in PBS, pH 7.4 at different molar ratios and incubated at approximately 21° C. for 3 hours The S-4FB-modified antibody solution was combined with a 2-hydrazinopyridine solution (0.5 mM, in 100 mM MES buffer, pH 5.0) and incubated at 37° C. for 30 minutes at various conjugation ratios, ranging from 5-50. The S4FB/Ab molar substitution ratio was determined by UV-Vis at A354. The modified antibody was purified using a Zeba™ spin desalting column, buffer exchanged into 50 mM phosphate buffer (pH 6.5, 150 mM NaCl) and then mixed with linker-S—S-drug ADC-2 (10 mM, in DMSO) at different molar ratios for 24 hours at 37° C. to provide ADC2. The next day, ADC2 samples were dialyzed against PBS overnight. The samples were filtered and then tested via HPLC-SEC, SDS-PAGE and LC-MS. Exemplary LC-MS data for ADC2 prepared with a S-4FB/Ab ratio of 6 and a ADC-2/Ab ratio of 20 is shown in FIG. 7. FIG. 7 shows that the tested ADC2 sample had an average DAR of 4.99, with the DAR of the heavy chain being 1.97 and DAR of the light chain being 0.53.

If ADC2 aggregation over 5% was detected by HPLC-SEC, the aggregated components were separated by AKTA with SEC columns (GE Healthcare Life Sciences, Superdex 200 increase 10/300 GL) and analyzed again by HPLC-SEC.

Scheme 8

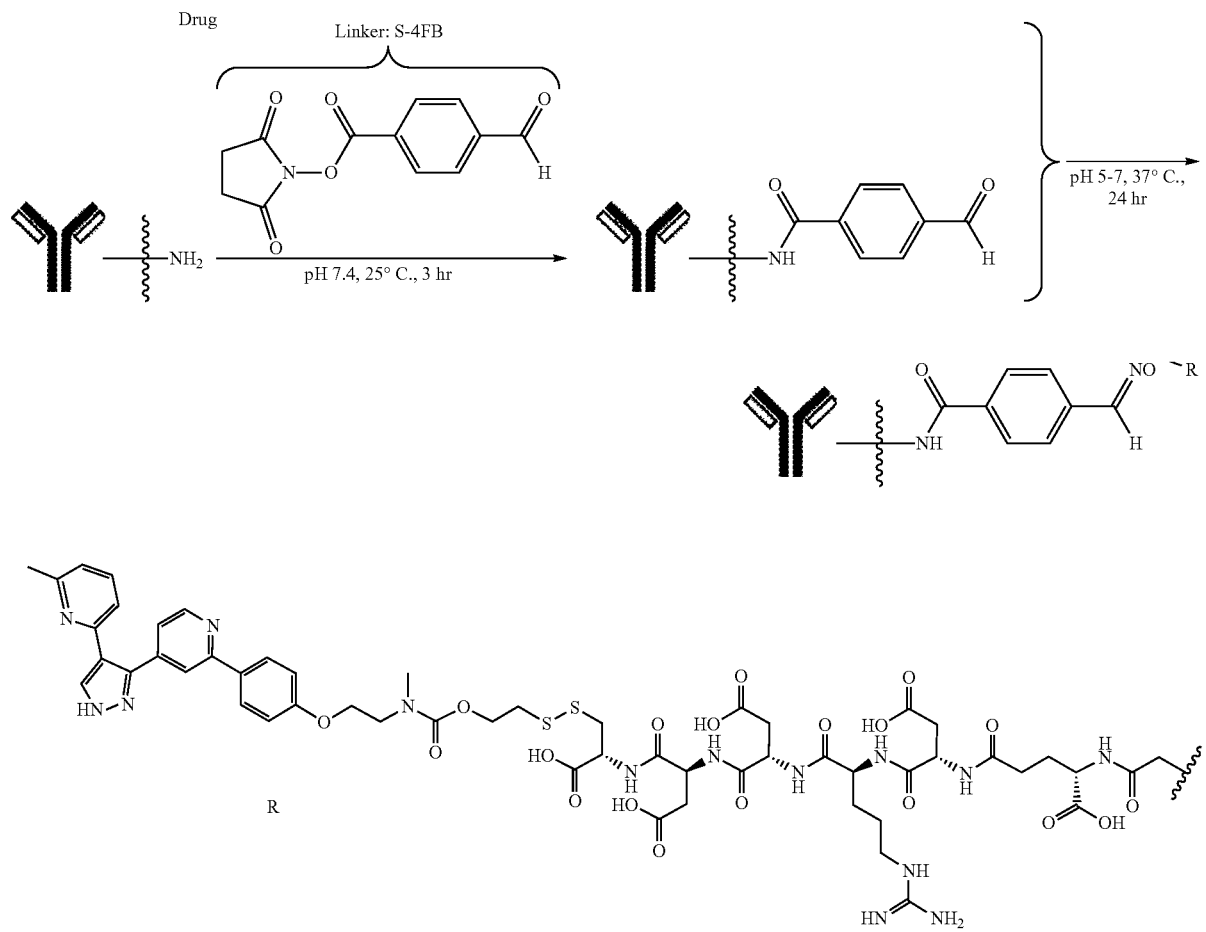

A chromatogram of ADC2 purified by SEC to remove aggregates is shown in FIG. 8.

6.11. Example 11: Antibody-Induced Receptor Internalization Assay 96-well flat bottom plates were coated with anti-mouse CD3e antibody overnight at 4 degrees. CD4+ T cells were isolated from mouse spleens using the RoboSep™ cell isolation system (Stemcell Technologies). Approximately $2 \times 10^5$ cells were plated per well with soluble anti-CD28 antibody for 24-48 hour at 37 degrees. Once activated, the $CD4^+$ T cells were harvested, washed and re-plated with 5 µg/ml primary (anti-transferrin receptor) antibody for indicated time points at 37 degrees to induce internalization. The reaction was stopped with ice cold staining buffer and kept on ice to stop internalization. At the end of the assay, cells were washed twice in ice-cold staining buffer to remove unbound antibody. Cells were pelleted and then stained with PE conjugated goat anti-rat secondary antibody and incubated for 30 minutes on ice. Cells were washed with staining buffer and then analyzed for expression via FACS. As shown in FIG. 9, TfR expression begins to internalize in primary $CD4^+$ T cells within 1 hour and within 3 hours, more than 70% of the TfR has been internalized by anti-transferrin receptor antibody, R17217.

6.12. Example 12: In Vitro Assays

6.12.1. Proliferation Assay

Mouse CTLL2 cells were cultured at $1 \times 10^5$ cells/well in 0.2 ng/ml IL2. To each well as indicated 1 nM TGF-β, 1 µg/ml ADC, and/or 100 nM ALK5 inhibitor Compound C was added to the wells for 24 hours. Proliferation was quantitated via addition of the BrdU reagent (Abcam) to each well for another 12 hours and then analyzed by ELISA.

As demonstrated in FIG. 10, treatment of CTLL2 cells with TGF-β inhibited proliferation by approximately 60%. However, addition of ADC1 (DAR 2-4, 4-6 or 6-8) led to almost complete reversal of TGF-β inhibition and restoration of CTLL2 proliferation, similar to treatment of cells with ALK5 inhibitor alone. Cells treated with rat anti-mouse IgG2A isotype control ALK5 ADC did not restore CTLL2 proliferation. In cells treated with ADC1 in the absence of TGF-β or with the naked Tfr antibody alone, there was no inhibition of proliferation, indicating that ADC1 did not affect proliferation, unless TGF-β was present (data not shown).

6.12.2. Granzyme B Expression Assay

Mouse $CD3^+$ T cells were purified from mouse spleens using the EasySep™ Mouse T cell isolation kit (negative selection) (Stemcell Technologies). $CD3^+$ T cells were activated as before using plate bound antiCD3e and soluble anti-CD28 for 48 hours. T cells were washed and re-plated in media with 5% serum plus 1 nM TGF-β−/+ADC.

Golgi stop reagent was added for the last 4 hours and then the cells were immunostained for surface CD8 (BD) and intracellular GzmB (eBioscience) and analyzed via flow cytometry. Granzyme B (GzmB) is a serine protease released by $CD8^+$ T cells to kill tumor cells. Thus, increased expression of GzmB is indicative of $CD8^+$ cytotoxic T cell activation.

As shown in FIG. 11, even though TGF-β represses GzmB expression in primary $CD8^+$ T cells, treatment with ADC1 at all 3 DARS, 2-4, 4-6 and 6-8, could also restore GzmB expression, comparable to ALK5 compound. In addition, the rat anti-mouse IgG2A isotype control ALK5 ADC did not restore GzmB expression.

6.12.3. iTreg Conversion Assay

Naïve CD4 T cells were isolated from isolated mouse spleenocytes using a negative selection kit. The cell density was adjusted to $0.4 \times 10^6$ cells/ml, and 10 ng/ml of mouse IL-2, 20 ng/ml of TGF-β, and 1 µg/ml of soluble anti-CD28 was added to the cell suspension.

Anti-mouse CD3 antibody at 10 µg/ml was coated on a 24 well plate and incubated at 4° C. overnight. The antibody was then aspirated from the plate. 1 ml of the cell suspension was added to each well of the 24 well plate. ADC1 (DAR 4-6) at 3 µg/ml and 5 µg/ml, anti-transferrin receptor antibody, rat anti-mouse IgG2A isotype control ALK5 ADC, and ALK5 inhibitor Compound C at 100 nM and 1 µM were added to separate wells of the 24 well plate. The cells were then cultured for 72 hours. TfR expression was tested at 48 hours (data not shown). Cells were stained for FoxP3 (eBioscience FoxP3 staining buffer) and sorted by FACS at 72 hours.

As shown in FIG. 12, ADC1 at 5 µg/ml (+CD71-ALK5 ADC) modestly decreased the amount of iTreg generated, similar to 100 nM of free ALK5 inhibitor alone (+ALK5 inh 100 nM). In contrast, the control ALK5 ADC (+Iso-ALK5 ADC) and naked anti-TfR antibody (+anti-CD71) had no effect on iTreg FoxP3 expression.

7. SPECIFIC EMBODIMENTS

The present disclosure is exemplified by the specific embodiments below.

1. An antibody-ALK5 inhibitor conjugate (ADC) comprising an ALK5 inhibitor operably linked to an antibody or antigen binding fragment that binds to a T cell surface molecule.

2. The ADC of embodiment 1, wherein the ALK5 inhibitor has an $IC_{50}$ of at least 20 nM.

3. The ADC of embodiment 1 or embodiment 2, wherein the ALK5 inhibitor is an imidazole type compound, a pyrazole type compound, or a thiazole type compound.

4. The ADC of embodiment 3, wherein the ALK5 inhibitor is an imidazole type compound which is an imidazole-benzodioxol compound or an imidazole-quinoxaline compound.

5. The ADC of embodiment 3, wherein the ALK5 inhibitor is pyrazole type compound which is a pyrazole-pyrrolo compound.

6. The ADC of embodiment 3, wherein the ALK5 inhibitor is an imidazole-benzodioxol compound, an imidazole-quinoxaline compound, a pyrazole-pyrrolo compound, or a thiazole type compound.

7. The ADC of any one of embodiments 1 to 6, wherein the ALK5 inhibitor is linked to the antibody or antigen binding fragment via a linker.

8. The ADC of embodiment 7, wherein the linker is a non-cleavable linker.

9. The ADC of embodiment 8, wherein the non-cleavable linker is an N-maleimidomethylcyclohexanel-carboxylate, maleimidocaproyl or mercaptoacetamidocaproyl linker.

10. The ADC of embodiment 7, wherein the linker is a cleavable linker.

11. The ADC of embodiment 10, wherein the cleavable linker is a dipeptide linker, a disulfide linker, or a hydrazone linker.

12. The ADC of embodiment 11, wherein the linker is a protease-sensitive valine-citrulline dipeptide linker.

13. The ADC of embodiment 11, wherein the linker is a glutathione-sensitive disulfide linker.

14. The ADC of embodiment 11, wherein the linker is an acid-sensitive disulfide linker.

15. The ADC of any one of embodiments 1 to 10, wherein the ALK5 inhibitor is conjugated via one or more cysteine residues on the antibody or antigen binding fragment.

16. The ADC of any one of embodiments 1 to 10, wherein the ALK5 inhibitor is conjugated via one or more lysine residues on the antibody or antigen binding fragment.

17. The ADC of embodiment 15 or embodiment 16, wherein the ALK5 inhibitor is conjugated via a linker.

18. The ADC of any one of embodiments 1 to 17, wherein the wherein the average number of ALK5 inhibitor molecules per antibody or antigen binding fragment molecule ranges between 2 and 8.

19. The ADC of any one of embodiments 1 to 18, wherein the antibody is a monoclonal antibody.

20. The ADC of embodiment 19, wherein the antibody is human or humanized.

21. The ADC of any one of embodiments 1 to 18, wherein the antigen binding fragment is a Fab, Fab', F(ab')$_2$ or Fv fragment.

22. The ADC of embodiment 21, wherein the antigen binding fragment is an antigen binding fragment of a human or humanized antibody.

23. The ADC of any one of embodiments 1 to 22, wherein the T cell surface molecule is CD1, CD2, CD3, CD4, CD5, CD6, CD7, CD8, CD25, CD28, CD70, CD71, CD103, CD184, Tim3, LAG3, CTLA4, or PD1.

24. A pharmaceutical composition comprising the ADC of any one of embodiments 1 to 23 and a pharmaceutically acceptable carrier.

25. A method of treating cancer, comprising administering to a subject in need thereof an ADC according to any one of embodiments 1 to 23 or a pharmaceutical composition according to embodiment 24.

26. The method of embodiment 25, wherein the cancer is an immunogenic cancer.

27. The method of embodiment 26, wherein the cancer is a solid tumor that expresses a tumor antigen.

28. The method of embodiment 27, wherein the tumor antigen is gp100, melanA or MAGE A1.

29. The method of embodiment 25, wherein the cancer is a solid tumor comprising immune infiltrates.

30. The method of embodiment 25, wherein the cancer is treatable by immunotherapy.

31. The method of embodiment 30, wherein the immunotherapy is cytokine therapy, adoptive T cell therapy, chimeric antigen receptor (CAR) therapy or T cell checkpoint inhibitor therapy.

32. The method of embodiment 31, wherein the T cell checkpoint inhibitor is an inhibitor of PD1, PDL1, or CTLA4.

33. The method of any one of embodiments 30 to 32 wherein the cancer is non-small cell lung cancer (NSCLC), bladder cancer, renal cancer, breast cancer, or melanoma.

34. The method of embodiment 25, wherein the cancer is treatable by ALK5 inhibitors.

35. The method of any one of embodiments 25 to 34, wherein the ADC or pharmaceutical composition is administered as monotherapy.

36. The method of any one of embodiments 25 to 34, wherein the ADC or pharmaceutical composition is administered as part of a combination therapy regimen.

37. The method of embodiment 36, wherein the ADC or pharmaceutical composition is administered in combination with a standard of care therapy or therapeutic regimen.

While various specific embodiments have been illustrated and described, it will be appreciated that various changes can be made without departing from the spirit and scope of the disclosure(s).

8. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A composition comprising an ALK5 inhibitor covalently attached to a protease-sensitive linker, wherein the wherein the ALK5 inhibitor has the structure

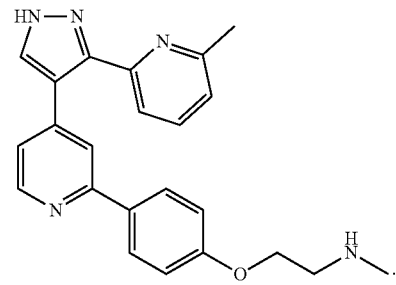 [SMILES: CNCCOc1ccc(-c2cc(-c3c[nH]nc3-c3cccc(C)n3)ccn2)cc1]

2. The composition of claim 1, wherein the protease-sensitive linker comprises a dipeptide, a tripeptide, a tetrapeptide, or a pentapeptide.

3. The composition of claim 1, wherein the protease-sensitive linker comprises a valine-citrulline dipeptide.

* * * * *